(12) United States Patent
Park

(10) Patent No.: US 10,062,849 B2
(45) Date of Patent: Aug. 28, 2018

(54) CONDENSED-CYCLIC COMPOUND AND ORGANIC LIGHT-EMITTING DEVICE INCLUDING THE SAME

(71) Applicant: SAMSUNG DISPLAY CO., LTD., Yongin-si, Gyeonggi-do (KR)

(72) Inventor: Sanghoon Park, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 206 days.

(21) Appl. No.: 14/981,806

(22) Filed: Dec. 28, 2015

(65) Prior Publication Data
US 2016/0301010 A1    Oct. 13, 2016

(30) Foreign Application Priority Data

Apr. 13, 2015    (KR) .................. 10-2015-0052075

(51) Int. Cl.
*H01L 51/00* (2006.01)
*H01L 51/50* (2006.01)
*C07D 401/04* (2006.01)

(52) U.S. Cl.
CPC ........ *H01L 51/0054* (2013.01); *C07D 401/04* (2013.01); *H01L 51/0052* (2013.01); *H01L 51/0067* (2013.01); *H01L 51/0072* (2013.01); *H01L 51/5072* (2013.01)

(58) Field of Classification Search
None
See application file for complete search history.

(56) References Cited

U.S. PATENT DOCUMENTS

| | | | |
|---|---|---|---|
| 2007/0122656 A1 | 5/2007 | Klubek et al. | |
| 2007/0290610 A1* | 12/2007 | Park ..................... | C07C 211/54 313/504 |
| 2009/0102361 A1 | 4/2009 | Miki et al. | |
| 2009/0108746 A1 | 4/2009 | Park et al. | |
| 2009/0134780 A1 | 5/2009 | Ono et al. | |
| 2014/0014925 A1 | 1/2014 | Jung et al. | |
| 2014/0209872 A1 | 7/2014 | Park et al. | |
| 2014/0306190 A1* | 10/2014 | Lee ..................... | H01L 51/0054 257/40 |

FOREIGN PATENT DOCUMENTS

| | | |
|---|---|---|
| JP | 2003-123983 A | 4/2003 |
| JP | 2004-175691 A | 6/2004 |
| JP | 2005-038241 A | 2/2005 |
| KR | 10-2009-0044975 A | 5/2009 |
| KR | 10-2014-0008235 A | 1/2014 |
| KR | 10-2014-0096662 A | 8/2014 |
| WO | WO 2007/026847 A1 | 3/2007 |
| WO | WO 2007/029696 A1 | 3/2007 |
| WO | WO 2007/064493 A1 | 6/2007 |
| WO | WO 2007/086552 A1 | 8/2007 |

OTHER PUBLICATIONS

Machine-assisted English translation for KR 10-2009-0044975 (2009) provided by KIPO.*
Abstract for Japanese Pub. No. JP 5119929 B2, dated Jan. 16, 2013, for corresponding WO 2007/086552 A1, 2 pages.

* cited by examiner

*Primary Examiner* — Sin J Lee
(74) *Attorney, Agent, or Firm* — Lewis Roca Rothgerber Christie LLP

(57) ABSTRACT

A condensed-cyclic compound is represented by Formula 1. An organic light-emitting device includes a first electrode, a second electrode facing the first electrode, and an organic layer between the first electrode and the second electrode and including an emission layer, where the organic layer includes at least one of the condensed-cyclic compounds represented by Formula 1.

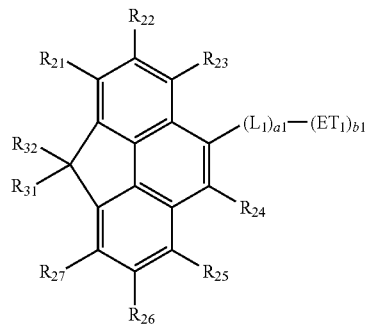

Formula 1

20 Claims, 1 Drawing Sheet

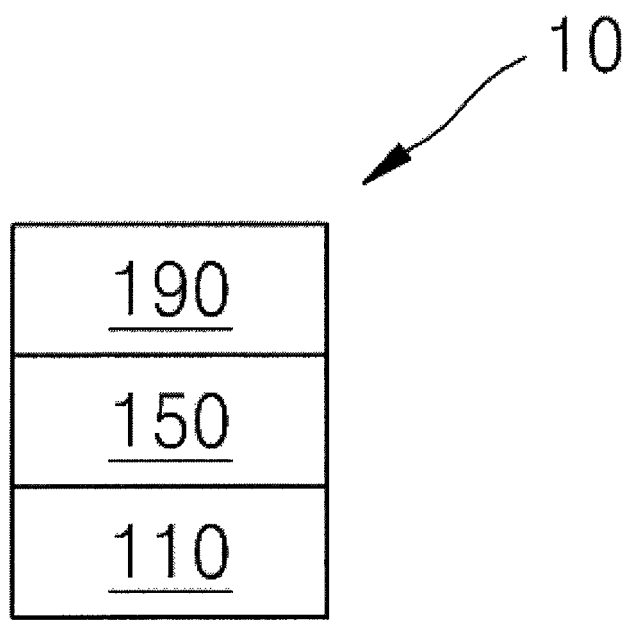

CONDENSED-CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0052075, filed on Apr. 13, 2015, in the Korean Intellectual Property Office, the entire content of which is incorporated herein by reference.

BACKGROUND

1. Field

One or more example embodiments relate to a condensed-cyclic compound and an organic light-emitting device including the same.

2. Description of the Related Art

In general, an organic light-emitting device is a self-emission device that has a wide viewing angle, a high contrast ratio, a fast response rate, and excellent brightness, driving voltage, and response speed characteristics, and produces full-color images.

The organic light-emitting device may have a structure in which a first electrode is disposed on a substrate. Further, a hole transport region, an emission layer, an electron transport region, and a second electrode are sequentially formed on the first electrode. Holes provided by the first electrode move toward the emission layer through the hole transport region, and electrons provided by the second electrode may move toward the emission layer through the electron transport region. Carriers, such as the holes and the electrons, are recombined in the emission layer to produce excitons. These excitons change from an excited state to a ground state, thereby generating light.

SUMMARY

One or more example embodiments include a condensed-cyclic compound and an organic light-emitting device including the same.

Additional aspects of embodiments will be set forth, in part, in the description which follows and, in part, will be apparent from the description, or may be learned by practice of the presented embodiments.

According to one or more example embodiments, a condensed-cyclic compound is represented by Formula 1:

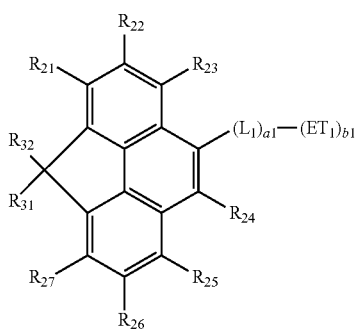

Formula 1

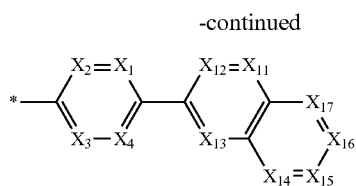

Formula 2-1

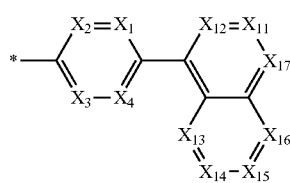

Formula 2-2

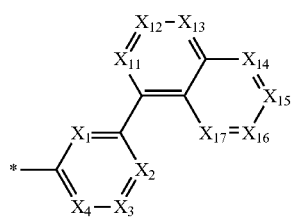

Formula 2-3

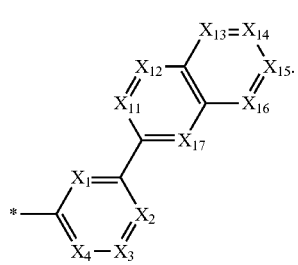

Formula 2-4

In the above formulae, $L_1$ may be selected from a substituted or unsubstituted phenylene group and a substituted or unsubstituted naphthylene group, a1 may be selected from 0, 1, 2, and 3, and when a1 is 2 or more, two or more $L_1$(s) may be identical to or different from each other, $ET_1$ may be an electron-transporting moiety and may be selected from groups represented by Formulae 2-1 to 2-4, $X_1$ may be N or $C(R_1)$, $X_2$ may be N or $C(R_2)$, $X_3$ may be N or $C(R_3)$, $X_4$ may be N or $C(R_4)$, $X_{11}$ may be N or $C(R_{11})$, $X_{12}$ may be N or $C(R_{12})$, $X_{13}$ may be N or $C(R_{13})$, $X_{14}$ may be N or $C(R_{14})$, $X_{15}$ may be N or $C(R_{15})$, $X_{16}$ may be N or $C(R_{16})$, and $X_{17}$ may be N or $C(R_{17})$, at least one of $X_1$ to $X_4$ and $X_{11}$ to $X_{17}$ may be N, b1 may be selected from 1, 2, and 3, $R_1$ to $R_4$, $R_{11}$ to $R_{17}$, and $R_{21}$ to $R_{27}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted biphenyl group, a substituted or unsubstituted terphenyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_4$)($Q_5$), and —N($Q_6$)($Q_7$), $R_{31}$ and $R_{32}$ may be each independently selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted biphenyl group, a substituted or unsubstituted terphenyl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, at least one of the substituents of the substituted phenylene group, substituted naphthylene group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted biphenyl group, substituted terphenyl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —B($Q_{14}$)($Q_{15}$), and —N($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a biphenyl group, a terphenyl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a biphenyl group, a terphenyl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —B($Q_{24}$)($Q_{25}$), and —N($Q_{26}$)($Q_{27}$); and —Si($Q_{31}$)($Q_{32}$)($Q_{33}$), —B($Q_{34}$)($Q_{35}$), and —N($Q_{36}$)($Q_{37}$), where $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and

* may indicate a binding site to a neighboring atom.

According to one or more example embodiments, an organic light-emitting device includes a first electrode, a second electrode facing the first electrode, and an organic layer between the first electrode and the second electrode and including an emission layer, where the organic layer includes at least one of the condensed-cyclic compounds described above.

BRIEF DESCRIPTION OF THE DRAWING

These and/or other aspects will become apparent and more readily appreciated from the following description of example embodiments and the accompanying drawing, which schematically illustrates a structure of an organic light-emitting device according to an embodiment.

DETAILED DESCRIPTION

Reference will now be made in detail to example embodiments, an example of which is illustrated in the accompanying drawing. In this regard, the present example embodiments may have different forms and should not be construed as being limited to the descriptions set forth herein. Accordingly, the example embodiments are merely described below, by referring to the accompanying drawing, to explain aspects of the present description. Expressions such as "at least one of," when preceding a list of elements, modify the entire list of elements and do not modify the individual elements of the list. Also, in the context of the present application, when a first element is referred to as being "on" a second element, it can be directly on the second element or be indirectly on the second element with one or more intervening elements interposed therebetween. For example, as described herein a first electrode or a second electrode may be directly or indirectly on a substrate.

A condensed-cyclic compound according to an embodiment is represented by Formula 1 below:

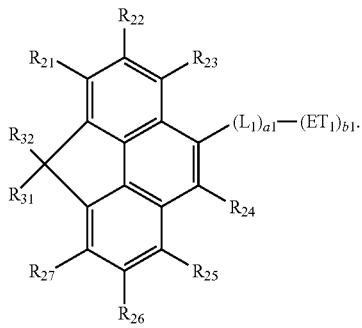

Formula 1

$L_1$ in Formula 1 may be selected from a substituted or unsubstituted phenylene group and a substituted or unsubstituted naphthylene group.

For example, $L_1$ in Formula 1 may be selected from a phenylene group; a naphthylene group; and a phenylene group and a naphthylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

In some embodiments, $L_1$ in Formula 1 may be selected from a phenylene group and a naphthylene group.

In Formula 1, a1 may be selected from 0, 1, 2, and 3. In Formula 1, a1 indicates the number of $L_1$ (e.g., the number of $L_1$ groups), when a1 is 0, -$(L_1)_{a1}$- may be a single bond, and when a1 is 2 or more, two or more $L_1$(s) ($L_1$ groups) may be identical to or different from each other.

For example, a1 in Formula 1 may be 0 or 1.

$ET_1$ in Formula 1 may be an electron-transporting moiety and may be selected from groups represented by Formulae 2-1 to 2-4 below.

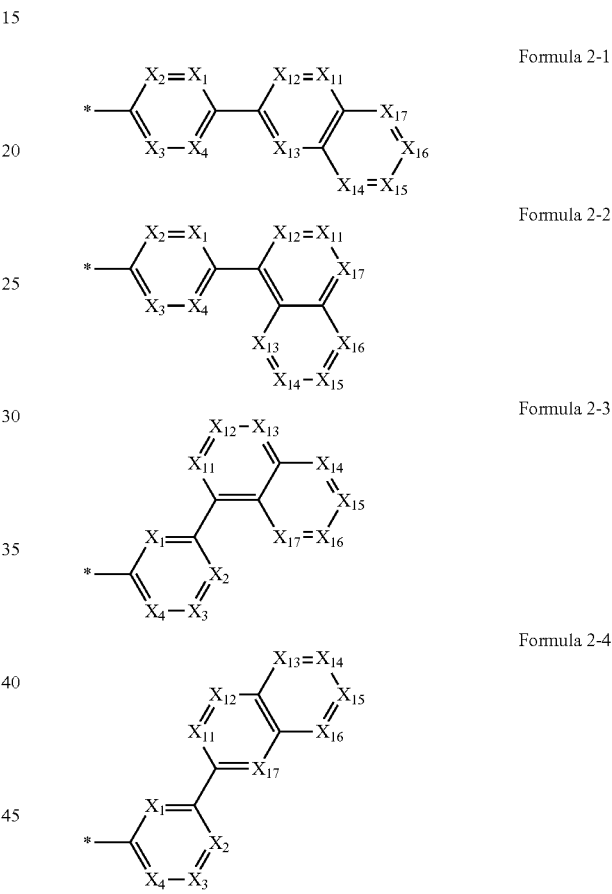

In Formulae 2-1 to 2-4, $X_1$ may be N or $C(R_1)$, $X_2$ may be N or $C(R_2)$, $X_3$ may be N or $C(R_3)$, $X_4$ may be N or $C(R_4)$, $X_{11}$ may be N or $C(R_{11})$, $X_{12}$ may be N or $C(R_{12})$, $X_{13}$ may be N or $C(R_{13})$, $X_{14}$ may be N or $C(R_{14})$, $X_{15}$ may be N or $C(R_{15})$, $X_{16}$ may be N or $C(R_{16})$, $X_{17}$ may be N or $C(R_{17})$, and at least one of $X_1$ to $X_4$ and $X_{11}$ to $X_{17}$ may be N. In Formulae 2-1 to 2-4, * indicates a binding site to a neighboring atom (e.g., * represents a connection (a bond) to the remaining portion of Formula 1 (e.g., a connection to $L_1$)).

For example, at least one of $X_1$ to $X_4$ and $X_{11}$ to $X_{17}$ in Formulae 2-1 to 2-4 may be N.

In some embodiments, at least two of $X_1$ to $X_4$ and $X_{11}$ to $X_{17}$ in Formulae 2-1 to 2-4 may be N.

In some embodiments, in Formulae 2-1 to 2-4, at least one of $X_1$ to $X_4$ may be N, and at least one of $X_{11}$ to $X_{17}$ may be N.

In some embodiments, in Formulae 2-1 to 2-4, one of $X_1$ to $X_4$ may be N, and one of $X_{11}$ to $X_{17}$ may be N.

For example, ET$_1$ in Formula 1 may be selected from groups represented by Formulae 7-1 to 7-84 below:
Formula 7-1
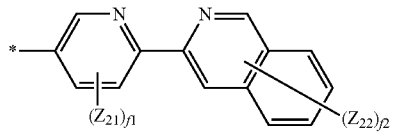
Formula 7-2
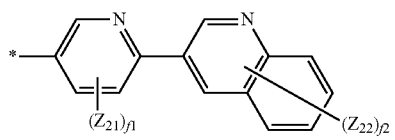
Formula 7-3
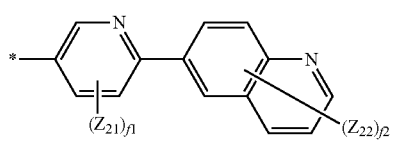
Formula 7-4
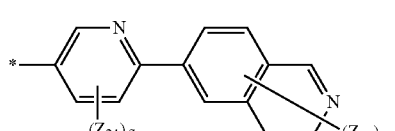
Formula 7-5
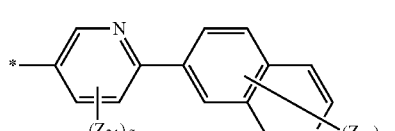
Formula 7-6
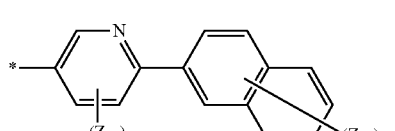
Formula 7-7
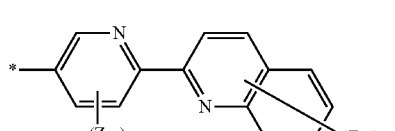
Formula 7-8
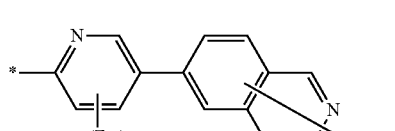
Formula 7-9
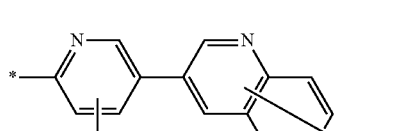
Formula 7-10
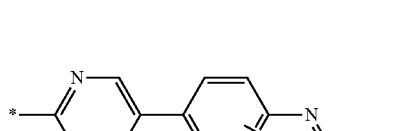
-continued
Formula 7-11
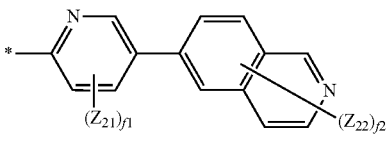
Formula 7-12
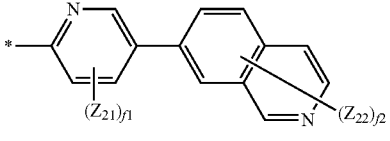
Formula 7-13
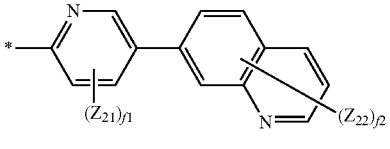
Formula 7-14
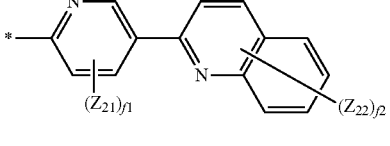
Formula 7-15
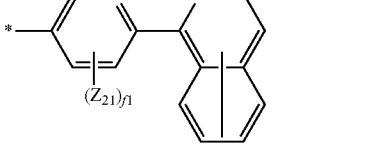
Formula 7-16
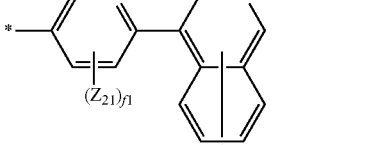
Formula 7-17
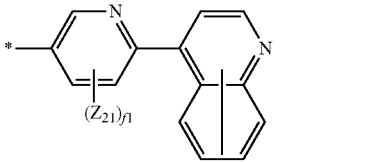
Formula 7-18
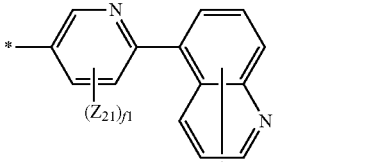

Formula 7-19 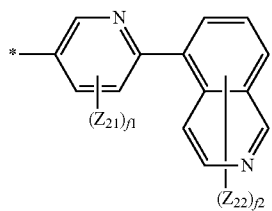
Formula 7-20 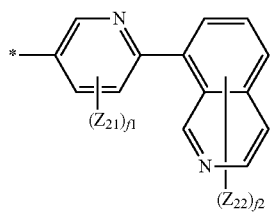
Formula 7-21 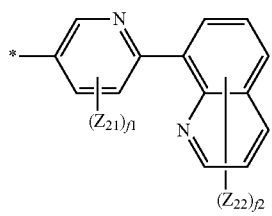
Formula 7-22 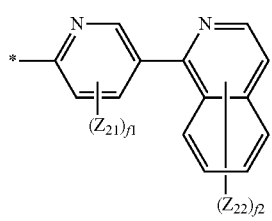
Formula 7-23 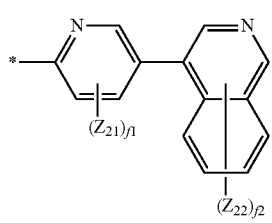
Formula 7-24 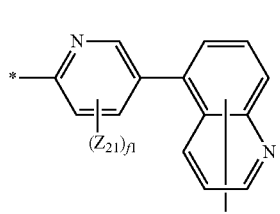
Formula 7-25 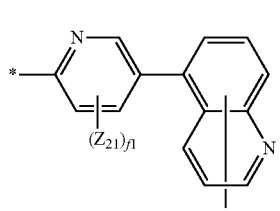
Formula 7-26 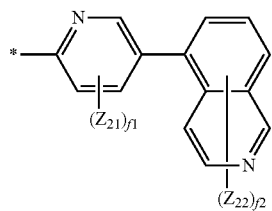
Formula 7-27 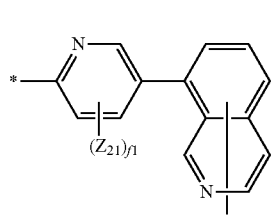
Formula 7-28 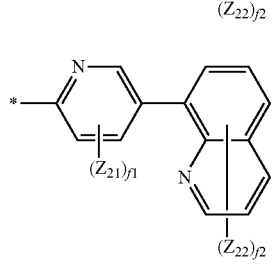
Formula 7-29 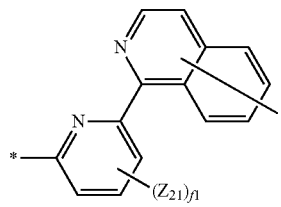
Formula 7-30 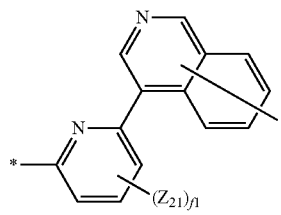
Formula 7-31 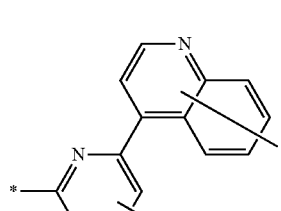
Formula 7-32 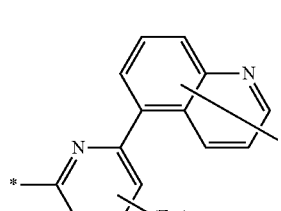

Formula 7-33
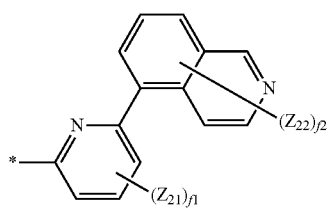
Formula 7-34
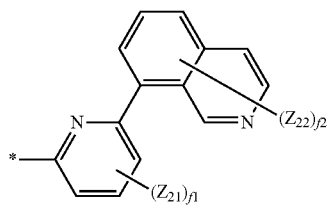
Formula 7-35
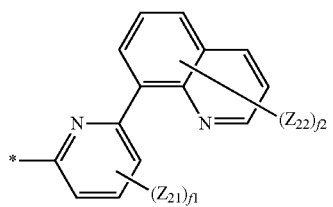
Formula 7-36
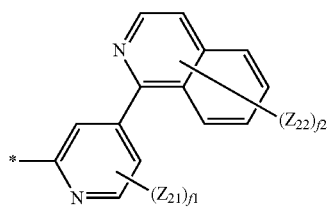
Formula 7-37
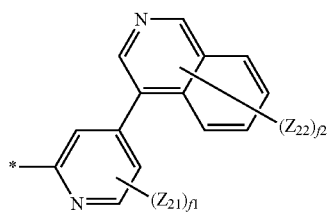
Formula 7-38
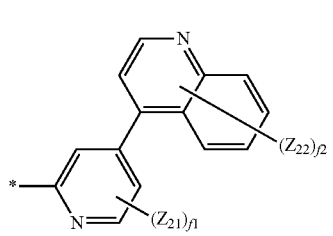
Formula 7-39
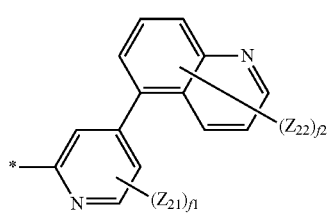
Formula 7-40
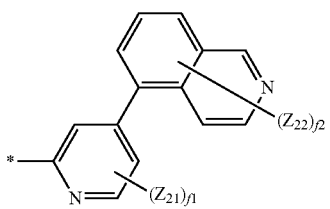
Formula 7-41
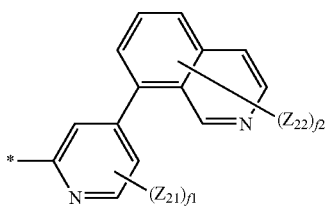
Formula 7-42
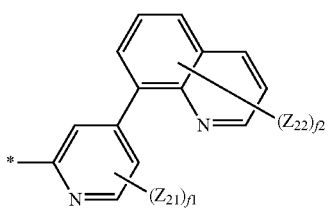
Formula 7-43
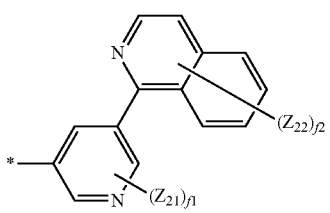
Formula 7-44
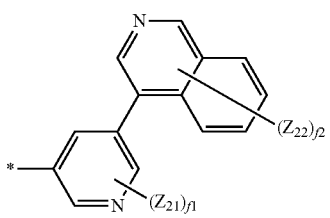
Formula 7-45
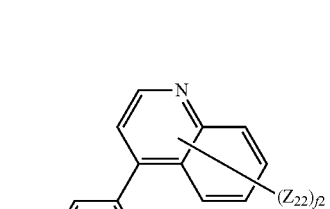
Formula 7-46
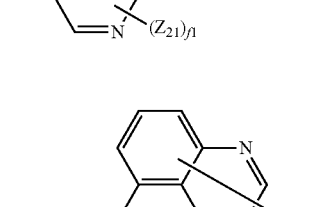

Formula 7-47
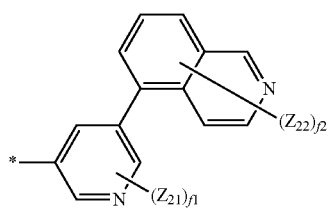
Formula 7-48
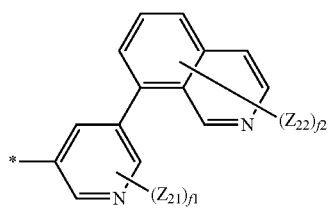
Formula 7-49
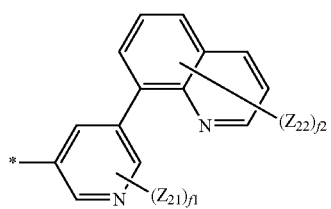
Formula 7-50
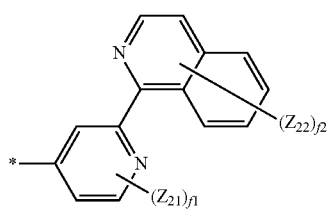
Formula 7-51
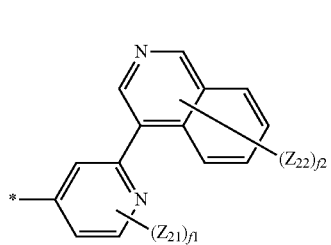
Formula 7-52
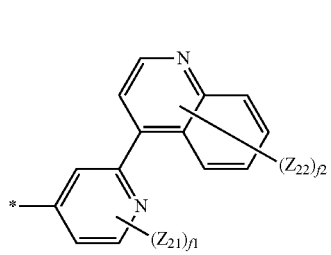
Formula 7-53
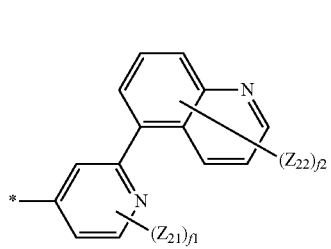
Formula 7-54
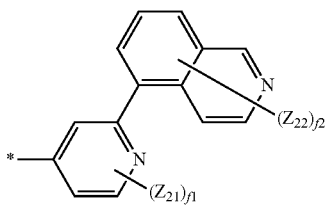
Formula 7-55
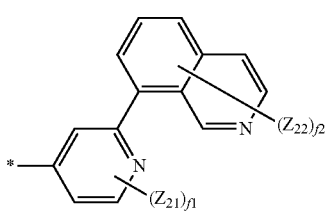
Formula 7-56
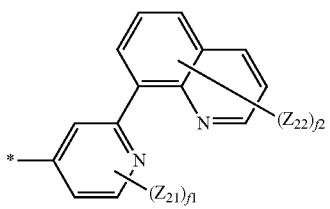
Formula 7-57
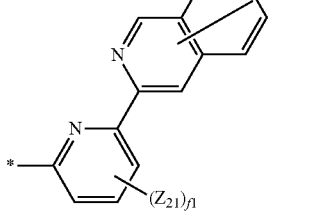
Formula 7-58
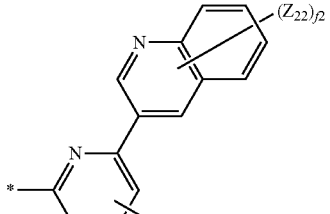
Formula 7-59
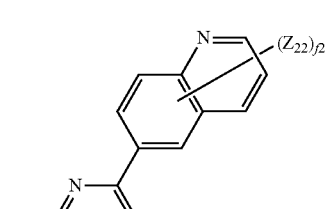
Formula 7-60
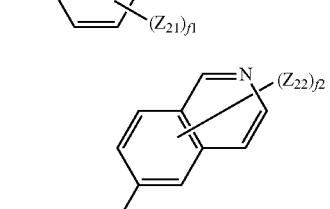

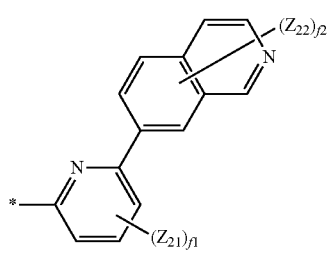
Formula 7-61
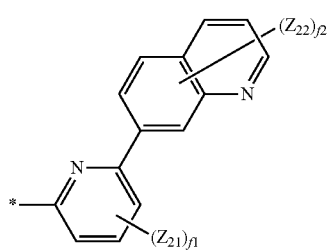
Formula 7-62
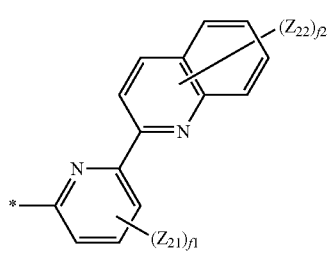
Formula 7-63
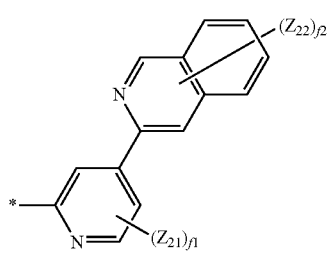
Formula 7-64
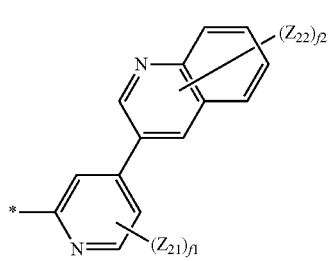
Formula 7-65
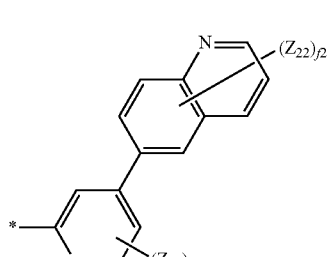
Formula 7-66
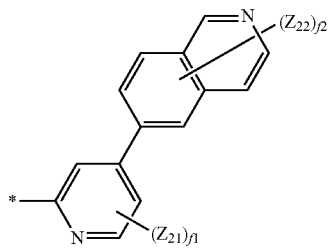
Formula 7-67
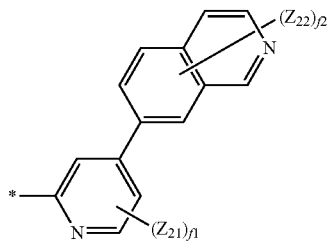
Formula 7-68
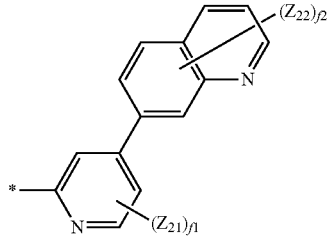
Formula 7-69
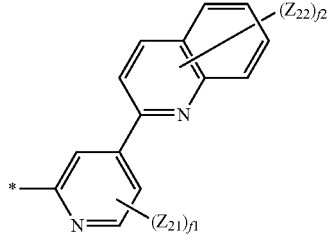
Formula 7-70
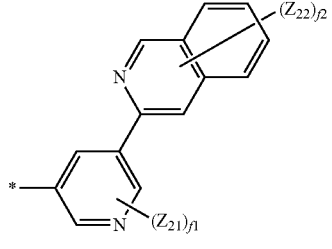
Formula 7-71
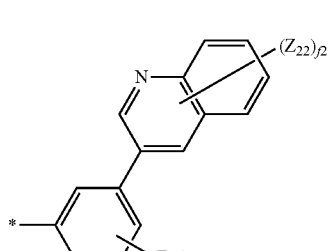
Formula 7-72

Formula 7-73
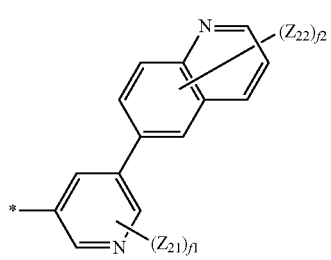
Formula 7-74
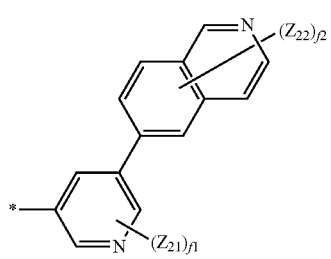
Formula 7-75
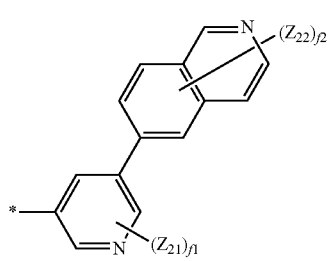
Formula 7-76
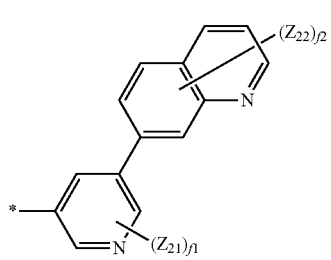
Formula 7-77
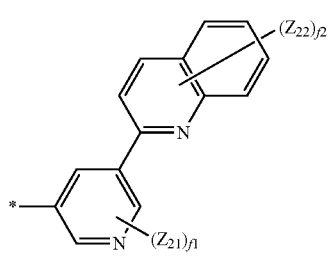
Formula 7-78
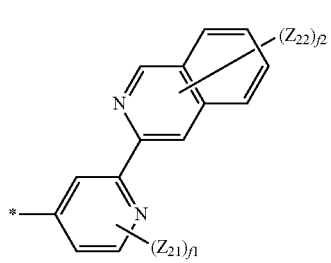
Formula 7-79
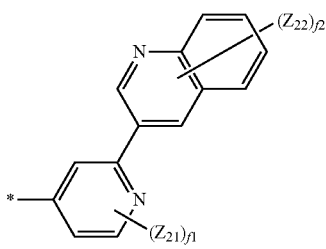
Formula 7-80
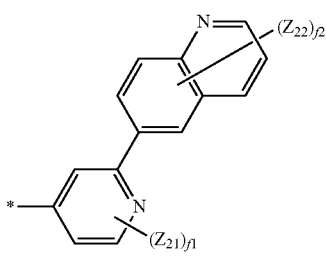
Formula 7-81
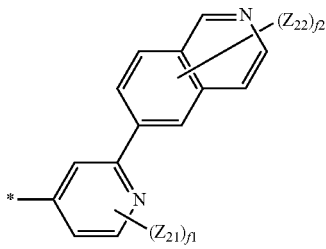
Formula 7-82
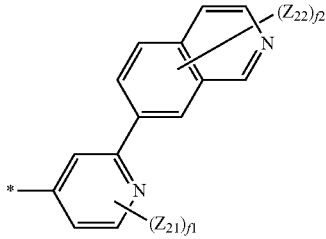
Formula 7-83
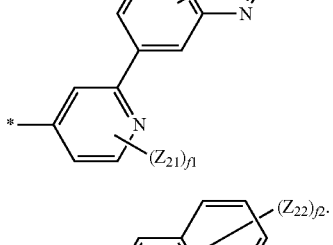
Formula 7-84
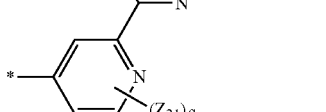
In Formulae 7-1 to 7-84,
$Z_{21}$ and $Z_{22}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, and —Si($Q_{31}$)($Q_{32}$)($Q_{33}$), where $Q_{31}$ to $Q_{33}$ may be each independently selected from a $C_1$-$C_{10}$ alkyl group, a $C_1$-$C_{10}$ alkoxy group, a phenyl group, and a naphthyl group, f1 may be an integer selected from 1, 2, and 3, f2 may be an integer selected from 1, 2, 3, 4, 5, and 6, and * indicates a binding site to a neighboring atom (e.g.,* represents a connection or bond to the remaining portion of Formula 1).

For example, $Z_{21}$ and $Z_{22}$ in Formulae 7-1 to 7-84 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group.

In Formula 1, b1 may be selected from 1, 2, and 3.

For example, b1 in Formula 1 may be 1.

$R_1$ to $R_4$, $R_{11}$ to $R_{17}$, and $R_{21}$ to $R_{27}$ in the above formulae may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted biphenyl group, a substituted or unsubstituted terphenyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_4$)($Q_5$), and —N($Q_6$)($Q_7$).

For example, $R_1$ to $R_4$, $R_{11}$ to $R_{17}$, and $R_{21}$ to $R_{27}$ in the above formulae may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, a biphenyl group, and a terphenyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, a biphenyl group, and a terphenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, a biphenyl group, a terphenyl group, and —Si($Q_{31}$)($Q_{32}$)($Q_{33}$); and —Si($Q_1$)($Q_2$)($Q_3$), where $Q_1$ to $Q_3$ and $Q_{31}$ to $Q_{33}$ may be each independently selected from a $C_1$-$C_{10}$ alkyl group, a $C_1$-$C_{10}$ alkoxy group, a phenyl group, and a naphthyl group.

In some embodiments, in the above formulae, $R_1$ to $R_4$ and $R_{11}$ to $R_{17}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a phenyl group, a naphthyl group, a pyridinyl group, a pyrimidinyl group, a triazinyl group, a biphenyl group, and a terphenyl group;

a phenyl group, a naphthyl group, a pyridinyl group, a pyrimidinyl group, a triazinyl group, a biphenyl group, and a terphenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and —Si($Q_{31}$)($Q_{32}$)($Q_{33}$); and —Si($Q_1$)($Q_2$)($Q_3$), and $R_{21}$ to $R_{27}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a phenyl group, a naphthyl group, a biphenyl group, and a terphenyl group;

a phenyl group, a naphthyl group, a biphenyl group, and a terphenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a biphenyl group, a terphenyl group, and —Si($Q_{31}$)($Q_{32}$)($Q_{33}$); and —Si($Q_1$)($Q_2$)($Q_3$), where $Q_1$ to $Q_3$ and $Q_{31}$ to $Q_{33}$ may be each independently selected from a $C_1$-$C_{10}$ alkyl group, a $C_1$-$C_{10}$ alkoxy group, a phenyl group, and a naphthyl group.

$R_{31}$ and $R_{32}$ in Formula 1 may be each independently selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted biphenyl group, a substituted or unsubstituted terphenyl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, $R_{31}$ and $R_{32}$ in Formula 1 may be each independently selected from:

a $C_1$-$C_{20}$ alkyl group and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a carbazolyl group, a dibenzofuranyl group, a dibenzothiophenyl group, a biphenyl group, and a terphenyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a carbazolyl group, a dibenzofuranyl group, a dibenzothiophenyl group, a biphenyl group, and a terphenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a carbazolyl group, a dibenzofuranyl group, a dibenzothiophenyl group, a biphenyl group, a terphenyl group, and —Si($Q_{31}$)($Q_{32}$)($Q_{33}$); and —Si($Q_1$)($Q_2$)($Q_3$), where $Q_1$ to $Q_3$ and $Q_{31}$ to $Q_{33}$ may be each independently selected from a $C_1$-$C_{10}$ alkyl group, a $C_1$-$C_{10}$ alkoxy group, a phenyl group, and a naphthyl group.

In some embodiments, $R_{31}$ and $R_{32}$ in Formula 1 may be each independently selected from:

a methyl group, an ethyl group, a propyl group, a butyl group, a pentyl group, a methoxy group, an ethoxy group, a propoxy group, a butoxy group, and a pentoxy group;

a phenyl group, a naphthyl group, a biphenyl group, and a terphenyl group;

a phenyl group, a naphthyl group, a biphenyl group, and a terphenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a biphenyl group, a terphenyl group, and —Si($Q_{31}$)($Q_{32}$)($Q_{33}$); and —Si($Q_1$)($Q_2$)($Q_3$), where $Q_1$ to $Q_3$ may be each independently selected from a $C_1$-$C_{10}$ alkyl group, a $C_1$-$C_{10}$ alkoxy group, a phenyl group, and a naphthyl group.

In the above formulae, $R_1$ to $R_4$ and $R_{11}$ to $R_{17}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —Si($Q_1$)($Q_2$)($Q_3$), and groups represented by Formulae 5-1 to 5-14, $R_{21}$ to $R_{27}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —Si($Q_1$)($Q_2$)($Q_3$), and groups represented by Formulae 5-1 to 5-5 and Formula 5-14, and $R_{31}$ and $R_{32}$ may be each independently selected from a $C_1$-$C_{10}$ alkyl group, a $C_1$-$C_{10}$ alkoxy group, and groups represented by Formulae 5-1 to 5-5 and Formula 5-14, where $Q_1$ to $Q_3$ may be each independently selected from a $C_1$-$C_{10}$ alkyl group, a $C_1$-$C_{10}$ alkoxy group, a phenyl group, and a naphthyl group, but embodiments are not limited thereto:

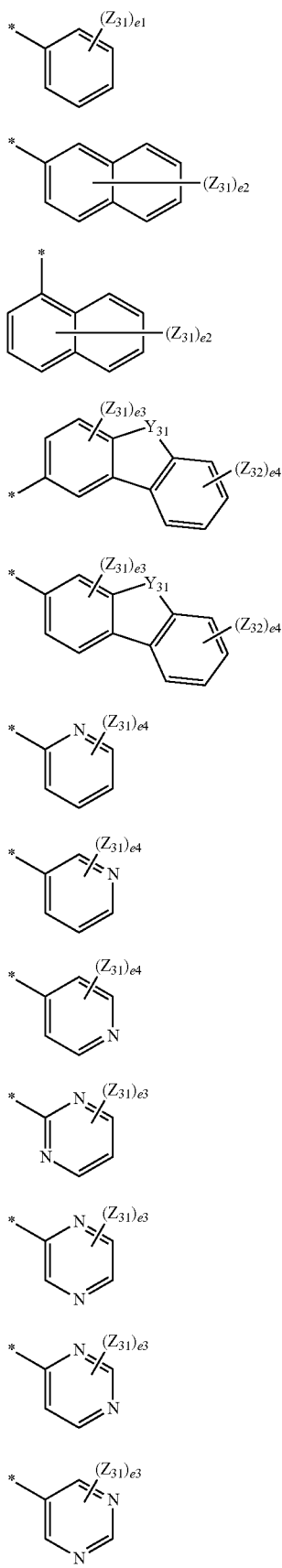

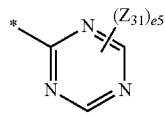

Formula 5-13

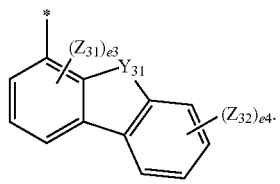

Formula 5-14

In Formulae 5-1 to 5-14, $Y_{31}$ may be selected from O, S, $C(Z_{33})(Z_{34})$, $N(Z_{35})$, and $Si(Z_{36})(Z_{37})$, $Z_{31}$ to $Z_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a biphenyl group, and a terphenyl group, e1 may be an integer selected from 1, 2, 3, 4, and 5, e2 may be an integer selected from 1, 2, 3, 4, 5, 6, and 7, e3 may be an integer selected from 1, 2, and 3, e4 may be an integer selected from 1, 2, 3, and 4, e5 may be 1 or 2, and * indicates a binding site to a neighboring atom (e.g., * represents a connection or bond to the remaining portion of Formula 1).

In some embodiments, in the above formulae, $R_1$ to $R_4$ and $R_{11}$ to $R_{17}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —$Si(Q_1)(Q_2)(Q_3)$, and groups represented by Formulae 6-1 to 6-29, $R_{21}$ to $R_{27}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —$Si(Q_1)(Q_2)(Q_3)$, and groups represented by Formulae 6-1 to 6-15 and Formulae 6-19 to 6-29, and $R_{31}$ and $R_{32}$ may be each independently selected from a $C_1$-$C_{20}$ alkyl group, a $C_1$-$C_{20}$ alkoxy group, and groups represented by Formulae 6-1 to 6-15 and Formulae 6-19 to 6-29, where $Q_1$ to $Q_3$ may be each independently selected from a $C_1$-$C_{10}$ alkyl group, a $C_1$-$C_{10}$ alkoxy group, a phenyl group, and a naphthyl group, but embodiments are not limited thereto:

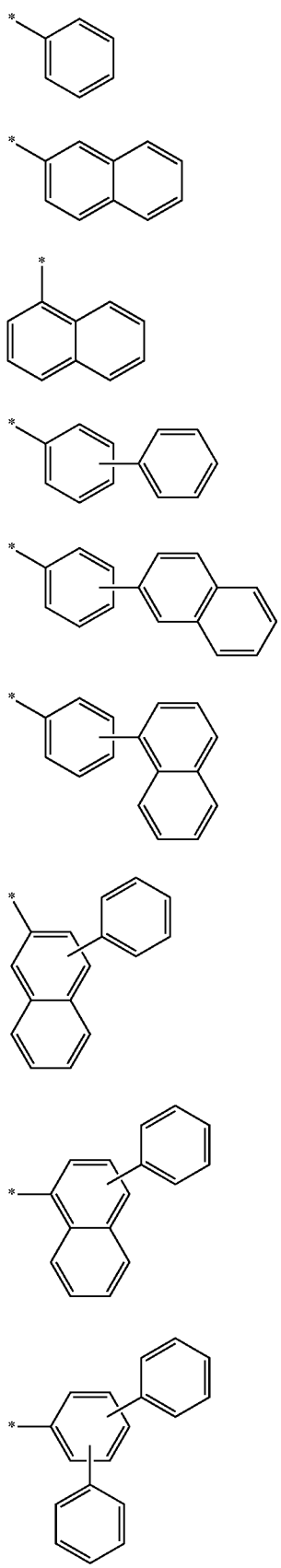
Formula 6-1
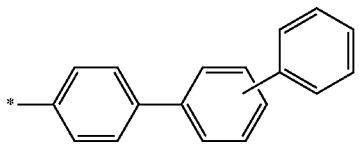
Formula 6-10
Formula 6-2
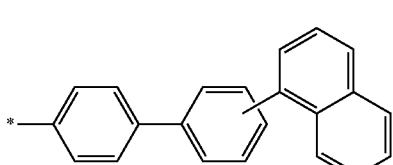
Formula 6-11
Formula 6-3
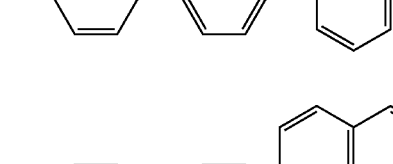
Formula 6-12
Formula 6-4
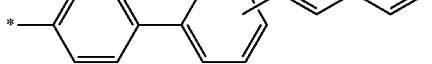
Formula 6-13
Formula 6-5
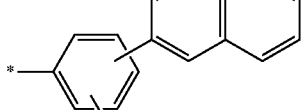
Formula 6-14
Formula 6-6
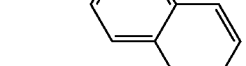
Formula 6-7
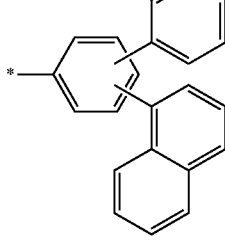
Formula 6-8
Formula 6-15
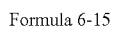
Formula 6-9
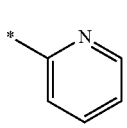
Formula 6-16
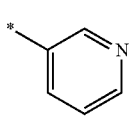
Formula 6-17

-continued

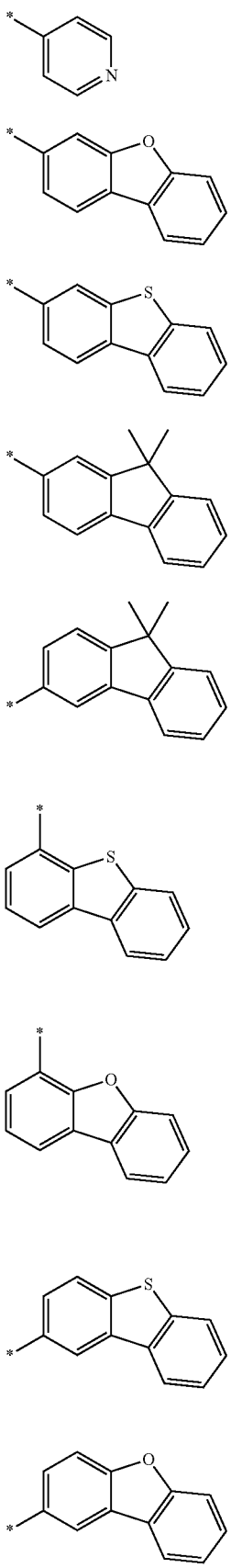

Formula 6-18

Formula 6-19

Formula 6-20

Formula 6-21

Formula 6-22

Formula 6-23

Formula 6-24

Formula 6-25

Formula 6-26

-continued

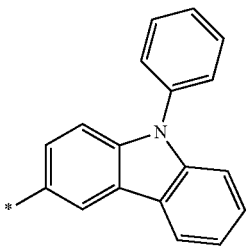
Formula 6-27

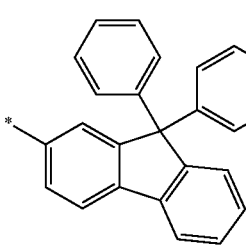
Formula 6-28

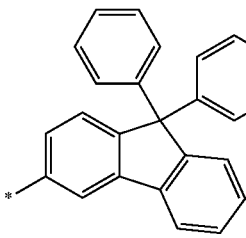
Formula 6-29

* in Formulae 6-1 to 6-29 indicates a binding site to a neighboring atom (e.g., * represents a connection or bond to the remaining portion of Formula 1).

For example, in the above formulae, $R_1$ to $R_4$, $R_{11}$ to $R_{17}$, and $R_{21}$ to $R_{27}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, $R_{31}$ and $R_{32}$ may be each independently selected from a $C_1$-$C_{20}$ alkyl group, a $C_1$-$C_{20}$ alkoxy group, and groups represented by Formulae 6-1 to 6-15, and $Q_1$ to $Q_3$ may be each independently selected from a $C_1$-$C_{10}$ alkyl group, a $C_1$-$C_{10}$ alkoxy group, a phenyl group, and a naphthyl group.

In some embodiments, in the above formulae, $R_1$ to $R_4$, $R_{11}$ to $R_{17}$, and $R_{21}$ to $R_{27}$ may be a hydrogen, and $R_{31}$ and $R_{32}$ may be each independently selected from a $C_1$-$C_{20}$ alkyl group and groups represented by Formulae 6-1 to 6-15.

In some embodiments, the condensed-cyclic compound may be represented by Formula 1-1 below:

Formula 1-1

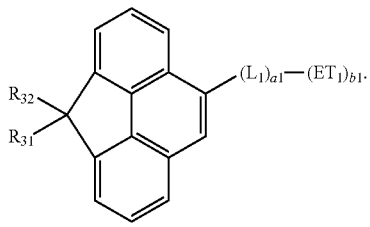

$L_1$, a1, $ET_1$, b1, $R_{31}$, and $R_{32}$ in Formula 1-1 may be understood by referring to the respective descriptions thereof provided herein. For example, $L_1$, a1, $ET_1$, b1, $R_{31}$, and $R_{32}$ in Formula 1-1 may be the same as the corresponding features in the preceding description.

In some embodiments, the condensed-cyclic compound may be represented by Formula 1(A) or 1(B):

Formula 1(A)

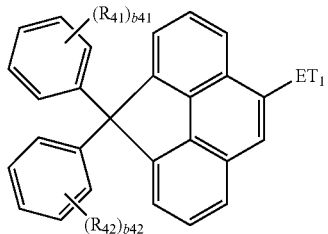

Formula 1(B)

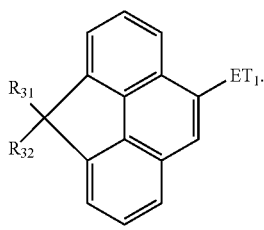

In Formulae 1(A) and 1(B), $ET_1$ is the same as described above, $R_{41}$ and $R_{42}$ may be understood by referring to the description of $R_1$ provided herein, b41 and b42 may be each independently an integer selected from 1, 2, 3, 4, and 5, and $R_{31}$ and $R_{32}$ may be each independently selected from a $C_1$-$C_{20}$ alkyl group and a $C_1$-$C_{20}$ alkoxy group. For example, in Formulae 1(A) and 1(B), $ET_1$ may be the same as $ET_1$ in the preceding description, and $R_{41}$ and $R_{42}$ may be the same as $R_1$ in the preceding description.

The condensed-cyclic compound represented by Formula 1 may be selected from Compounds 1 to 7, but the condensed-cyclic compound is not limited thereto:

1

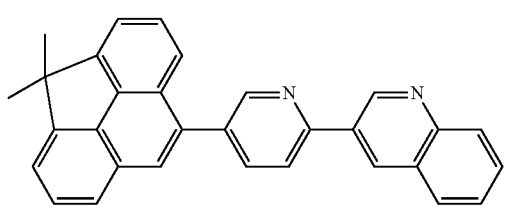

2

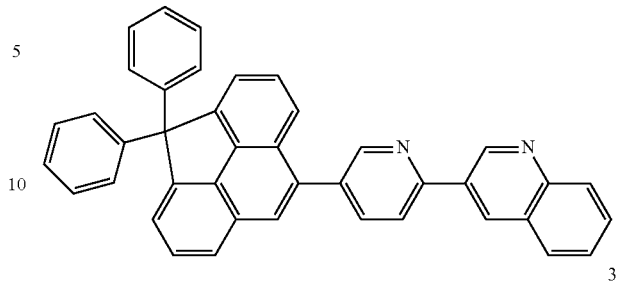

3

4

5

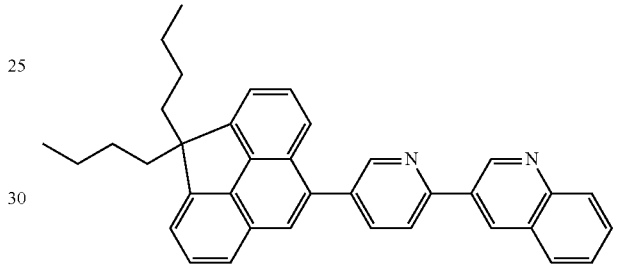

6

7

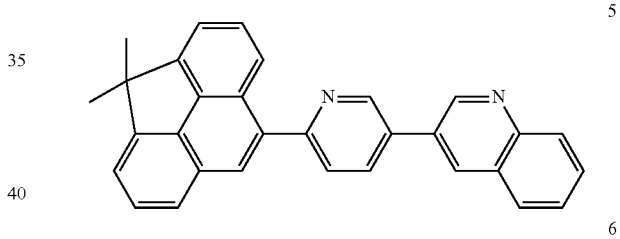

The condensed-cyclic compound represented by Formula 1 has a cyclopentaphenanthrene (CP) core represented by Formula 1' below, where an $ET_1$ group is substituted at Carbon B.

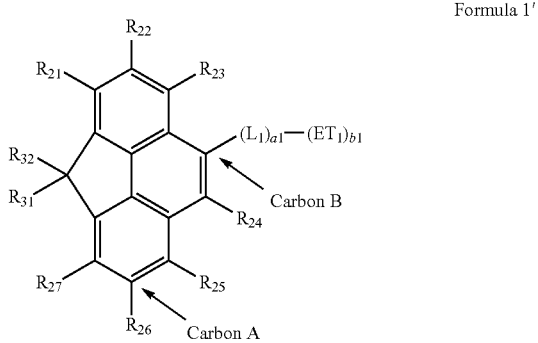

Formula 1'

According to molecular modeling of embodiments of the condensed-cyclic compound, carbon reactivity and physical properties of CP may be different depending on the position of a substituent (e.g., substitution at Carbon A and/or Carbon B of CP).

Although the present disclosure is not limited to a particular mechanism or theory, as a benzene ring containing Carbon A of CP has a carbon-carbon bond length that is almost the same as that of benzene generally, and has delocalized atomic charges, it is believed that the aromaticity of the benzene ring containing Carbon A is substantially the same as, or no different from, that of the typical benzene (e.g., the benzene molecule itself).

However, a benzene ring containing Carbon B of CP has a carbon-carbon bond length (e.g., 1.418 Å) that is greater than a general carbon-carbon double bond length (1.34 Å) or a carbon-carbon double bond length (1.39 Å) of benzene, and has localized atomic charges. It is believed that the reason for the greater carbon-carbon bond length of the benzene ring containing Carbon B of CP is that carbon-carbon bonds of the benzene ring containing Carbon B in CP are more strained than those of phenanthrene. Accordingly, it is believed that the aromaticity of the benzene ring containing Carbon B is relatively less than that of the benzene ring containing Carbon A, and consequently, chemical reactivity of the benzene ring containing Carbon B is relatively greater than that of the benzene ring containing Carbon A. For example, it is believed that the benzene ring containing Carbon B has less aromaticity than the benzene ring containing Carbon A.

Comparing CP with perylene, in the case of perylene, only benzene rings are fused together. Accordingly, every benzene ring of perylene is not strained. However, in the case of CP, the benzene ring containing Carbon B is greatly strained due to a pentagon ring (a ring having a pentagonal or generally pentagonal shape) adjacent to the benzene ring containing Carbon B. Accordingly, when Carbon B is open (for example, unsubstituted), Carbon B of CP in an electromagnetic field may be easily attacked by a substituent, leading to the manufacture of a device that has unstability (is unstable) due to radicalization or deterioration. For example, when Carbon B of CP is unsubstituted, CP is susceptible to attack at Carbon B due to the relatively lower aromaticity of the benzene ring containing Carbon B, and thus, CP in which Carbon B of CP is unsubstituted is relatively unstable as compared to a condensed-cyclic compound including CP substituted at Carbon B as described with respect to embodiments of the present disclosure.

According to embodiments of the present disclosure, due to the substitution of an $ET_1$ group at Carbon B of CP, a material that is electrochemically sturdy and has excellent durability may be provided.

The condensed-cyclic compound represented by Formula 1 may be synthesized by using any suitable organic synthetic method available in the art. In view of the description herein, a synthesis method of the condensed-cyclic compound should be readily recognized by one of ordinary skill in the art.

The condensed-cyclic compound represented by Formula 1 may be used between a pair of electrodes of an organic light-emitting device. For example, the condensed-cyclic compound may be included in an electron transport region of the organic light-emitting device, for example, in an electron transport layer. Accordingly, an organic light-emitting device according to an embodiment includes a first electrode, a second electrode facing the first electrode, and an organic layer between the first electrode and the second electrode and including an emission layer, where the organic layer includes at least one condensed-cyclic compound represented by Formula 1.

The statement "(for example, the organic layer) includes at least one condensed-cyclic compound," as used herein, may be interpreted as "(the organic layer) includes one of the condensed-cyclic compounds represented by Formula 1 or at least two different condensed-cyclic compounds represented by Formula 1."

For example, the organic layer may include only Compound 1 as the condensed-cyclic compound. In some embodiments, Compound 1 may be present in the electron transport layer of the organic light-emitting device. In some embodiments, the organic layer may include Compound 1 and Compound 2 as the condensed-cyclic compounds. For example, Compound 1 and Compound 2 may be present in the same layer (for example, both of Compound 1 and Compound 2 may be present in the electron transport layer) or may be present in different layers (for example, Compound 1 may be present in the emission layer and Compound 2 may be present in the electron transport layer).

The organic layer may include i) a hole transport region between the first electrode (e.g., an anode) and the emission layer, the hole transport region including at least one selected from a hole injection layer, a hole transport layer, a buffer layer, and an electron blocking layer, and ii) an electron transport region between the emission layer and the second electrode (e.g., a cathode), the electron transport region including at least one selected from a hole blocking layer, an electron transport layer, and an electron injection layer. The electron transport region may include at least one of the condensed-cyclic compounds represented by Formula 1. For example, the electron transport region may include the electron transport layer, and the electron transport layer may include at least one of the condensed-cyclic compounds represented by Formula 1.

The term "organic layer," as used herein, refers to a single layer and/or a plurality of layers disposed between the first electrode and the second electrode of the organic light-emitting device. A material included in the "organic layer," however, is not limited to an organic material. For example, the organic layer may include inorganic materials.

The accompanying drawing is a schematic cross-sectional view of an organic light-emitting device 10 according to an embodiment. The organic light-emitting device 10 includes a first electrode 110, an organic layer 150, and a second electrode 190.

Hereinafter, the structure of an organic light-emitting device according to an embodiment and a method of manufacturing an organic light-emitting device according to an embodiment will be described with reference to the accompanying drawing.

In the accompanying drawing, a substrate may be additionally disposed under the first electrode 110 or on the second electrode 190. The substrate may be a glass or transparent plastic substrate having excellent mechanical strength, thermal stability, transparency, surface smoothness, ease of handling, and water-resistance.

For example, the first electrode 110 may be formed by depositing or sputtering a material for forming the first electrode on the substrate. When the first electrode 110 is an anode, the material for forming the first electrode may be selected from materials having a high work function to facilitate hole injection. The first electrode 110 may be a reflective electrode, a semi-transmissive electrode, or a transmissive electrode. The material for forming a first electrode may be a transparent and highly conductive material, examples of which include indium tin oxide (ITO), indium zinc oxide (IZO), tin oxide ($SnO_2$), and zinc oxide (ZnO). In some embodiments, in order to form the first electrode 110 to be a semi-transmissive electrode or a reflective electrode, at least one selected from magnesium (Mg), aluminum (Al), aluminum-lithium (Al—Li), calcium (Ca), magnesium-indium (Mg—In), and magnesium-silver (Mg—Ag) may be used as the material for forming the first electrode.

The first electrode 110 may have a single-layer structure, or a multi-layer structure including two or more layers. For example, the first electrode 110 may have a three-layered structure of ITO/Ag/ITO, but the structure of the first electrode 110 is not limited thereto.

The organic layer 150 is disposed on the first electrode 110. The organic layer 150 may include an emission layer.

The organic layer 150 may further include a hole transport region disposed between the first electrode 110 and the emission layer, and an electron transport region disposed between the emission layer and the second electrode 190.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL). However, the hole transport region and the electron transport region are not limited thereto.

The hole transport region may have a single-layer structure formed of a single (or sole) material, a single-layer structure formed of a plurality of different materials, or a multi-layer structure having a plurality of layers formed of a plurality of different materials.

For example, the hole transport region may have a single-layer structure formed of a plurality of different materials or may have a structure of HIL/HTL, a structure of HIL/HTL/buffer layer, a structure of HIL/buffer layer, a structure of HTL/buffer layer, or a structure of HIL/HTL/EBL, where layers of each structure are sequentially stacked from the first electrode 110 in the stated order. However, the structure of the hole transport region is not limited thereto.

When the hole transport region includes an HIL, the HIL may be formed on the first electrode 110 by using various suitable methods, such as vacuum deposition, spin coating, casting, an Langmuir-Blodgett (LB) method, inkjet printing, laser printing, or laser induced thermal imaging (LITI).

When the HIL is formed by vacuum deposition, the vacuum deposition, for example, may be performed at a deposition temperature of about 100 to about 500° C., at a vacuum degree (e.g., vacuum level or pressure) of about $10^{-8}$ to about $10^{-3}$ torr, and at a deposition rate of about 0.01 to about 100 Å/sec in consideration of a compound for an HIL to be deposited (e.g., in consideration of the features of the compound used to form the HIL) and the structure of the HIL to be formed.

When the HIL is formed by spin coating, the spin coating may be performed at a coating rate of about 2000 rpm to about 5000 rpm and at a heat treatment temperature of about 80° C. to 200° C. in consideration of a compound for the HIL to be deposited (e.g., in consideration of the features of the compound used to form the HIL) and the structure of the HIL to be formed.

When the hole transport region includes an HTL, the HTL may be formed on the first electrode 110 or on the HIL by using various suitable methods, such as vacuum deposition, spin coating, casting, an LB method, inkjet printing, laser printing, or LITI. When the HTL is formed by vacuum deposition or spin coating, deposition and coating conditions for the HTL may be determined by referring to the deposition and coating conditions described with respect to the HIL.

The hole transport region may include at least one selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), (polyaniline)/poly(4-styrenesulfonate) (PANI/PSS), a compound represented by Formula 201, and a compound represented by Formula 202:

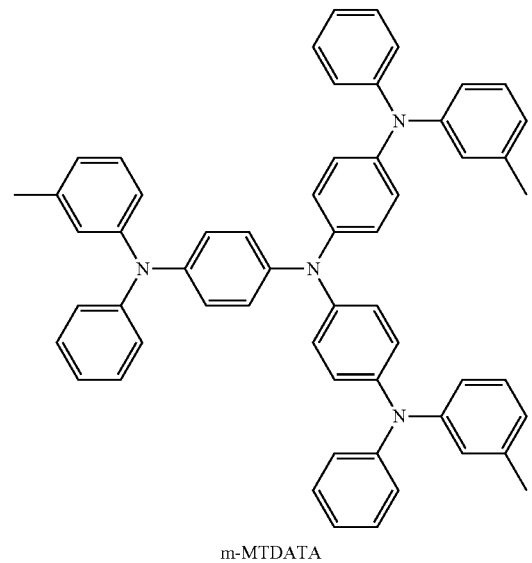

m-MTDATA

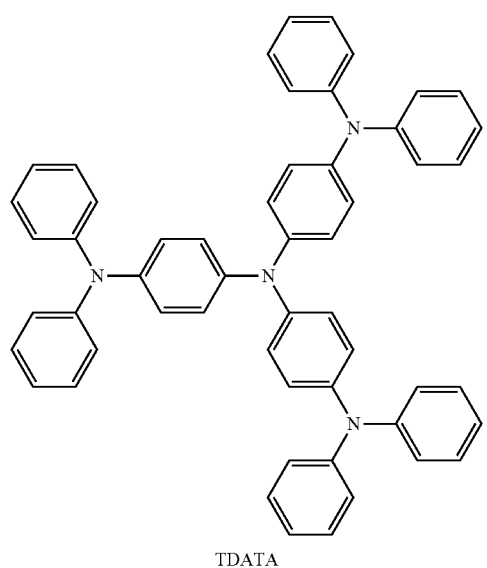
TDATA
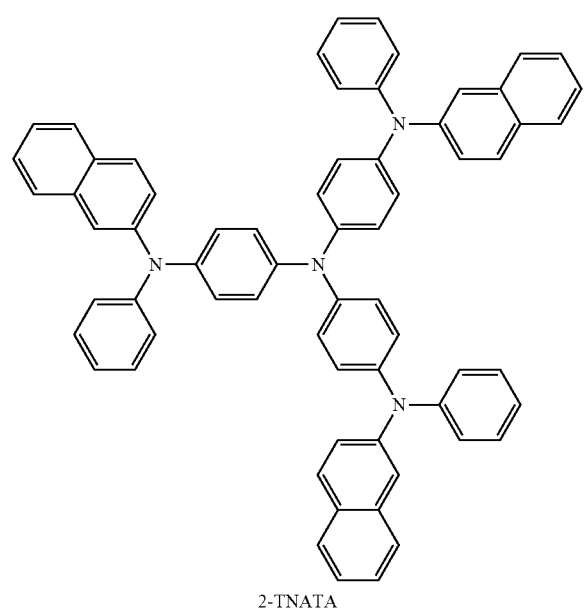
2-TNATA
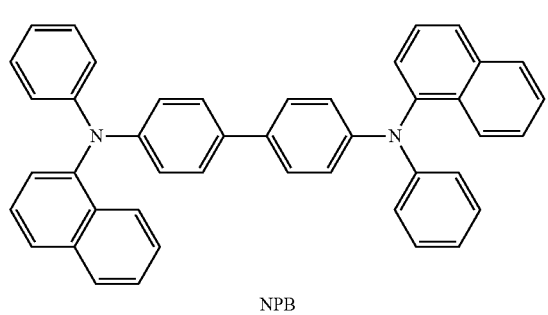
NPB
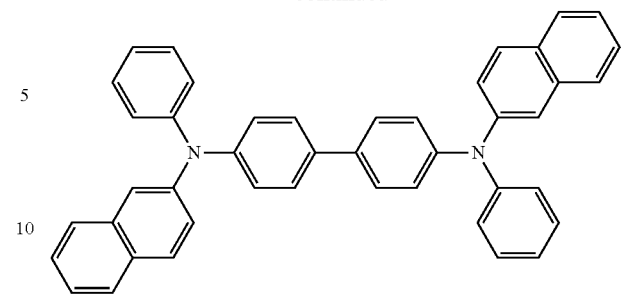
β-NPB
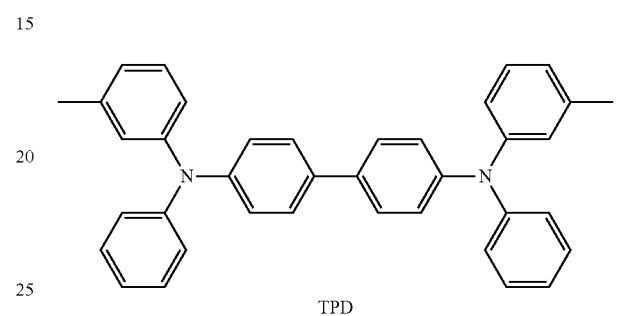
TPD
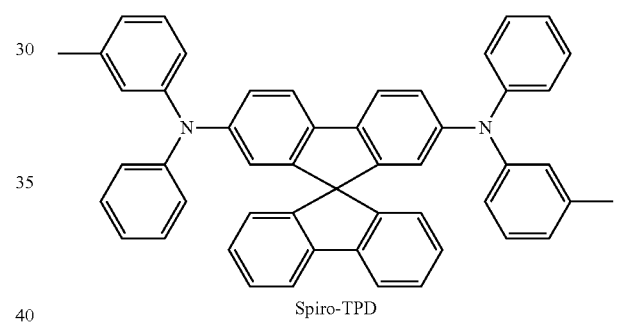
Spiro-TPD
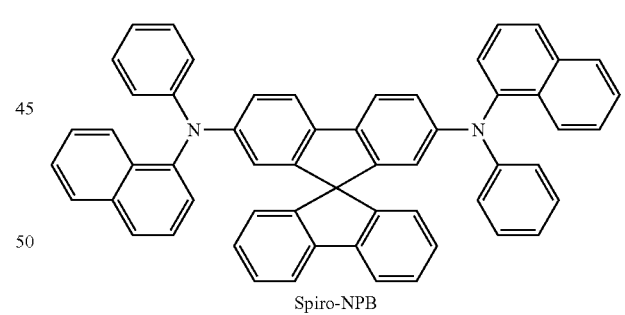
Spiro-NPB
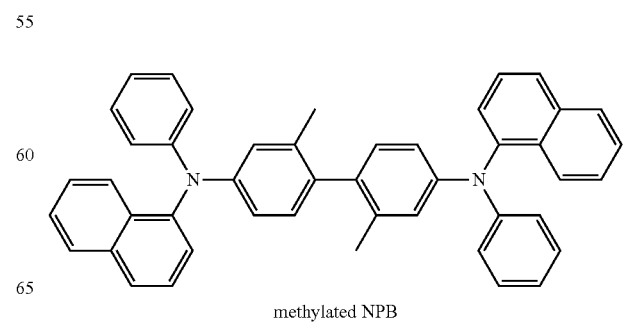
methylated NPB -continued

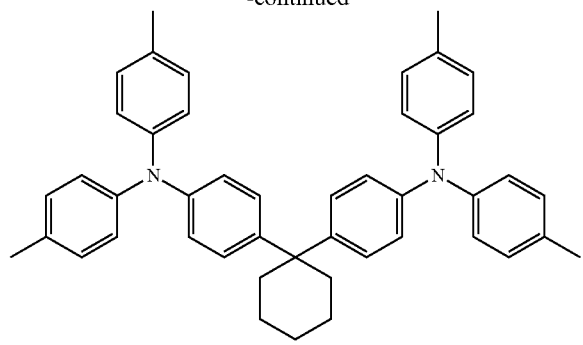

TAPC

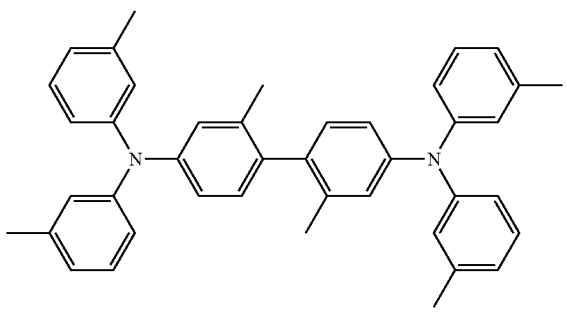

HMTPD

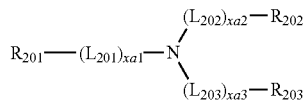

Formula 201

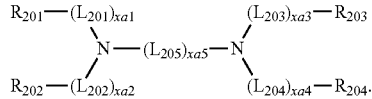

Formula 202

In Formulae 201 and 202, $L_{201}$ to $L_{205}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may be each independently selected from 0, 1, 2, and 3, xa5 may be selected from 1, 2, 3, 4, and 5, and $R_{201}$ to $R_{204}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formulae 201 and 202, $L_{201}$ to $L_{205}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, xa1 to xa4 may be each independently 0, 1, or 2, xa5 may be 1, 2, or 3, and $R_{201}$ to $R_{204}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group. However, the compounds respectively represented by Formulae 201 and 202 are not limited thereto.

The compound represented by Formula 201 may be represented by Formula 201A:

Formula 201A

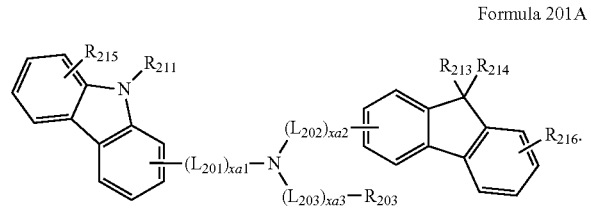

For example, the compound represented by Formula 201 may be represented by Formula 201A-1, but the compound is not limited thereto:

Formula 201A-1

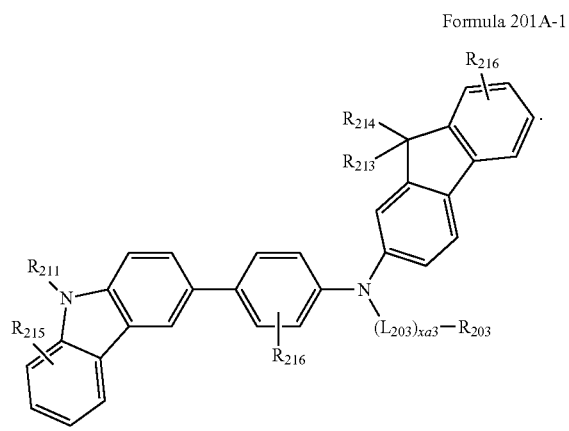

The compound represented by Formula 202 may be represented by Formula 202A, but the compound is not limited thereto:

Formula 202A

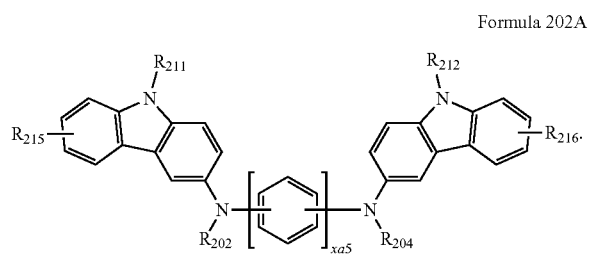

In Formulae 201A, 201A-1, and 202A, $L_{201}$ to $L_{203}$, xa1 to xa3, xa5, and $R_{202}$ to $R_{204}$ may be understood by referring to the descriptions thereof provided herein (e.g., $L_{201}$ to $L_{203}$, xa1 to xa3, xa5, and $R_{202}$ to $R_{204}$ may be the same as those described with respect to Formulae 201 and 202), $R_{211}$ and $R_{212}$ may be understood by referring to the description of $R_{203}$ provided herein (e.g., $R_{211}$ and $R_{212}$ may be the same as described with respect to $R_{201}$ to $R_{204}$ of Formulae 201 and 202), and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

For example, in Formulae 201A, 201A-1, and 202A, $L_{201}$ to $L_{203}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xa1 to xa3 may be each independently 0 or 1, $R_{203}$, $R_{211}$, and $R_{212}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

In some embodiments, $R_{213}$ and $R_{214}$ may be each independently selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, $R_{215}$ and $R_{216}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and xa5 may be 1 or 2.

In some embodiments, $R_{213}$ and $R_{214}$ in Formulae 201A and 201A-1 may bind to each other (e.g., combine together) to form a saturated or unsaturated ring.

The compound represented by Formula 201 and the compound represented by Formula 202 may each independently include at least one compound selected from Compounds HT1 to HT20, but the compounds are not limited thereto.

HT1

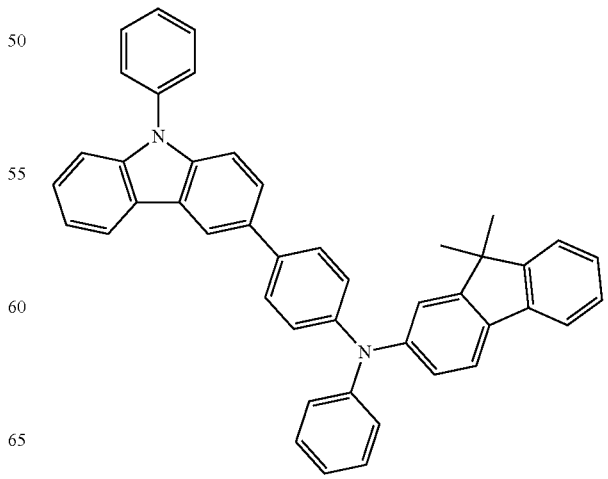

HT2
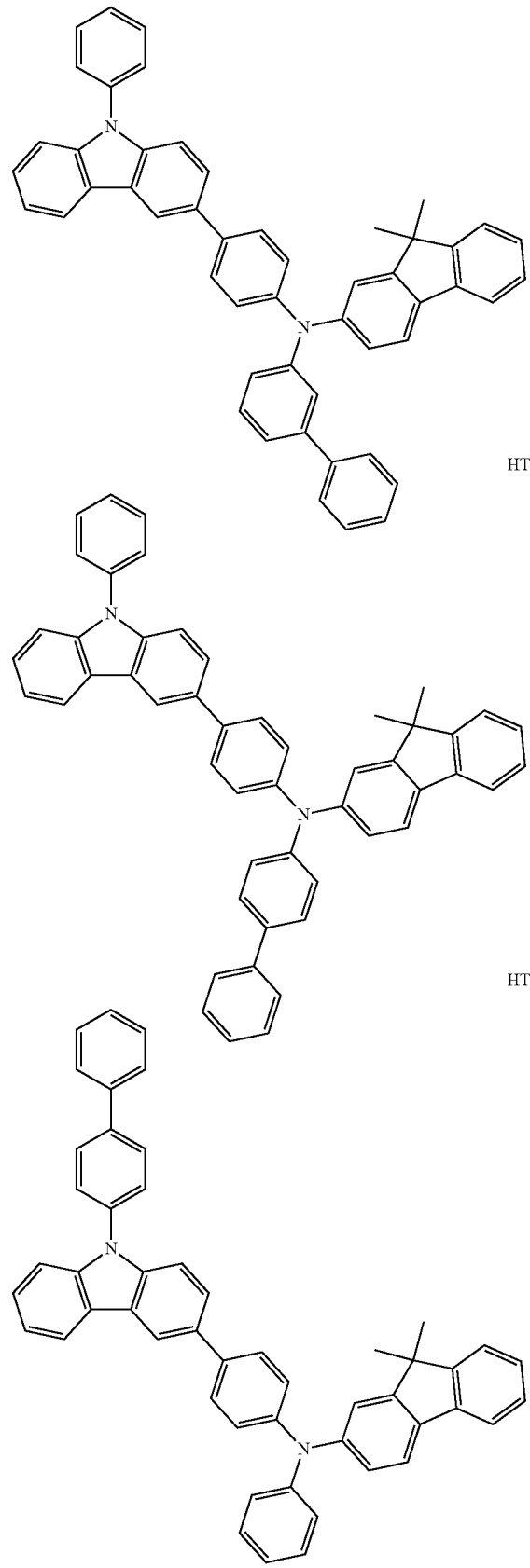
HT3
HT4
HT5
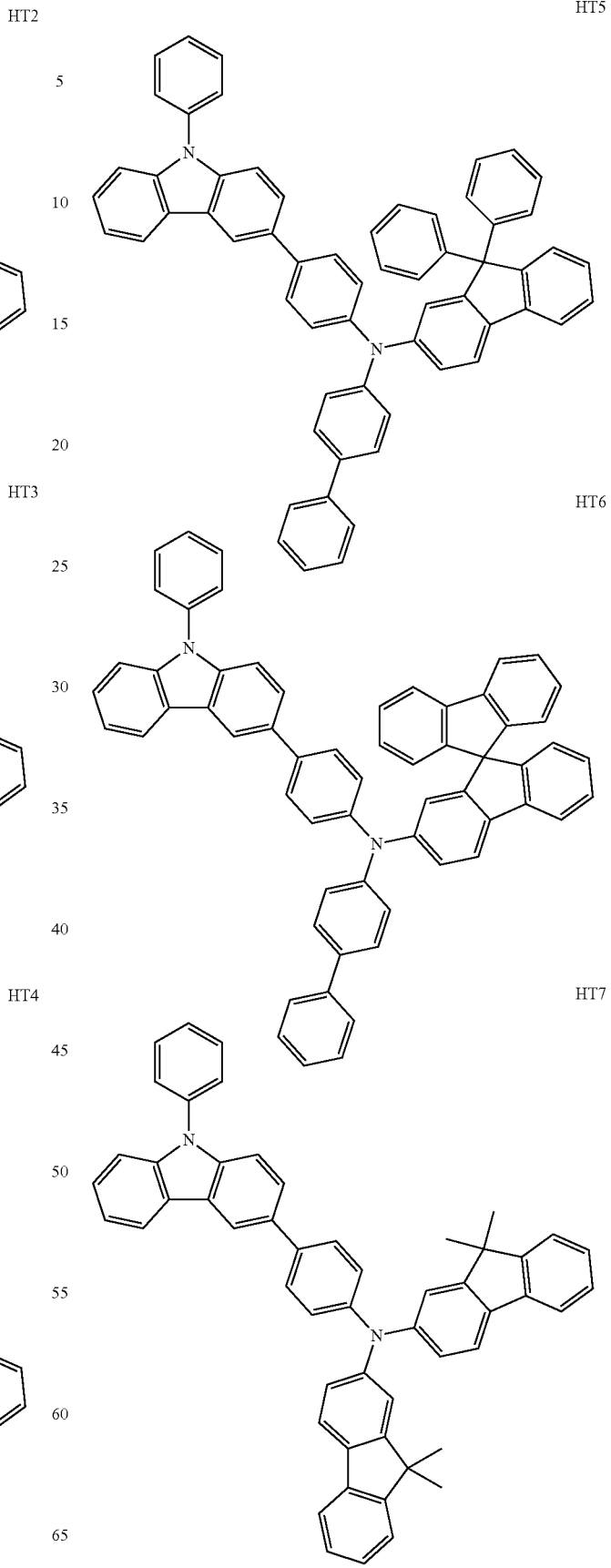
HT6
HT7

HT8
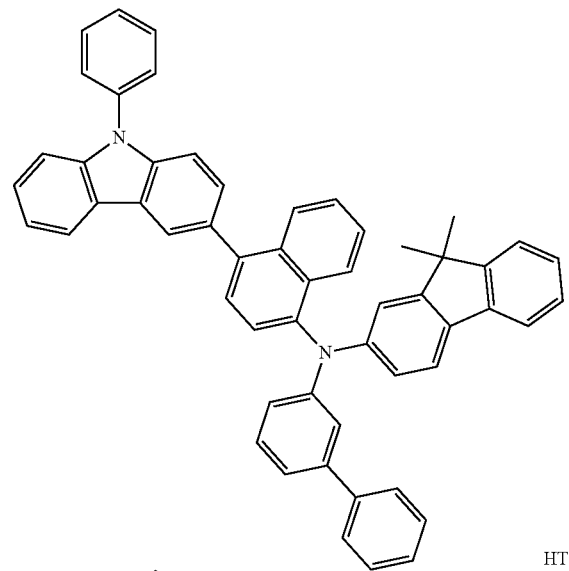
HT11
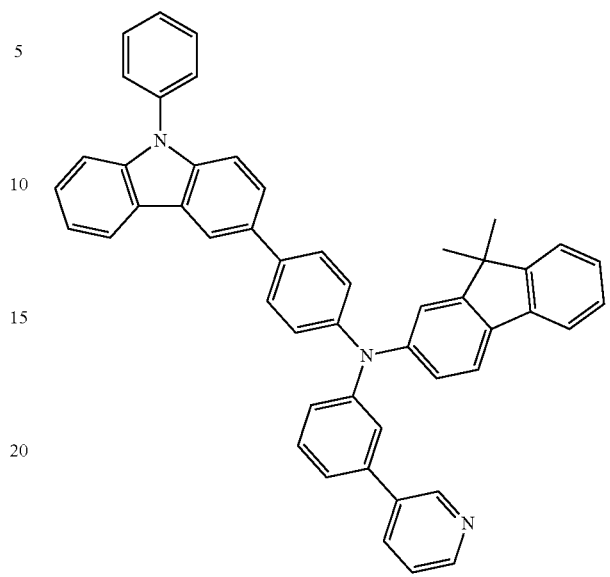
HT9
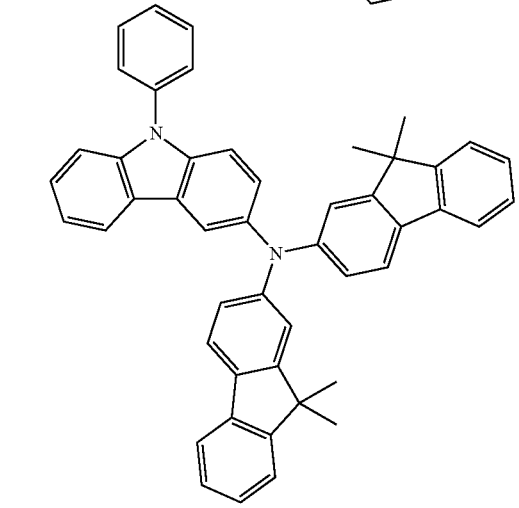
HT12
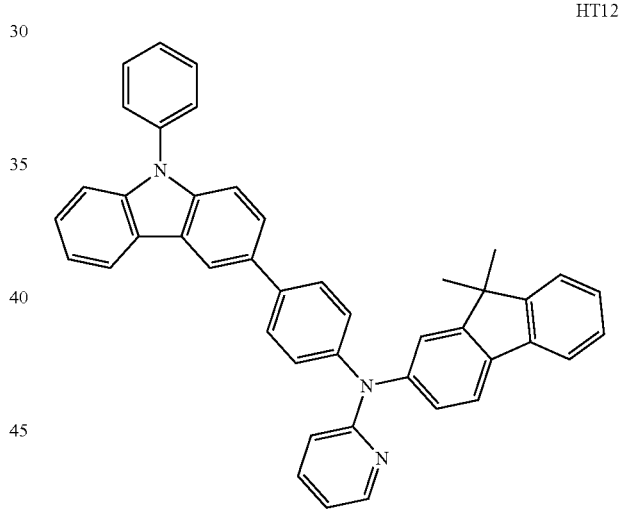
HT10
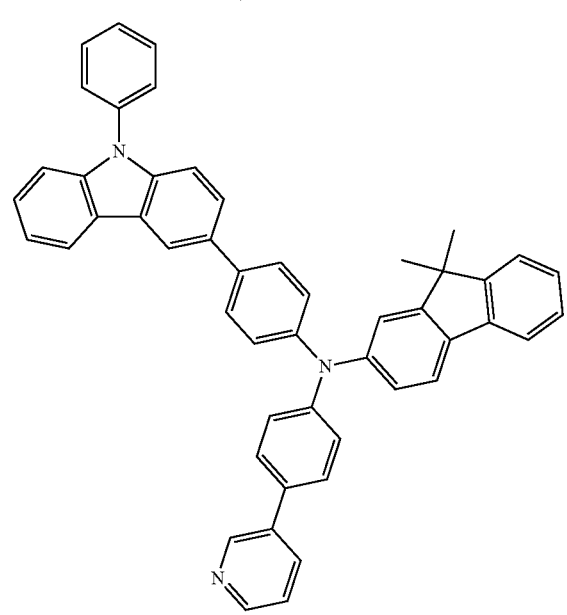
HT13
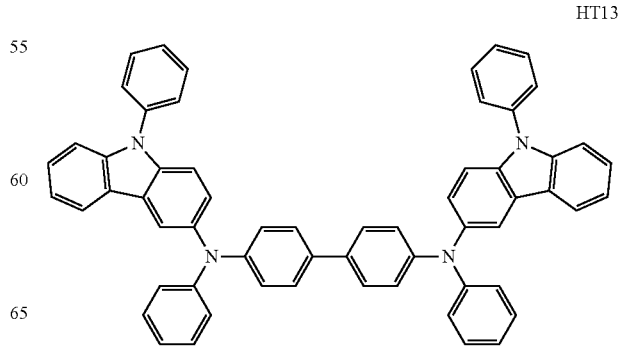

HT14
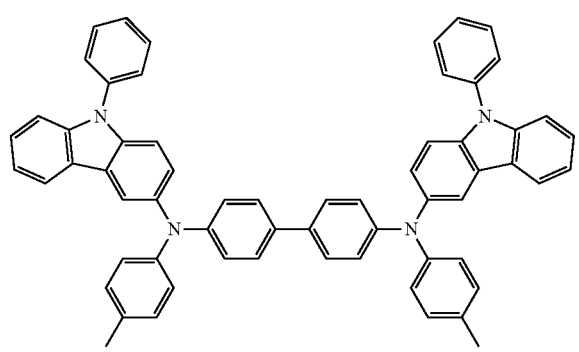

HT15
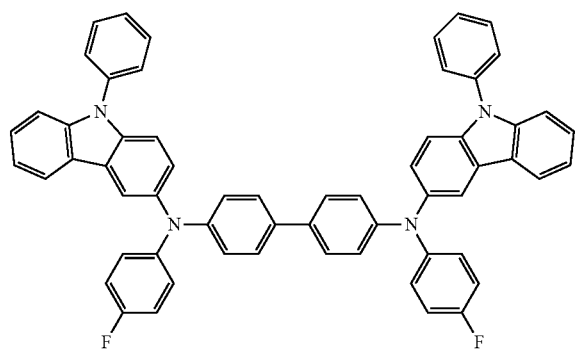

HT16
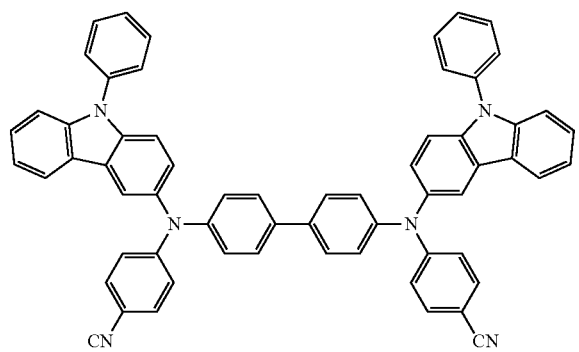

HT17
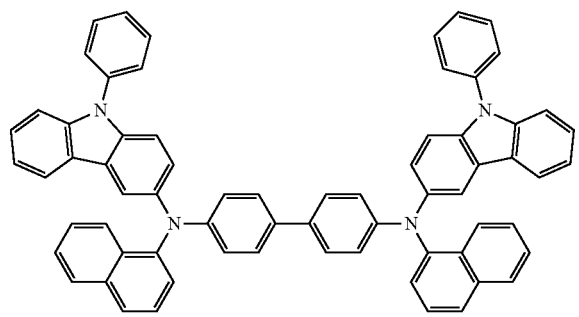

HT18
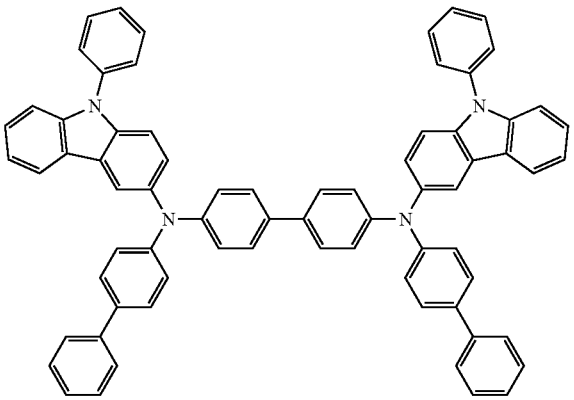

HT19
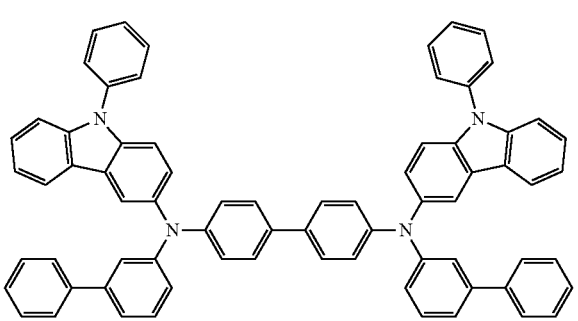

HT20
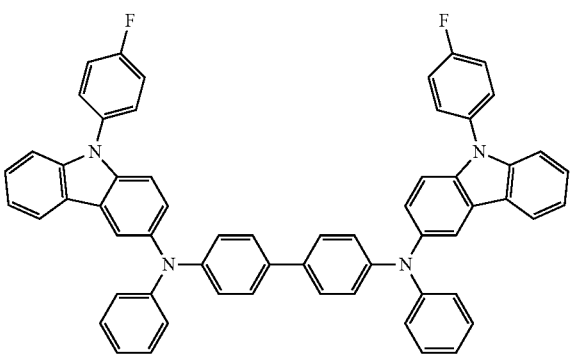

A thickness of the hole transport region may be in a range from about 100 Å to about 10000 Å, for example, from about 100 Å to about 1000 Å. When the hole transport region includes an HIL and an HTL, a thickness of the HIL may be in a range from about 100 Å to about 10000 Å, for example, from about 100 Å to about 1000 Å, and a thickness of the HTL may be in a range from about 50 Å to about 2000 Å, for example, from about 100 Å to about 1500 Å. When the thicknesses of the hole transport region, the HIL, and the HTL are within any of the foregoing ranges, satisfactory or suitable hole transport characteristics may be obtained without a substantial increase in driving voltage.

The hole transport region may further include, in addition to a material as described above, a charge-generation material for the improvement of conductive properties. The charge-generation material may be homogeneously or unhomogeneously (e.g., inhomogeneously or heterogeneously) dispersed in the hole transport region.

The charge-generation material may include, for example, a p-dopant. The p-dopant may include one of a quinone derivative, a metal oxide, and/or a cyano group-containing compound, but the p-dopant is not limited thereto. For example, non-limiting examples of the p-dopant include a quinone derivative such as tetracyanoquinonedimethane (TCNQ) or 2,3,5,6-tetrafluoro-tetracyano-1,4-benzoquinonedimethane (F4-TCNQ), a metal oxide such as a tungsten oxide or a molybdenum oxide, and Compound HT-D1, but the p-dopant is not limited thereto.

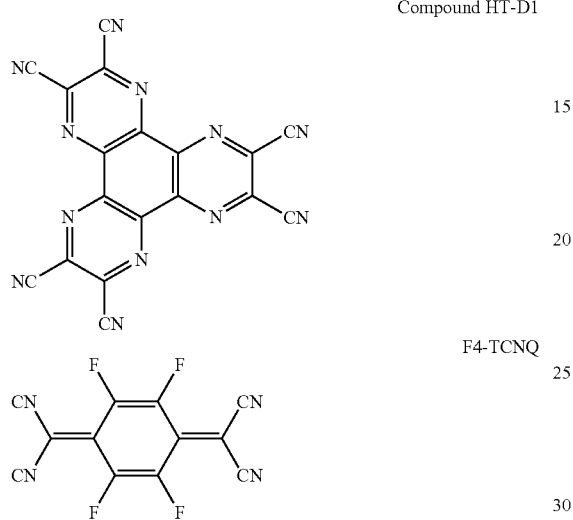

Compound HT-D1

F4-TCNQ

The hole transport region may further include, in addition to an HIL and an HTL as described above, at least one selected from a buffer layer and an EBL. The buffer layer may compensate for an optical resonance distance according to a wavelength of light emitted from the emission layer, thereby improving the light-emission efficiency of a formed organic light-emitting device. For use as a material included in the buffer layer, a material that may be included in the hole transport region (e.g., a material described herein with respect to the hole transport region) may be used. The EBL prevents or reduces injection of electrons from the electron transport region.

The emission layer may be formed on the first electrode 110 or on the hole transport region by using various suitable methods such as vacuum deposition, spin coating, casting, an LB method, inkjet printing, laser printing, or LITI. When the emission layer is formed by vacuum deposition or spin coating, deposition and coating conditions for the emission layer may be determined by referring to the deposition and coating conditions described with respect to the HIL.

When the organic light-emitting device 10 is a full color organic light-emitting device, the emission layer may be patterned into a red emission layer, a green emission layer, or a blue emission layer, according to a sub pixel. In some embodiments, the emission layer may have a structure in which a red emission layer, a green emission layer, and a blue emission layer are stacked on one another or a structure in which a red-light emitting material, a green-light emitting material, and a blue-light emitting material are mixed with one another in a single layer, and thus may emit white light.

The emission layer may include a host and a dopant.

The host may include at least one selected from TPBi, TBADN, ADN (also referred to as "DNA"), CBP, CDBP, and TCP:

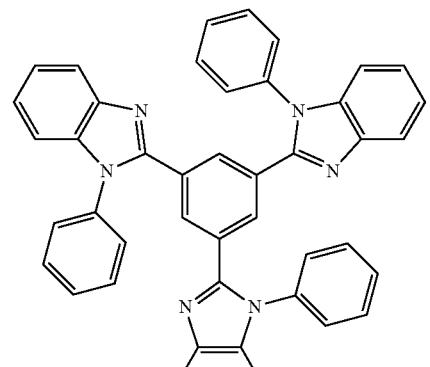

TPBi

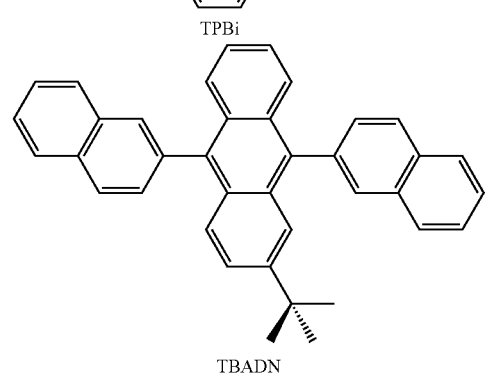

TBADN

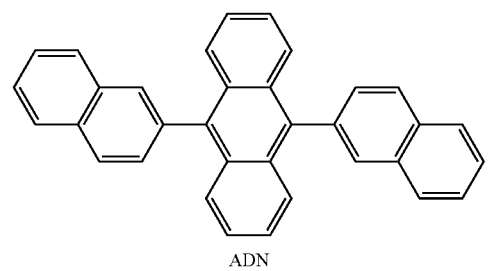

ADN

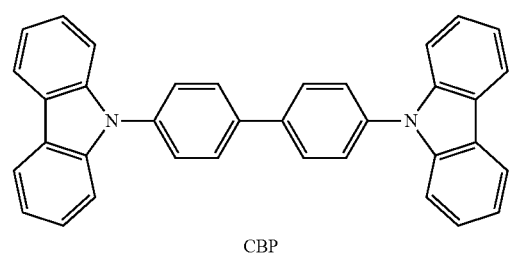

CBP

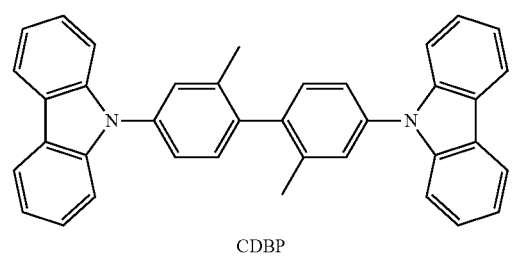

CDBP

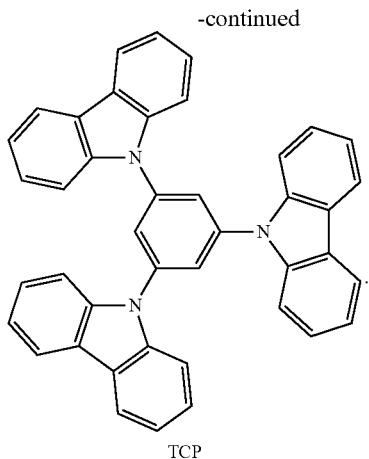

TCP

In some embodiments, the host may include a compound represented by Formula 301.

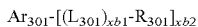

$\text{Ar}_{301}\text{-}[(\text{L}_{301})_{xb1}\text{-R}_{301}]_{xb2}$    Formula 301

In Formula 301, $\text{Ar}_{301}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (where $Q_{301}$ to $Q_{303}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group), $L_{301}$ may be understood by referring to the description of $L_{201}$ provided herein (e.g., $L_{301}$ may be the same as $L_{201}$ as described with respect to Formulae 201 and 202), $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xb1 may be selected from 0, 1, 2, and 3, and xb2 may be selected from 1, 2, 3, and 4.

For example, in Formula 301, $L_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but the compound is not limited thereto.

For example, the host may include a compound represented by Formula 301A:

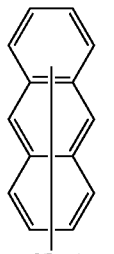

Formula 301A $[(L_{301})_{xb1}\text{—}R_{301}]_{xb2}$.

A substituent in Formula 301A may be understood by referring to the description thereof provided herein (e.g., $L_{301}$, xb1, $R_{301}$, and xb2 may be the same as those described with respect to Formula 301).

The compound represented by Formula 301 may include at least one selected from Compounds H1 to H42, but the compound represented by Formula 301 is not limited thereto:

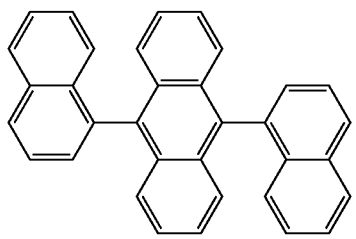

H1

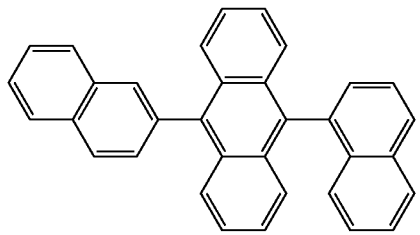

H2

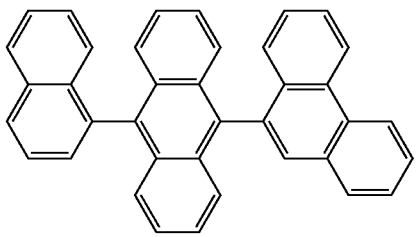

H3

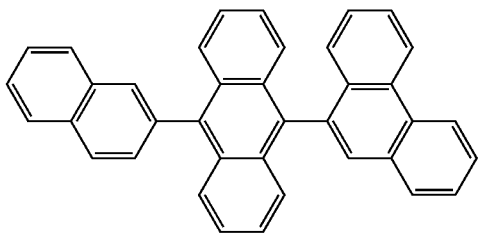

H4

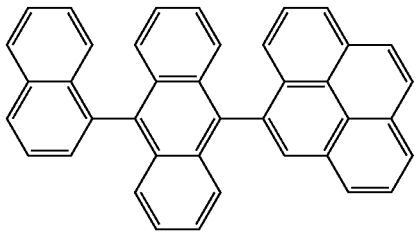

H5

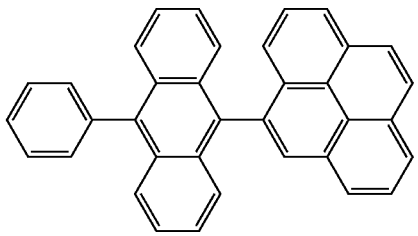

H6

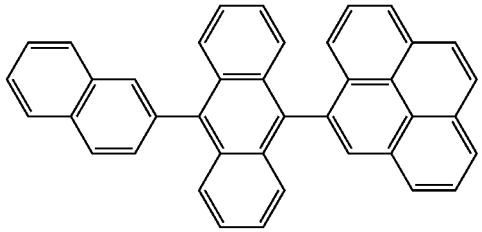

H7

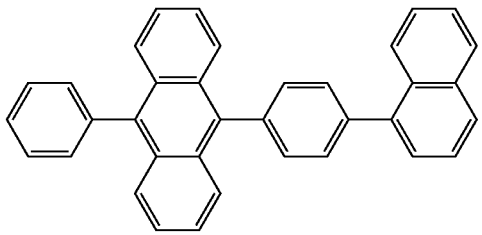

H8

H9
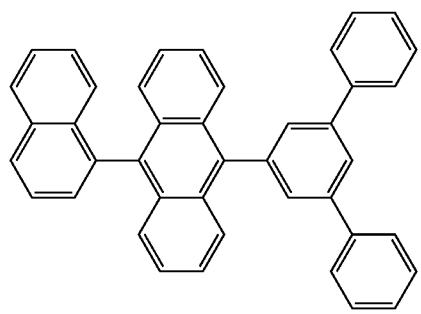
H10
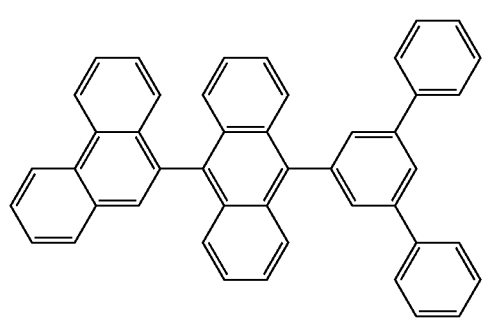
H11
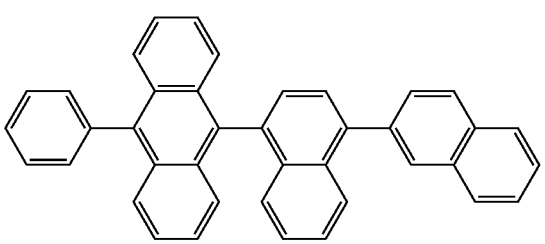
H12
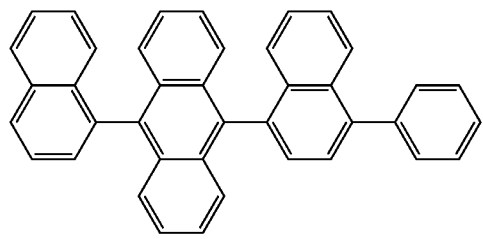
H13
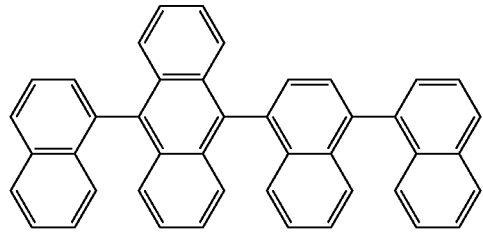
H14
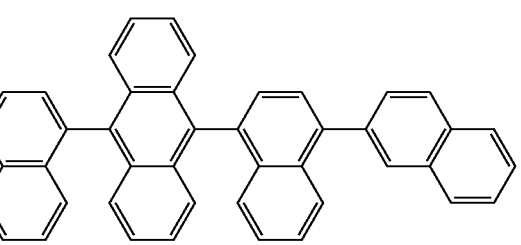
H15
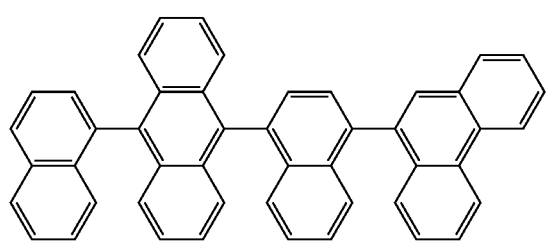
H16
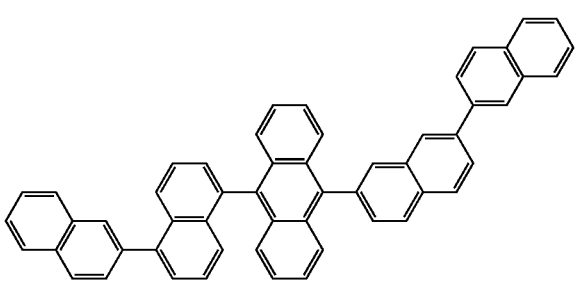
H17
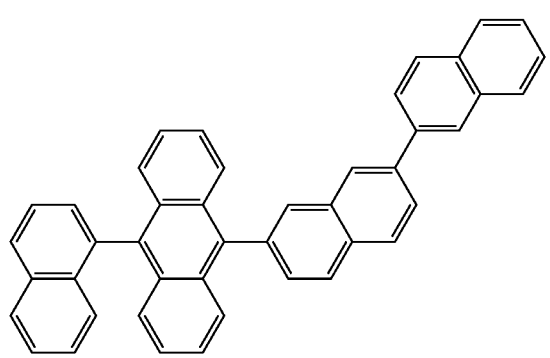
H18
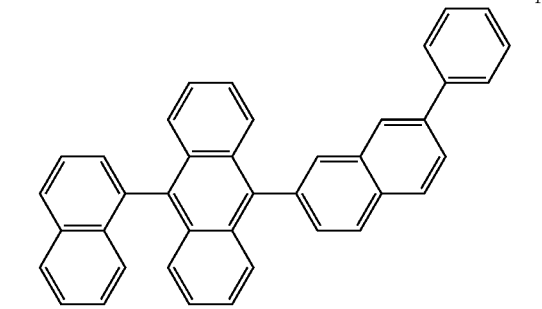
H19
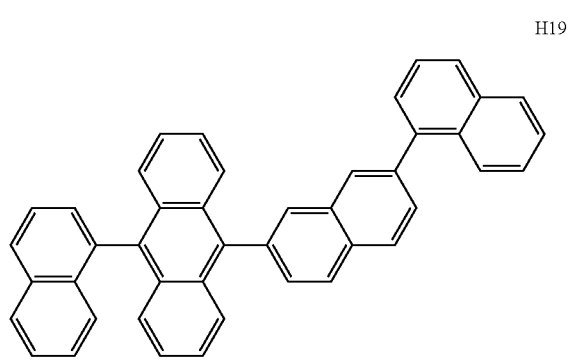

-continued
H20
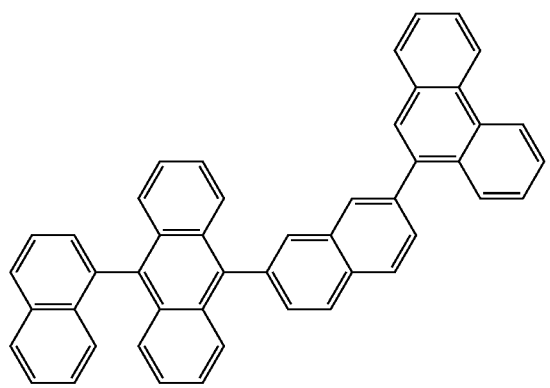
H21
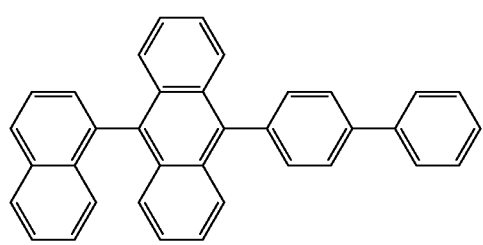
H22
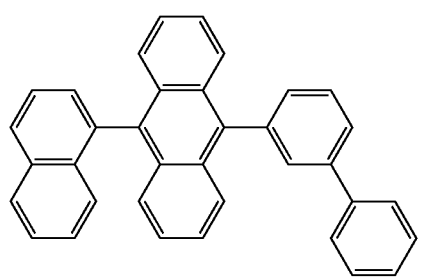
H23
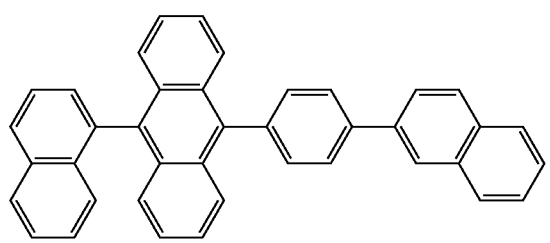
H24
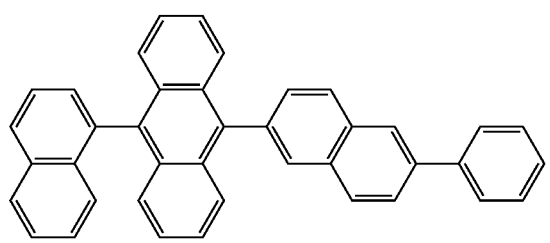
-continued
H25
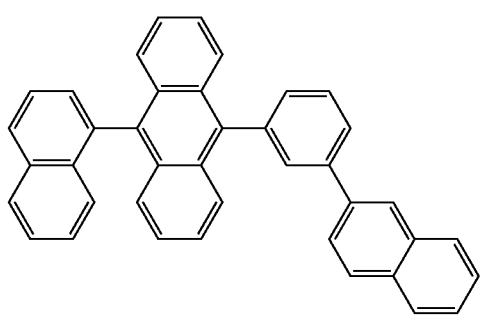
H26
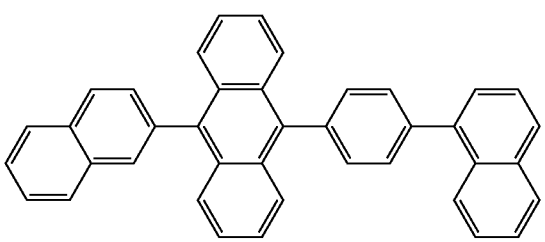
H27
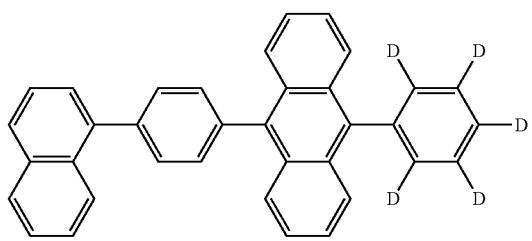
H28
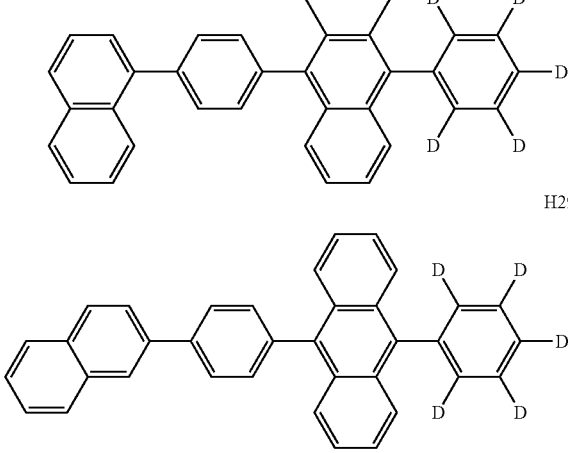
H29
H30
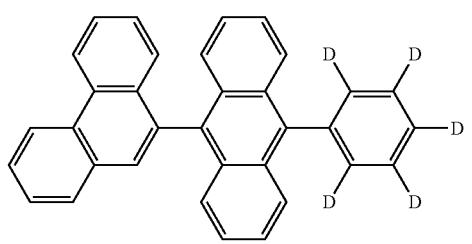

H31
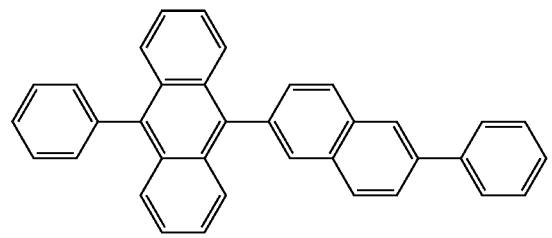
H32
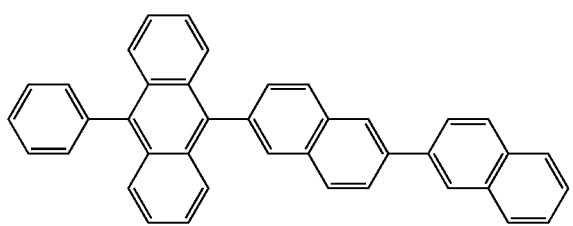
H33
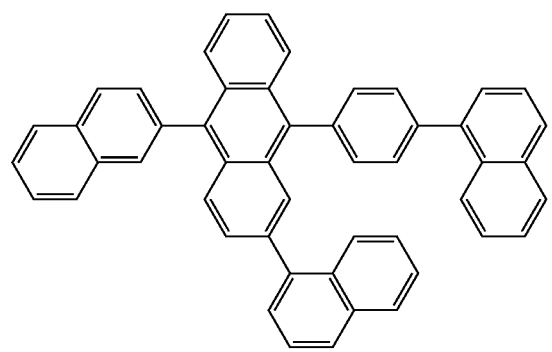
H34
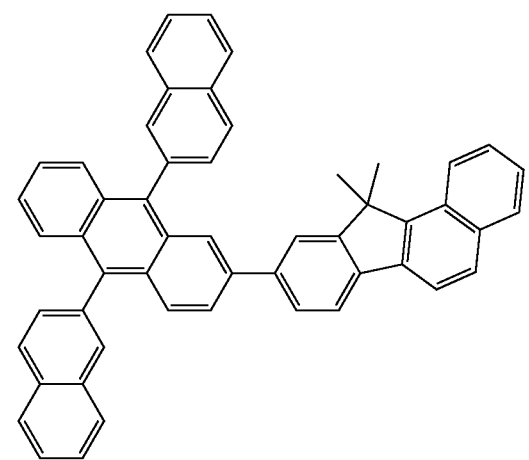
H35
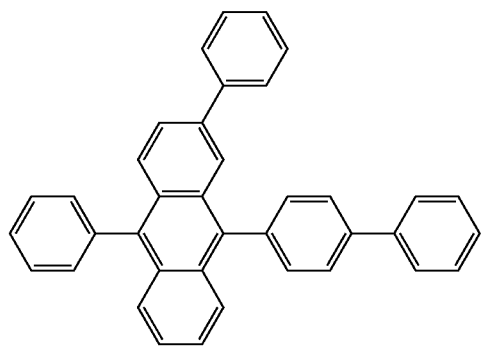
H36
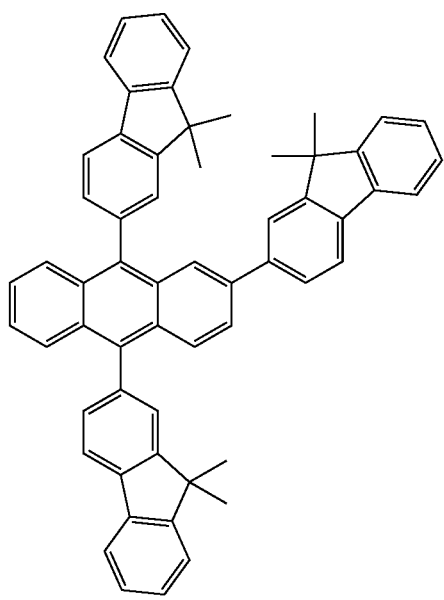
H37
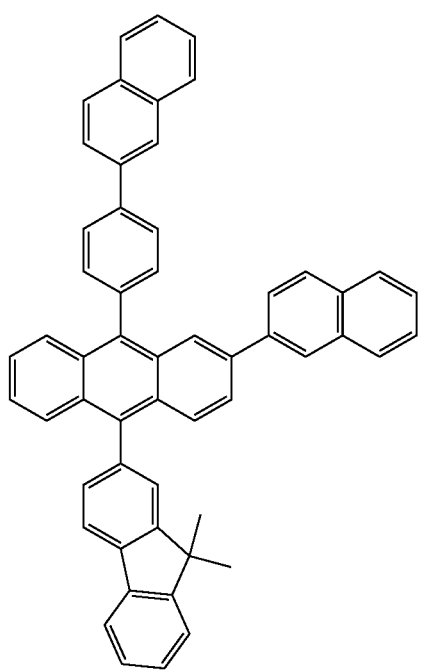

H38
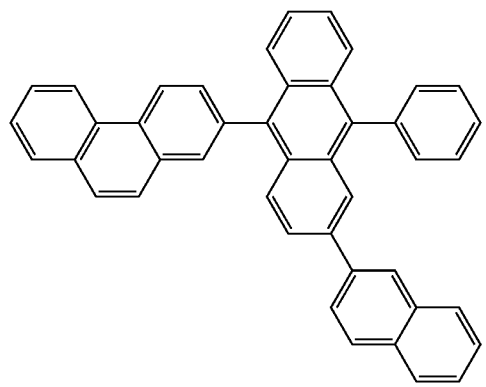
H41
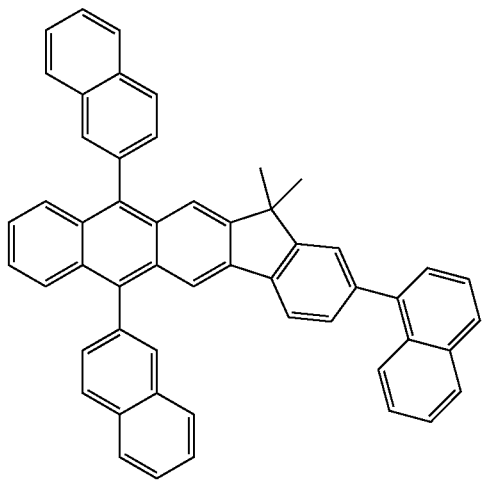
H39
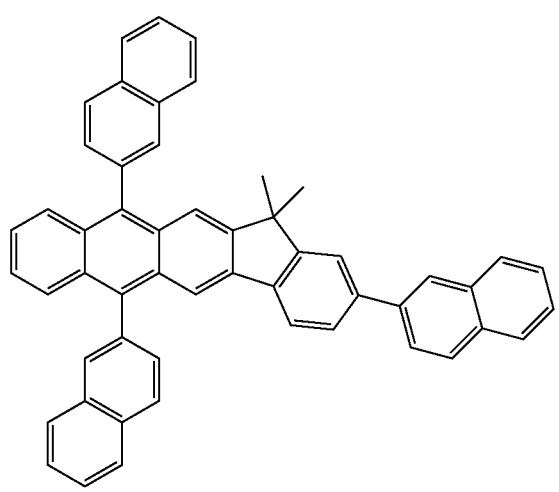
H42
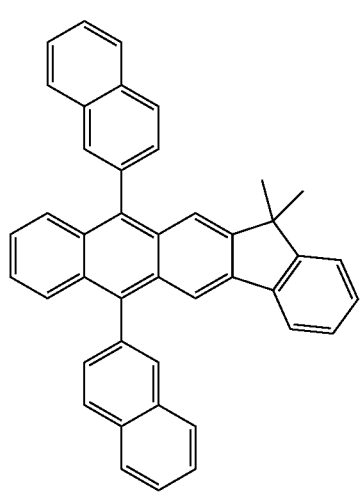
H40
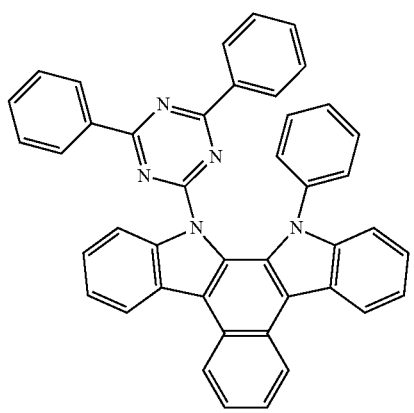
In some embodiments, the host may include at least one selected from Compounds H43 to H49, but the host is not limited thereto:
H43

H44
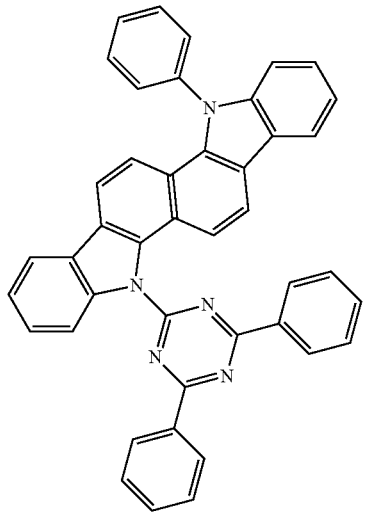
H45
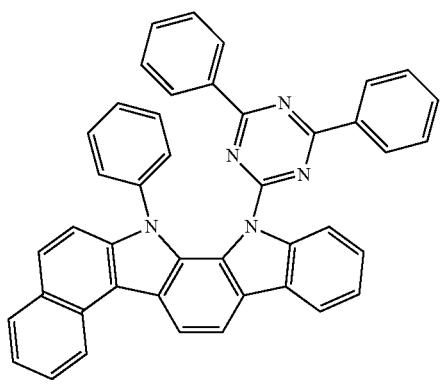
H46
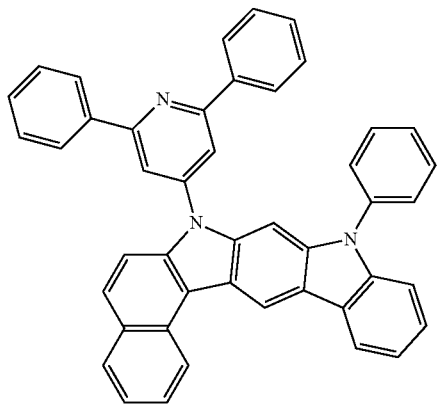
H47
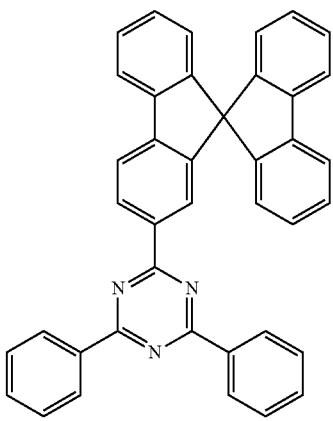
H48
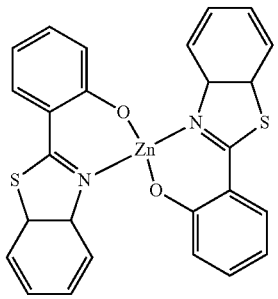
H49
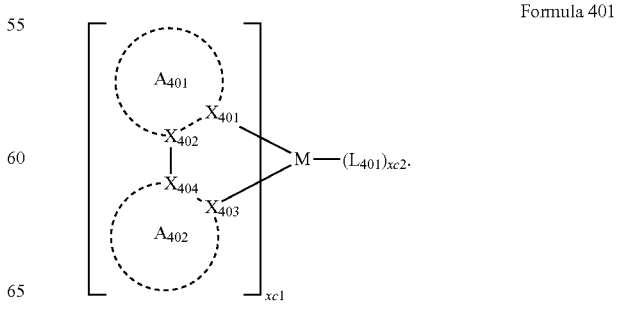
The dopant may include at least one selected from a fluorescent dopant and a phosphorescent dopant.
The phosphorescent dopant may include an organometallic complex represented by Formula 401:
Formula 401
$$\left[ \begin{array}{c} A_{401} \overset{X_{401}}{\underset{X_{402}}{\diagup}} \\ X_{404} \overset{X_{403}}{\diagup} \\ A_{402} \end{array} M - (L_{401})_{xc2} \right]_{xc1}$$

In Formula 401,

M may be selected from iridium (Ir), platinum (Pt), osmium (Os), titanium (Ti), zirconium (Zr), hafnium (Hf), europium (Eu), terbium (Tb), and thulium (TM), $X_{401}$ to $X_{404}$ may be each independently selected from a nitrogen and a carbon, $A_{401}$ ring and $A_{402}$ ring may be each independently selected form a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isooxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene, at least one of the substituents of the substituted benzene, substituted naphthalene, substituted fluorene, substituted spiro-fluorene, substituted indene, substituted pyrrole, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzoimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, substituted with at least one selected from a deuterium, —F, —Cl, —Br, —I, a hydroxyl group, cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$), $L_{401}$ may be an organic ligand, xc1 may be selected from 1, 2, and 3, and xc2 may be selected from 0, 1, 2, and 3.

$L_{401}$ may be selected from a monovalent, divalent, and trivalent organic ligand. For example, $L_{401}$ may be selected from a halogen ligand (for example, Cl or F), a diketone ligand (for example, acetylacetonate, 1,3-diphenyl-1,3-propandionate, 2,2,6,6-tetramethyl-3,5-heptanedionate, or hexafluoroacetonate), a carboxylic acid ligand (for example, picolinate, dimethyl-3-pyrazolecarboxylate, or benzoate), a carbon monoxide ligand, an isonitrile ligand, a cyano ligand, and a phosphorus ligand (for example, phosphine or phosphite), but $L_{401}$ is not limited thereto.

In an exemplary embodiment, $Q_{401}$ to $Q_{407}$, $Q_{411}$ to $Q_{417}$, and $Q_{421}$ to $Q_{427}$ may be each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group.

When $A_{401}$ in Formula 401 has two or more substituents, the substituents of $A_{401}$ may bind to each other (e.g., combine together) to form a saturated or unsaturated ring.

When $A_{402}$ in Formula 401 has two or more substituents, the substituents of $A_{402}$ may bind to each other (e.g., combine together) to form a saturated or unsaturated ring.

When xc1 in Formula 401 is two or more, a plurality of ligands in Formula 401

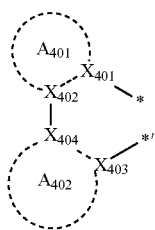

may be identical to or different from each other. When xc1 in Formula 401 is two or more, $A_{401}$ and $A_{402}$ may be respectively coupled or connected to $A_{401}$ and $A_{402}$ of other neighboring ligands directly or with a linker (for example, a $C_1$-$C_5$ alkylene group, —N(R')— (where R' may be a $C_1$-$C_{10}$ alkyl group or a $C_6$-$C_{20}$ aryl group), or —C(=O)—) therebetween.

The phosphorescent dopant may include at least one selected from Compounds PD1 to PD74, but the phosphorescent dopant is not limited thereto:

PD1

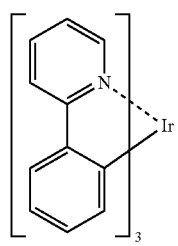

PD2

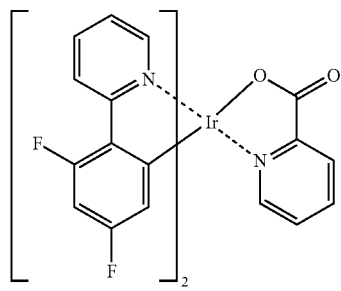

PD3

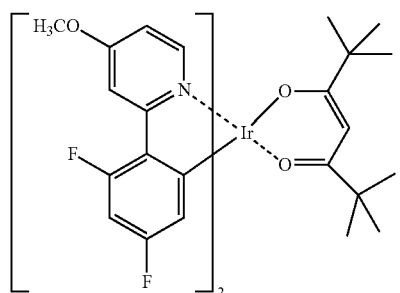

PD4

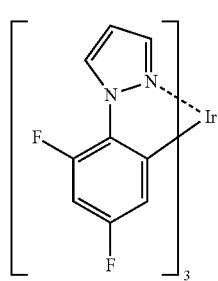

PD5

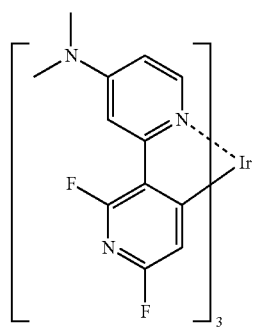

PD6

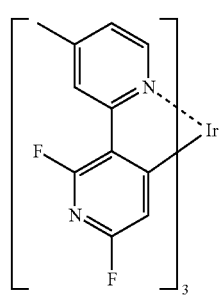

PD7

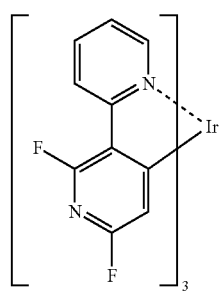

PD8

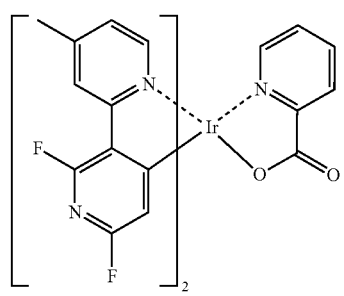

PD9

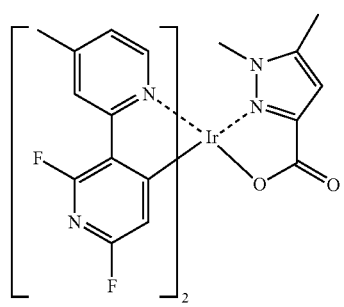

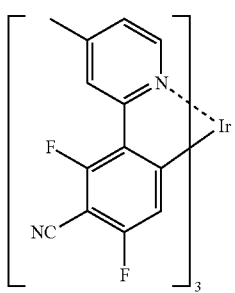 PD10
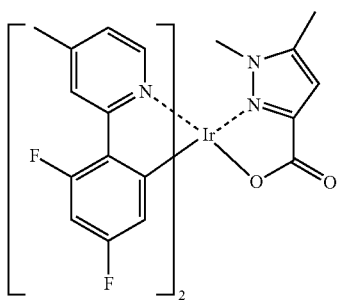 PD11
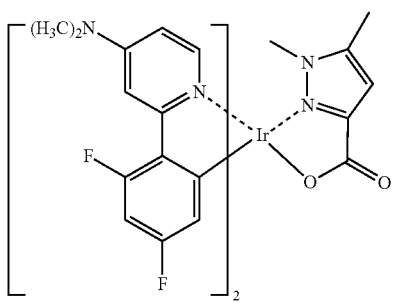 PD12
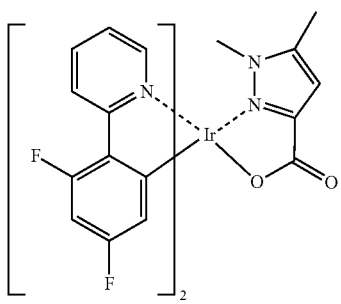 PD13
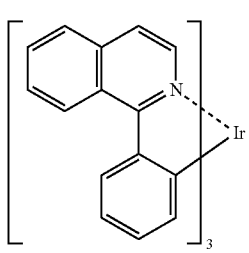 PD14
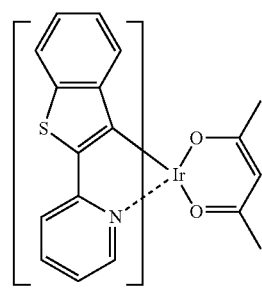 PD15
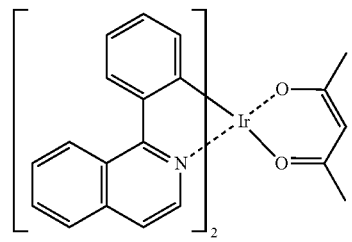 PD16
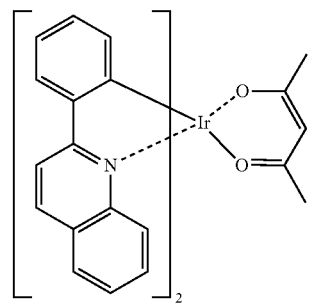 PD17
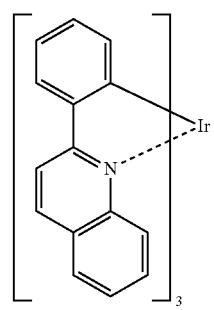 PD18
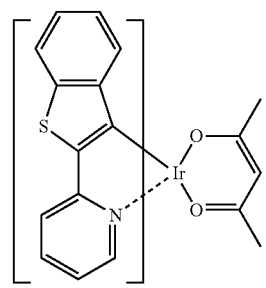 PD19

PD20 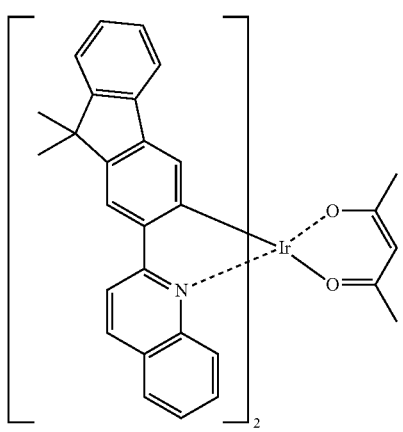
PD21 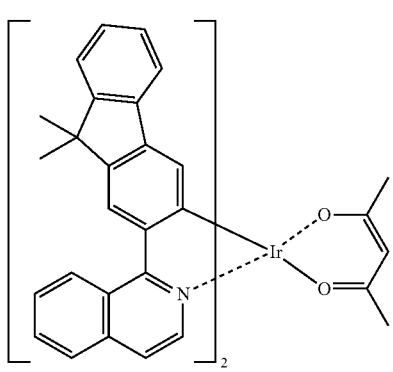
PD22 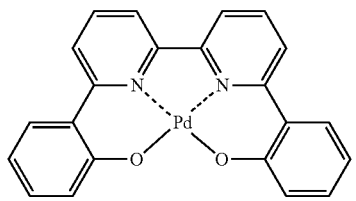
PD23 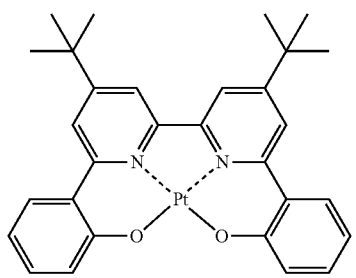
PD24 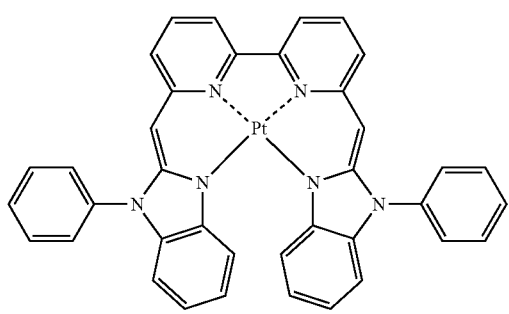
PD25 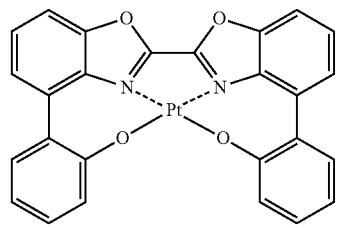
PD26 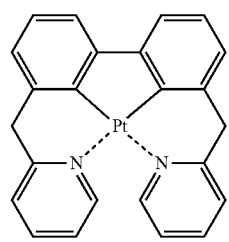
PD27 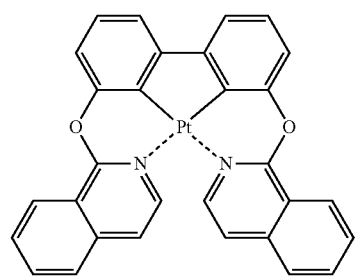
PD28 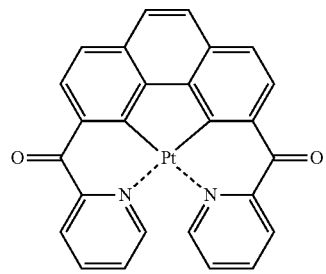
PD29 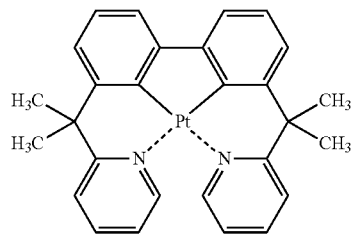
PD30 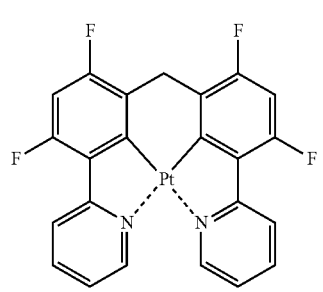

-continued
PD31
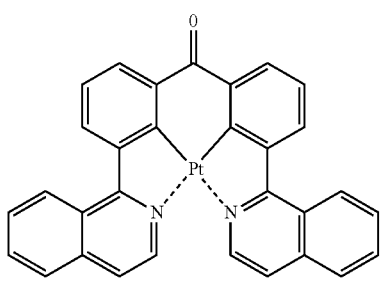
PD32
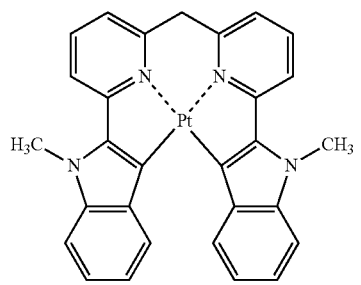
PD33
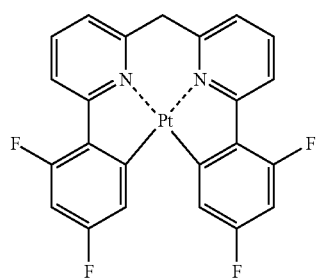
PD34
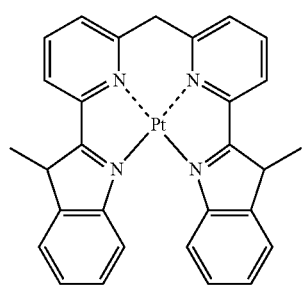
PD35
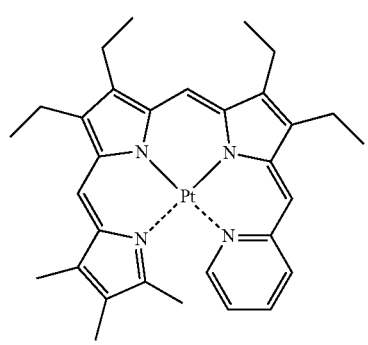
-continued
PD36
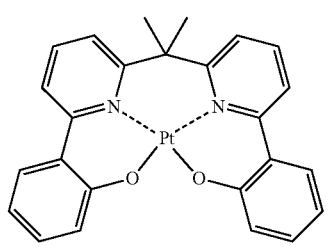
PD37
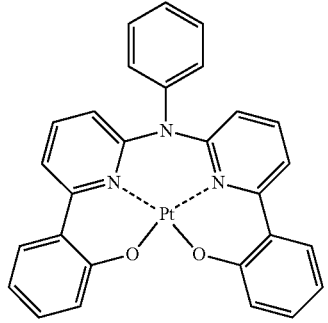
PD38
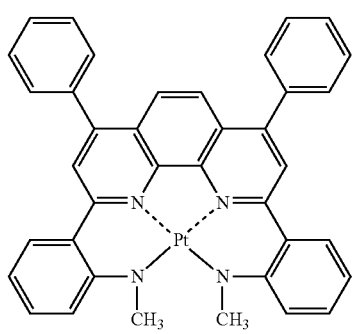
PD39
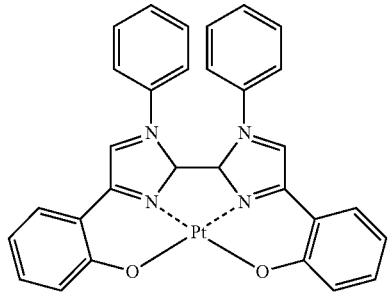
PD40
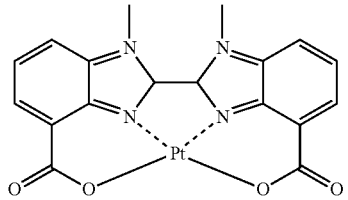
PD41
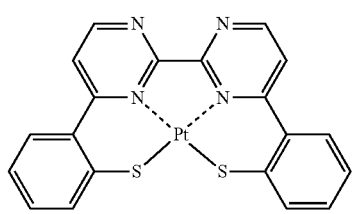

-continued
PD42
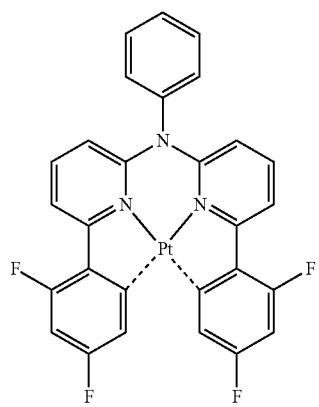
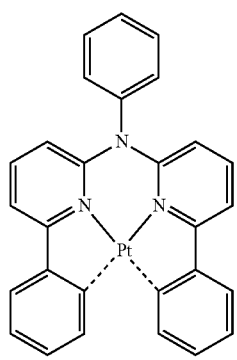
PD43
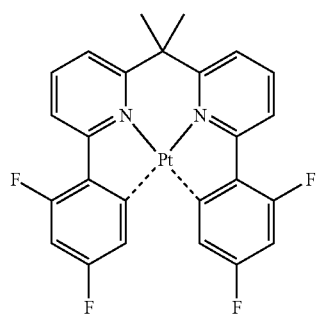
PD44
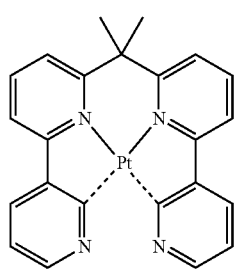
PD45
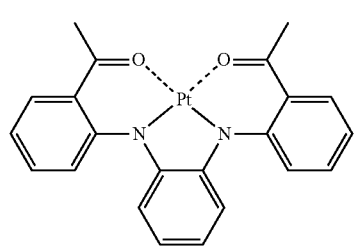
PD46
-continued
PD47
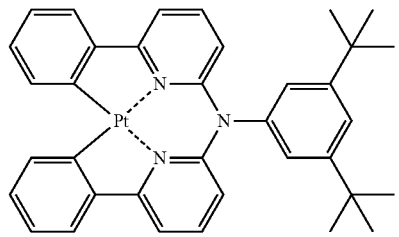
PD48
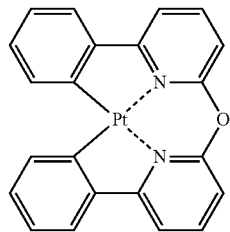
PD49
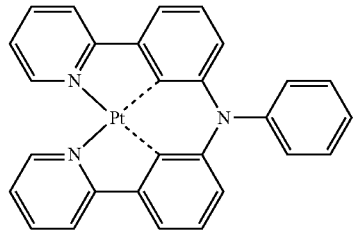
PD50
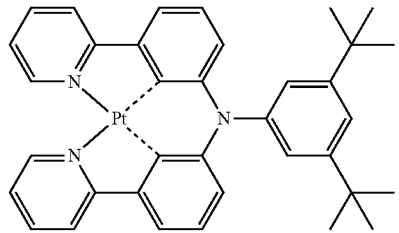
PD51
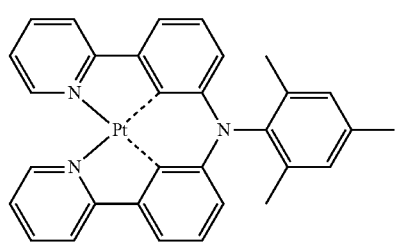
PD52
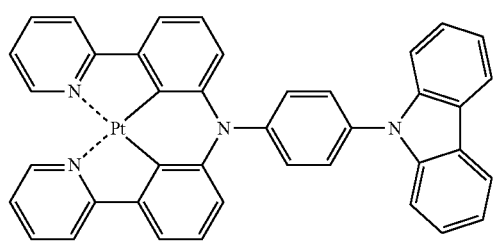

PD53 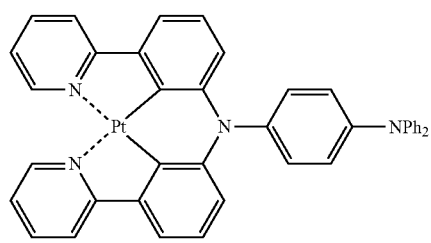
PD54 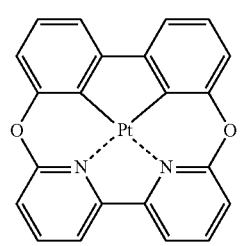
PD55 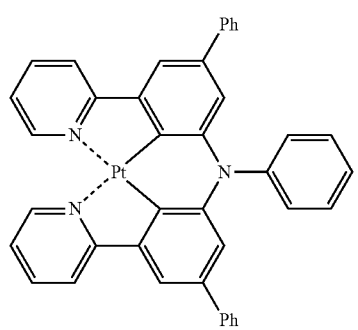
PD56 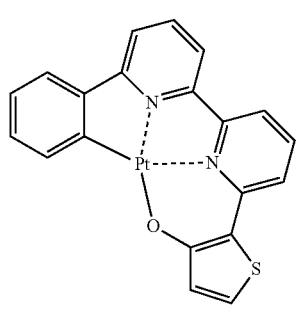
PD57 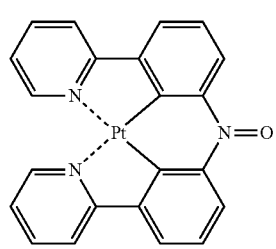
PD58 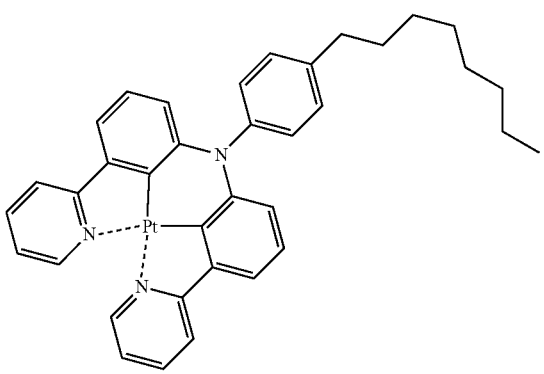
PD59 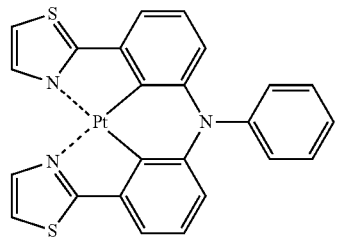
PD60 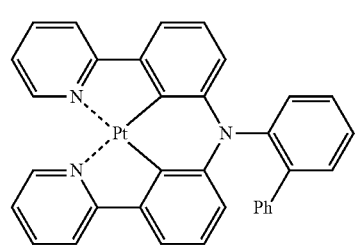
PD61 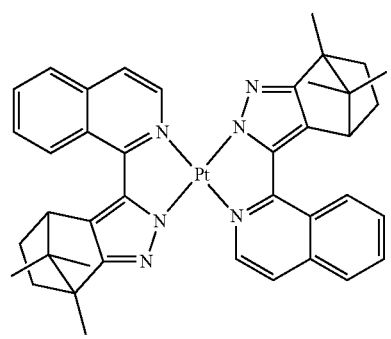
PD62 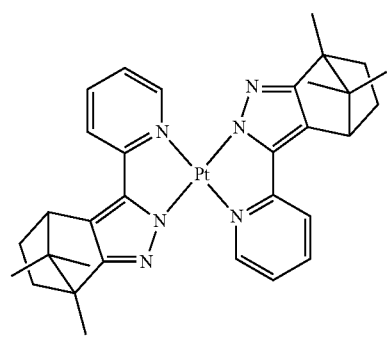

-continued
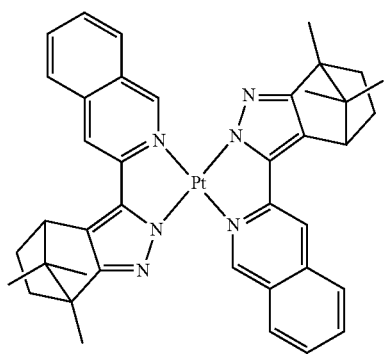
PD63
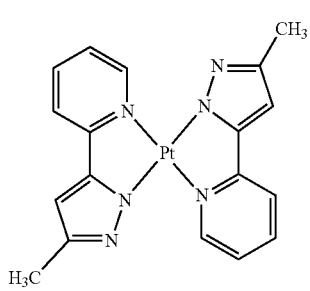
PD64
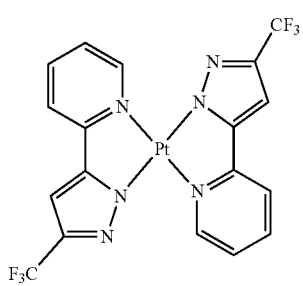
PD65
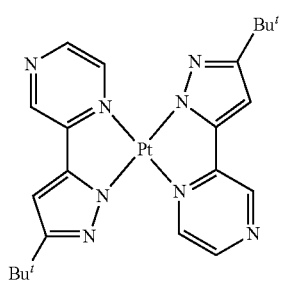
PD66
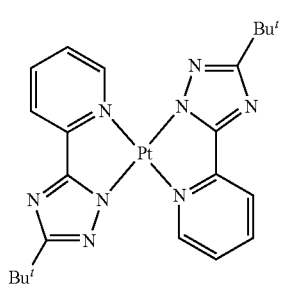
PD67
-continued
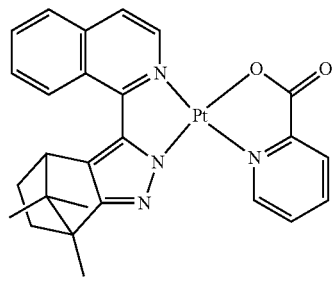
PD68
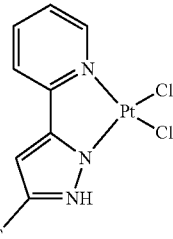
PD69
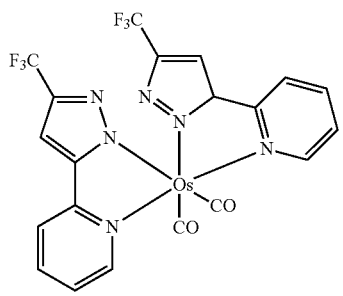
PD70
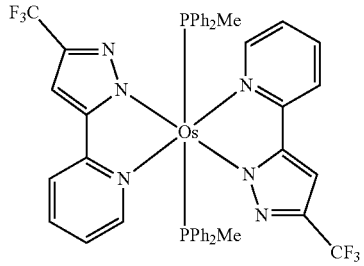
PD71
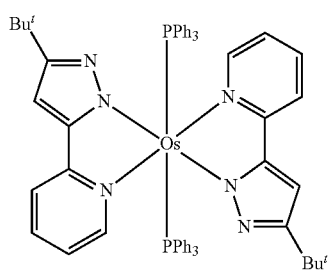
PD72

-continued
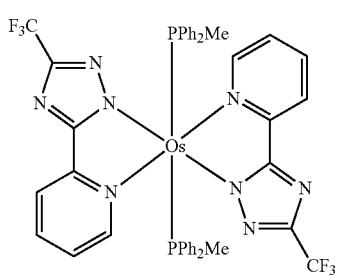
PD73
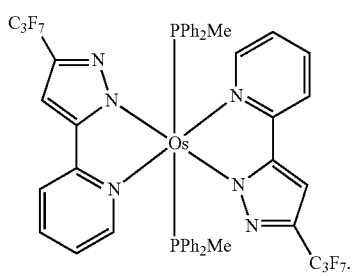
PD74
In some embodiments, the phosphorescent dopant may include PtOEP:
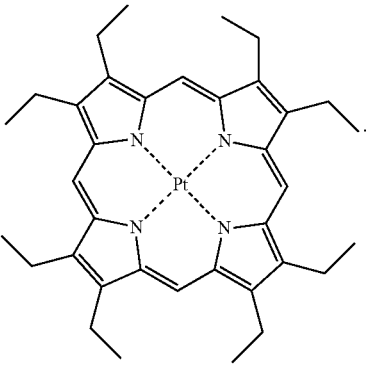
PtOEP
The fluorescent dopant may include at least one selected from DPAVBi, BDAVBi, TBPe, DCM, DCJTB, Coumarin 6, and C545T.
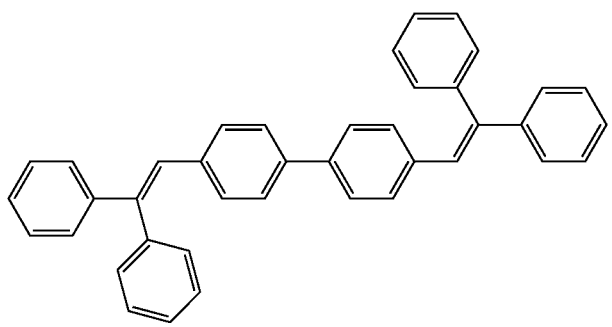
DPVBi
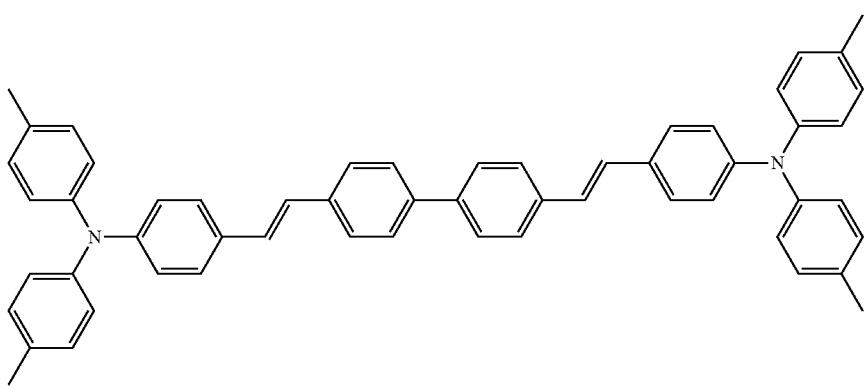
DPAVBi -continued

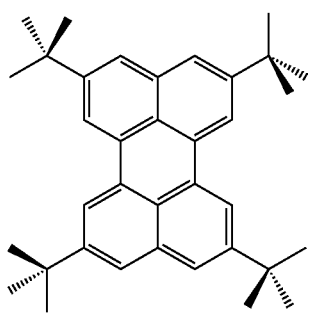
TBPe

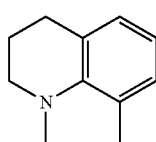
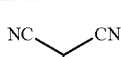
DCM

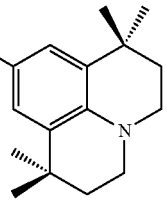
DCJTB

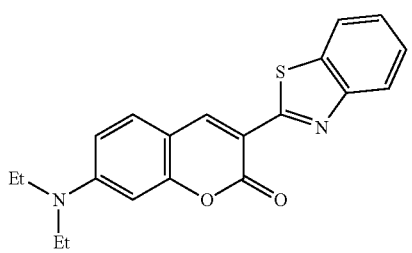
Coumarin 6

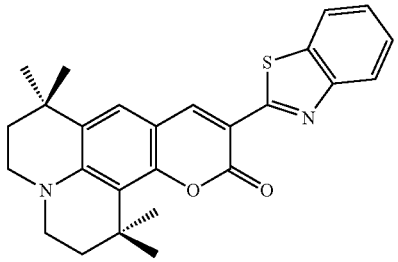
C545T

In some embodiments, the fluorescent dopant may include a compound represented by Formula 501:

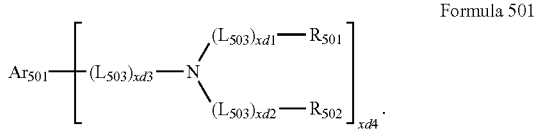

Formula 501

In Formula 501, $Ar_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (where $Q_{501}$ to $Q_{503}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group), $L_{501}$ to $L_{503}$ may each be understood by referring to the description of $L_{201}$ provided herein (e.g., $L_{501}$ to $L_{503}$ may be the same as $L_{201}$ as described with respect to Formulae 201 and 202), $R_{501}$ and $R_{502}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may be each independently selected from 0, 1, 2, and 3, and xd4 may be selected from 1, 2, 3, and 4.

The fluorescent dopant may include at least one selected from Compounds FD1 to FD8:
FD1
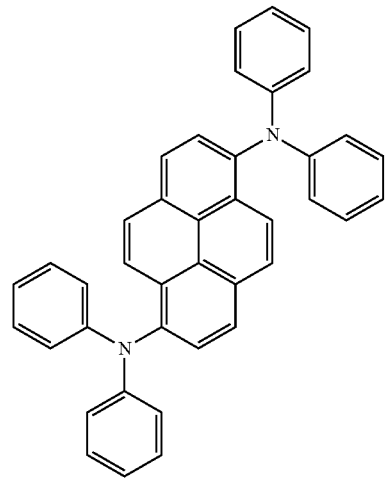
FD2
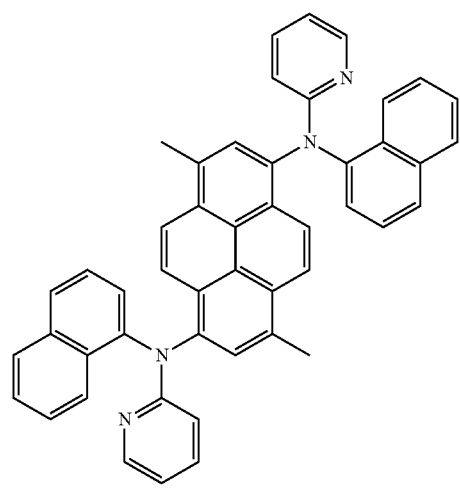
FD3
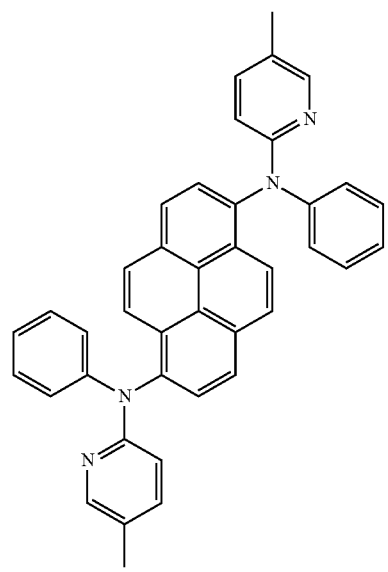
FD4
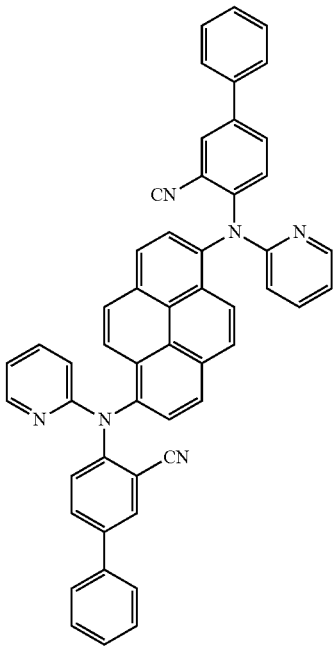
FD5
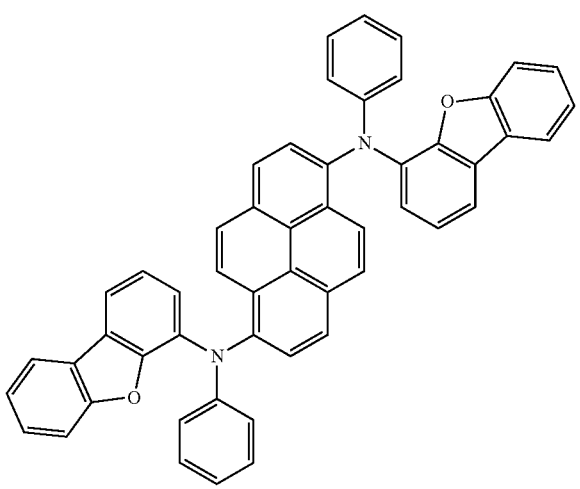
FD6
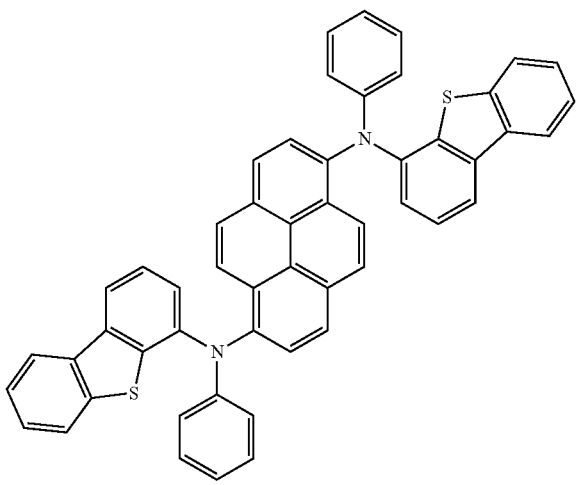

-continued

FD7

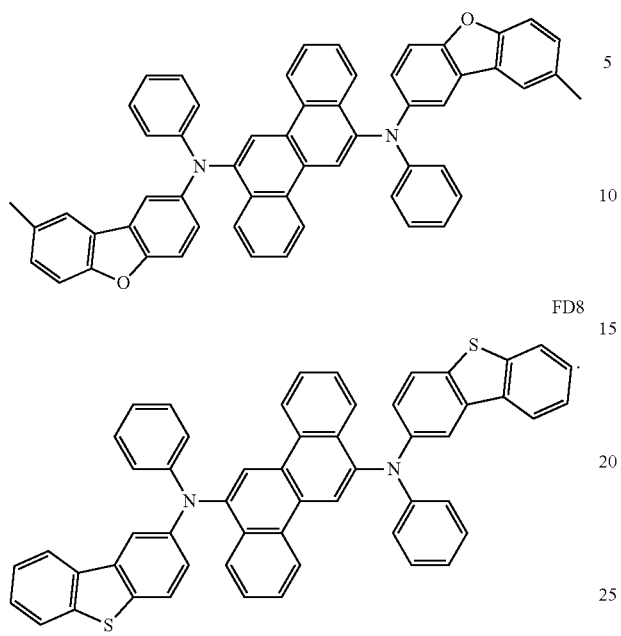

FD8

An amount of the dopant in the emission layer, in general, may be in a range from about 0.01 to about 15 parts by weight based on about 100 parts by weight of the host, but the dopant is not limited thereto.

A thickness of the emission layer may be in a range from about 100 Å to about 1000 Å, for example, from about 200 Å to about 600 Å. When the thickness of the emission layer is within the foregoing range, excellent light-emission characteristics may be obtained without a substantial increase in driving voltage.

Next, an electron transport region may be disposed on the emission layer.

The electron transport region may include at least one selected from an HBL, an ETL, and an EIL, but the electron transport region is not limited thereto.

For example, the electron transport region may have a structure of ETL/EIL or a structure of HBL/ETL/EIL, where layers of each structure are sequentially stacked from the emission layer in this stated order. However, the structure of the electron transport region is not limited thereto.

In some embodiments, the organic layer 150 of the organic light-emitting device 10 may include an electron transport region between the emission layer and the second electrode 190, and at least one of the condensed-cyclic compounds represented by Formula 1 may be present in the electron transport region.

The electron transport region may include an HBL. The HBL may be formed to prevent triplet excitons or holes from being spread to an ETL (or to reduce a likelihood or amount of such spread of triplet excitons or holes) in the case that the emission layer includes a phosphorescent dopant.

When the electron transport region includes an HBL, the HBL may be formed on the emission layer by using various suitable methods such as vacuum deposition, spin coating, casting, an LB method, inkjet printing, laser printing, or LITI. When the HBL is formed by vacuum deposition or spin coating, deposition and coating conditions for the HBL may be determined by referring to the deposition and coating conditions described with respect to the HIL.

The HBL may include, for example, at least one selected from BCP and Bphen, but the HBL is not limited thereto.

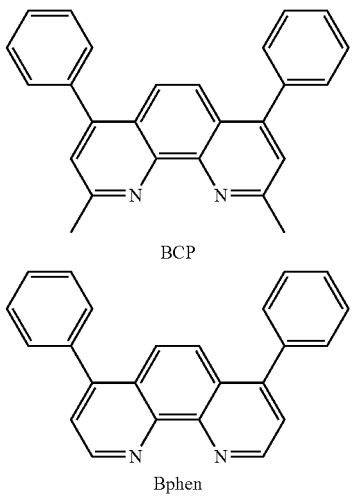

BCP

Bphen

A thickness of the HBL may be in a range from about 20 Å to about 1000 Å, for example, from about 30 Å to about 300 Å. When the thickness of the HBL is within the foregoing range, excellent hole blocking characteristics may be obtained without a substantial increase in driving voltage.

The electron transport region may include an ETL. The ETL may be formed on the emission layer or on the HBL by using various suitable methods such as vacuum deposition, spin coating, casting, an LB method, inkjet printing, laser printing, or LITI. When the ETL is formed by vacuum deposition or spin coating, deposition and coating conditions for the ETL may be determined by referring to the deposition and coating conditions described with respect to the HIL.

In some embodiments, the organic layer 150 of the organic light-emitting device 10 may include an electron transport region between the emission layer and the second electrode 190, the electron transport region may include an ETL, and at least one of the condensed-cyclic compounds represented by Formula 1 may be present in the ETL.

In addition to the condensed-cyclic compound represented by Formula 1, the ETL may further include at least one selected from BCP, Bphen, Alq$_3$, Balq, TAZ, and NTAZ.

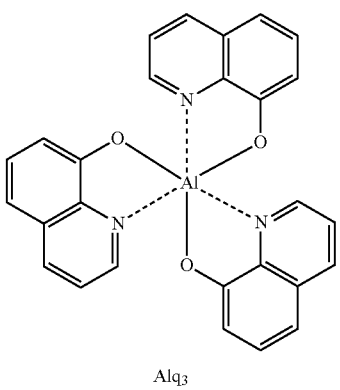

Alq$_3$

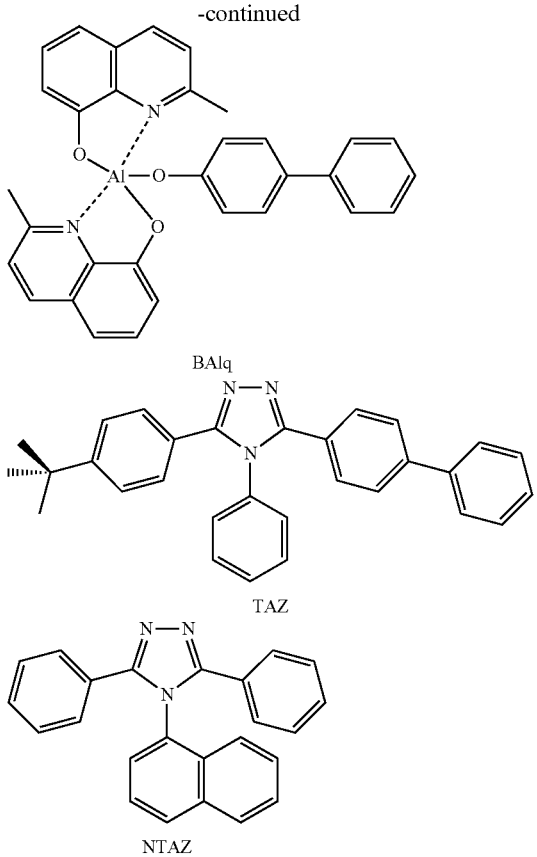

BAlq

TAZ

NTAZ

A thickness of the ETL may be in a range from about 100 Å to about 1000 Å, for example, from about 150 Å to about 500 Å. When the thickness of the ETL is within the foregoing range, satisfactory or suitable electron transport characteristics may be obtained without a substantial increase in driving voltage.

The ETL may further include, in addition to a material as described above, a metal-containing material.

The metal-containing material may include a Li complex. The Li complex may include, for example, Compound ET-D1 (lithium quinolate, LiQ) or ET-D2.

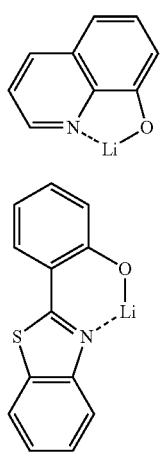

ET-D1

ET-D2

The electron transport region may include an EIL which facilitates the injection of electrons from the second electrode 190.

The EIL may be formed on the ETL by using various suitable methods such as vacuum deposition, spin coating, casting, an LB method, inkjet printing, laser printing, or LITI. When the EIL is formed by vacuum deposition or spin coating, deposition and coating conditions for the EIL may be determined by referring to the deposition and coating conditions described with respect to the HIL.

The EIL may include at least one selected from LiF, NaCl, CsF, $Li_2O$, BaO, and LiQ.

A thickness of the EIL may be in a range from about 1 Å to about 100 Å, for example, from about 3 Å to about 90 Å. When the thickness of the EIL is within the foregoing range, satisfactory or suitable electron injection characteristics may be obtained without a substantial increase in driving voltage.

The second electrode 190 is disposed on the organic layer 150 having such a structure. The second electrode 190 may be a cathode (e.g., an electron injection electrode). In this regard, a material for forming the second electrode 190 may be a material having a low work function, and such a material may be metal, alloy, an electrically conductive compound, or a mixture thereof. Examples of the second electrode 190 include lithium (Li), magnesium (Mg), aluminum (Al), aluminum-lithium (Al—Li), calcium (Ca), magnesium-indium (Mg—In), or magnesium-silver (Mg—Ag). In some embodiments, ITO and/or IZO may be used as the material for forming the second electrode 190. The second electrode 190 may be a reflective electrode, a semi-transmissive electrode or a transmissive electrode.

The organic light-emitting device has been described above with reference to the accompanying drawing, but the organic light-emitting device is not limited thereto.

The term "$C_1$-$C_{60}$ alkyl group," as used herein, refers to a linear or branched aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group," as used herein, refers to a divalent group having the same or substantially the same structure as the $C_1$-$C_{60}$ alkyl group (except that the $C_1$-$C_{60}$ alkylene group is divalent instead of monovalent).

The term "$C_1$-$C_{60}$ alkoxy group," as used herein, refers to a monovalent group represented by —$OA_{101}$ (where $A_{101}$ is the $C_1$-$C_{60}$ alkyl group), and examples thereof include a methoxy group, an ethoxy group, and an isopropyloxy group.

The term "$C_2$-$C_{60}$ alkenyl group," as used herein, refers to a hydrocarbon group formed by substituting at least one carbon double bond in a main chain (e.g., in the middle) or at the terminal end of a $C_2$-$C_{60}$ alkyl group, and examples thereof include an ethenyl group, a prophenyl group, and a butenyl group. The term "$C_2$-$C_{60}$ alkenylene group," as used herein, refers to a divalent group having the same or substantially the same structure as the $C_2$-$C_{60}$ alkenyl group (except that the $C_2$-$C_{60}$ alkenyl group is divalent instead of monovalent).

The term "$C_2$-$C_{60}$ alkynyl group," as used herein, refers to a hydrocarbon group formed by substituting at least one carbon triple bond in a main chain (e.g., in the middle) or at the terminal end of the $C_2$-$C_{60}$ alkyl group, and examples thereof include an ethynyl group and a propynyl group. The term "$C_2$-$C_{60}$ alkynylene group," as used herein, refers to a divalent group having the same or substantially the same structure as the $C_2$-$C_{60}$ alkynyl group (except that the $C_2$-$C_{60}$ alkynylene group is divalent instead of monovalent).

The term "$C_3$-$C_{10}$ cycloalkyl group," as used herein, refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having the same or substantially the same structure as the $C_3$-$C_{10}$ cycloalkyl group (except that the $C_3$-$C_{10}$ cycloalkylene group is divalent instead of monovalent).

The term "$C_1$-$C_{10}$ heterocycloalkyl group," as used herein, refers to a monovalent monocyclic group having at least one heteroatom selected from N, O, P, and S as a ring-forming atom and 1 to 10 carbon atoms, and examples thereof include a tetrahydrofuranyl group and a tetrahydrothiophenyl group. The term "$C_1$-$C_{10}$ heterocycloalkylene group," as used herein, refers to a divalent group having the same or substantially the same structure as the $C_1$-$C_{10}$ heterocycloalkyl group (except that the $C_1$-$C_{10}$ heterocycloalkylene group is divalent instead of monovalent).

The term "$C_3$-$C_{10}$ cycloalkenyl group," as used herein, refers to a monovalent monocyclic group that has 3 to 10 carbon atoms and at least one double bond in the ring thereof and does not have aromaticity (e.g., is not aromatic), and examples thereof include a cyclopentenyl group, a cyclohexenyl group, and a cycloheptenyl group. The term "$C_3$-$C_{10}$ cycloalkenylene group," as used herein, refers to a divalent group having the same or substantially the same structure as the $C_3$-$C_{10}$ cycloalkenyl group (except that the $C_3$-$C_{10}$ cycloalkenylene group is divalent instead of monovalent).

The term "$C_1$-$C_{10}$ heterocycloalkenyl group," as used herein, refers to a monovalent monocyclic group that has at least one heteroatom selected from N, O, P, and S as a ring-forming atom, 1 to 10 carbon atoms, and at least one double bond in its ring. Examples of the $C_1$-$C_{10}$ heterocycloalkenyl group include a 2,3-hydrofuranyl group and a 2,3-hydrothiophenyl group. The term "$C_1$-$C_{10}$ heterocycloalkenylene group," as used herein, refers to a divalent group having the same or substantially the same structure as the $C_1$-$C_{10}$ heterocycloalkenyl group (except that the $C_1$-$C_{10}$ heterocycloalkenylene group is divalent instead of monovalent).

The term "$C_6$-$C_{60}$ aryl group," as used herein, refers to a monovalent group having a carbocyclic aromatic system having 6 to 60 carbon atoms, and the term "$C_6$-$C_{60}$ arylene group," as used herein, refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other (e.g., combined together).

The term "$C_1$-$C_{60}$ heteroaryl group," as used herein, refers to a monovalent group having a carbocyclic aromatic system that has at least one heteroatom selected from N, O, P, and S as a ring-forming atom and 1 to 60 carbon atoms. The term "$C_1$-$C_{60}$ heteroarylene group," as used herein, refers to a divalent group having a carbocyclic aromatic system that has at least one heteroatom selected from N, O, P, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other (e.g., combined together).

The term "$C_6$-$C_{60}$ aryloxy group," as used herein indicates —$OA_{102}$ (where $A_{102}$ is the $C_6$-$C_{60}$ aryl group), and the term "$C_6$-$C_{60}$ arylthio group," as used herein, indicates —$SA_{103}$ (where $A_{103}$ is the $C_6$-$C_{60}$ aryl group).

The term "monovalent non-aromatic condensed polycyclic group," as used herein, refers to a monovalent group (for example, having 8 to 60 carbon atoms) that has two or more rings condensed to each other (e.g., combined together), only carbon atoms as a ring forming atom, and non-aromaticity in the entire molecular structure (e.g., the entire molecular structure is not aromatic). An example of the monovalent non-aromatic condensed polycyclic group is a fluorenyl group. The term "divalent non-aromatic condensed polycyclic group," as used herein, refers to a divalent group having the same or substantially the same structure as the monovalent non-aromatic condensed polycyclic group (except that the divalent non-aromatic condensed polycyclic group is divalent instead of monovalent).

The "monovalent non-aromatic condensed heteropolycyclic group," as used herein, refers to a monovalent group (for example, having 1 to 60 carbon atoms) that has two or more rings condensed to each other (e.g., combined together), has a heteroatom selected from N, O, P, and S, other than carbon atoms, as a ring forming atom, and has non-aromaticity in the entire molecular structure (e.g., the entire molecular structure is not aromatic). An example of the monovalent non-aromatic condensed heteropolycyclic group is a carbazolyl group. The term "divalent non-aromatic condensed heteropolycyclic group," as used herein, refers to a divalent group having the same or substantially the same structure as the monovalent non-aromatic condensed heteropolycyclic group (except that the divalent non-aromatic condensed heteropolycyclic group is divalent instead of monovalent).

At least one of the substituents of the substituted phenylene group, substituted naphthylene group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted biphenyl group, substituted terphenyl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —B($Q_{14}$)($Q_{15}$), and —N($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a biphenyl group, a terphenyl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a biphenyl group, a terphenyl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —B($Q_{24}$)($Q_{25}$), and —N($Q_{26}$)($Q_{27}$); and —Si($Q_{31}$)($Q_{32}$)($Q_{33}$), —B($Q_{34}$)($Q_{35}$), and —N($Q_{36}$)($Q_{37}$), where $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

As described herein, at least one of the substituents of the substituted phenylene group, substituted naphthylene group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted biphenyl group, substituted terphenyl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —Si($Q_{11}$)($Q_{12}$)($Q_{13}$), —B($Q_{14}$)($Q_{15}$), and —N($Q_{16}$)($Q_{17}$);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a biphenyl group, a terphenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a biphenyl group, a terphenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —Si($Q_{21}$)($Q_{22}$)($Q_{23}$), —B($Q_{24}$)($Q_{25}$), and —N($Q_{26}$)($Q_{27}$); and —Si($Q_{31}$)($Q_{32}$)($Q_{33}$), —B($Q_{34}$)($Q_{35}$), and —N($Q_{36}$)($Q_{37}$), where $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The term "CN," as used herein, refers to a cyano group, the term "Ph," as used herein, refers to a phenyl group, the term "Me," as used herein, refers to a methyl group, the term "Et," as used herein, refers to an ethyl group, and the terms "ter-Bu" and "Bu$^t$," as used herein, each refers to a tert-butyl group.

Hereinafter, an organic light-emitting device according to an embodiment will be described in more detail with reference to Synthesis Examples and Examples. The wording "B was used instead of A" used in describing Synthesis Examples below means that a molar equivalent of A is identical (or substantially identical) to a molar equivalent of B.

EXAMPLE

Synthesis Example 1: Synthesis of Compound 1

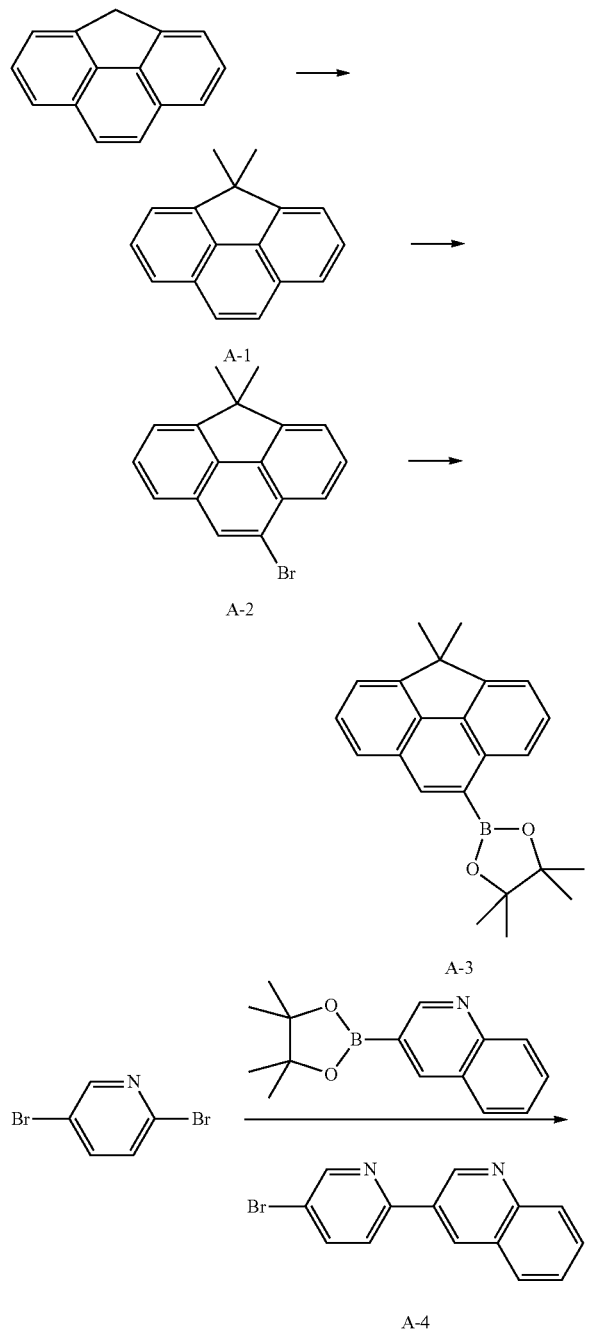

Synthesis of Intermediate A-1

5.6 g (29.7 mmol) of cyclopenta[def]phenanthrene was dissolved in 100 ml of DMSO in a 250 ml round bottom flask, and 0.5 g (0.1 eq, 2.97 mmol) of KI and 5.5 ml (3.0 eq, 89.2 mmol) of MeI were added thereto. The mixture was cooled to 10° C. and 9.7 g (5.0 eq, 148 mmol) of powder KOH (85%) was slowly added thereto. After 1 hour, the temperature was raised to room temperature, and the resultant was stirred for 10 hours. The resultant reaction solution was subjected to an extraction process by using a mixed solution including ethyl acetate and hexane at a volume ratio of 1:1, dried by using an anhydrous sodium sulfate and filtered to remove a solvent therefrom. The residue was separated and purified by using silica gel column chromatography. The resultant solid was recrystallized by using MeOH to obtain 6.6 g (yield: 75%) of Intermediate A-1.

Synthesis of Intermediate A-2

Intermediate A-1 (5.0 g, 22.9 mmol) was put in a 250 ml round bottom flask, and $CCl_4$ (100 ml) was added thereto. Then, the resultant reaction solution was cooled to 0° C., and $Br_2$ (3.3 g, 20.8 mmol) was added dropwise to the reaction solution. After a reaction was carried out for 4 hours, a 10% $NaSO_3$ solution was added thereto to separate an organic layer therefrom. The separated organic layer was distilled under reduced pressure, and then recrystallized by using n-hexane to obtain 4.9 g (yield: 80%) of Intermediate A-2.

Synthesis of Intermediate A-3

Under argon gas, 3.6 g (1 eq, 12.12 mmol) of Intermediate A-2 was dissolved in 100 ml of THF in a 250 ml round bottom flask, and then, 5.5 ml (1.2 eq, 14.54 mmol) of 2.5M n-BuLi was added thereto at −78° C. Next, the resultant reaction solution was stirred for 1 hour at −78° C., and 3.3 ml (1.3 eq, 15.75 mmol) of 2-isopropoxy-4,4,5,5-tetramethyl-1,3,2-dioxaborolan was added thereto, followed by stirring for 2 hours at room temperature. Then, 50 ml of water was added thereto to terminate the reaction, and an organic layer was separated therefrom by using brine and methylene chloride. The organic layer was dried by using an anhydrous magnesium sulfate and filtered to remove a solvent therefrom, and the obtained residue was separated and purified by using silica gel column chromatography to obtain 2.5 g (yield: 60%) of Intermediate A-3.

Synthesis of Intermediate A-4

1.11 g (4.7 mmol) of 3,5-dibromo-pyridine, 1.0 g (3.92 mmol) of 344,4,5,5-tetramethyl-[1,3,2]dioxaborolan-2-yl)-quinoline, 0.45 g of tetrakis(triphenylphosphine)palladium (0), 7.84 ml of 2M $K_2CO_3$, and 1.26 g of tetrabutylammonium bromide were put in a 100 ml round bottom flask under argon gas, and 30 ml of THF and 15 ml of toluene were added thereto, followed by refluxing for 16 hours at 100° C. After it was confirmed that the solution turned a dark brown color, water was added thereto, and an organic layer was extracted therefrom by using chloroform. The organic layer was dried by using an anhydrous magnesium sulfate and filtered to remove a solvent therefrom, and the obtained residue was separated and purified by using silica gel column chromatography to obtain 1.1 g (yield: 93%) of Intermediate A-4.

Synthesis of Compound 1

0.61 g (2.15 mmol) of Intermediate A-4, 1.0 g (1.8 mmol) of Intermediate A-3, 3.6 ml of 1M $K_3PO_4$, and 20 ml of dioxane were put in a 100 ml round bottom flask under argon gas and refluxed for 36 hours at 120° C. Once the reaction was complete, a reaction mixture was cooled to room temperature, and 100 ml of toluene and 100 ml of distilled water were added thereto to extract an organic layer therefrom. The collected organic layer was dried by using $MgSO_4$ and then purified by silica gel column chromatography to obtain 0.7 g (yield: 92%) of Compound 1. As a result of measurement by Atmospheric Pressure Chemical Ionization (APCI) using LCMS (SHIMADZU, LCMS-IT-TOF), [M+H]+=423 was obtained as a main peak, and thus, it was confirmed that the obtained compound was the targeted compound.

Synthesis Example 2: Synthesis of Compound 4

0.63 g (yield: 82%) of Compound 4 was prepared in the same manner as used to synthesize Compound 1, except that in synthesizing Intermediate A-1, n-butyliodide was used instead of MeI. As a result of measurement by APCl using LCMS (liquid chromatography mass spectrometry), [M+H]+=429 was obtained as a main peak, and thus, it was confirmed that the obtained compound was the targeted compound.

Example 1

An ITO glass substrate (available from Corning Co., Ltd) on which an ITO layer having a thickness of 1,000 Å (15 $\Omega/cm^2$) was formed was cut to a size of 50 mm×50 mm×0.7 mm, sonicated in isopropyl alcohol and pure water for 5 minutes in each solvent, cleaned with ultraviolet rays for 30 minutes and then ozone, and the ITO glass substrate (anode) was mounted on a vacuum deposition apparatus.

DNTPD was vacuum-deposited on the ITO anode substrate to form a hole injection layer (HIL) having a thickness of 600 Å. Then, NPB was vacuum-deposited to a thickness of 300 Å on the HIL to form a hole transport layer (HTL).

TBADN, which is a host, and DPAVBi, which is a dopant, were co-deposited on the HTL to a weight ratio of 95:5, thereby forming an emission layer having a thickness of 300 Å.

Next, Compound 1 was deposited on the emission layer to form an electron transport layer (ETL) having a thickness of 250 Å. Then, LiF was deposited on the ETL to form an electron injection layer (EIL) having a thickness of 6 Å. Next, Aluminum (Al) was deposited on the EIL to form a cathode having a thickness of 1,500 Å, thereby completing the manufacture of an organic light-emitting device.

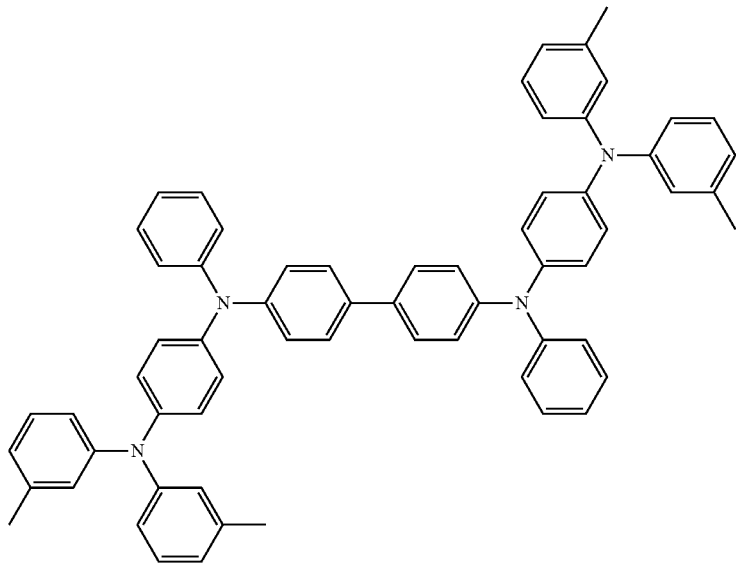

DNTPD

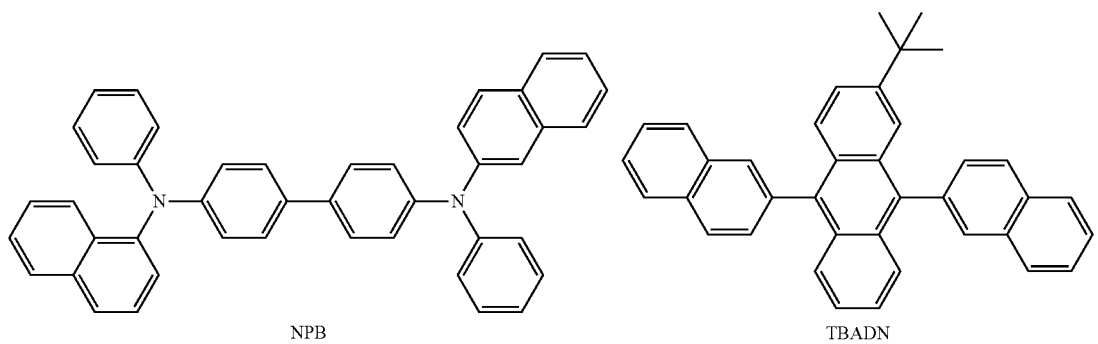

NPB                                                TBADN

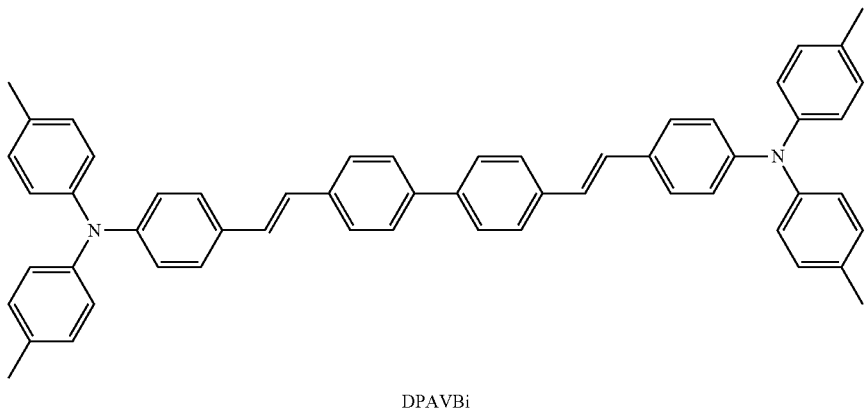

DPAVBi

Example 2

An organic light-emitting device was manufactured in the same manner as described with respect to Example 1, except that Compound 4 was used instead of Compound 1 to form an electron transport layer (ETL).

Comparative Example 1

An organic light-emitting device was manufactured in the same manner as described with respect to Example 1, except that Alq$_3$ was used instead of Compound 1 to form an electron transport layer (ETL).

Comparative Example 2

An organic light-emitting device was manufactured in the same manner as described with respect to Example 1, except that Compound A was used instead of Compound 1 to form an electron transport layer (ETL).

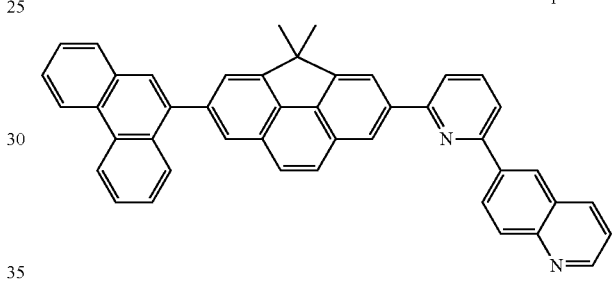

Compound A

Evaluation Example 1

The driving voltage, current density, efficiency, emission color, and half-lifespan at 1000 nit (cd/m$^2$) of the organic light-emitting devices manufactured as described with respect to Examples 1 and 2 and Comparative Examples 1 and 2 were measured by using Keithley SMU 236 and luminance meter PR650, and results thereof are shown in Table 1. The half-lifespan is a period of time that elapses until the luminance of an organic light-emitting device is reduced to 50% of the initial luminance.

TABLE 1

|  | Material of Electron Transport Layer | Driving Voltage (V) | Current Density (mA/cm$^2$) | Efficiency (cd/A) | Emission Color | Half-lifespan (hr) |
| --- | --- | --- | --- | --- | --- | --- |
| Example 1 | Compound 1 | 5.5 | 20 | 8.7 | Blue | 5000 |
| Example 2 | Compound 4 | 5.6 | 20 | 8.6 | Blue | 4700 |
| Comparative Example 1 | Alq$_3$ | 6.3 | 20 | 6.1 | Blue | 2400 |
| Comparative Example 2 | Compound A | 6.3 | 20 | 4.4 | Blue | 800 |

From Table 1, it was confirmed that the organic light-emitting devices of Examples 1 and 2 had a lower driving voltage, a higher efficiency, and a longer half-lifespan than the organic light-emitting devices of Comparative Examples 1 and 2.

According to one or more embodiments, an organic light-emitting device including the above-described condensed-cyclic compound may have a low driving voltage, a high efficiency, a high luminance, and a long lifespan.

It should be understood that example embodiments described herein should be considered in a descriptive sense only and not for purposes of limitation. Descriptions of features or aspects within each example embodiment should typically be considered as available for other similar features or aspects in other example embodiments.

As used herein, the term "substantially," "about," and similar terms are used as terms of approximation and not as terms of degree, and are intended to account for the inherent deviations in measured or calculated values that would be recognized by those of ordinary skill in the art. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112(a), and 35 U.S.C. § 132(a).

While one or more example embodiments have been described with reference to the accompanying drawing, it will be understood by those of ordinary skill in the art that various changes in form and details may be made therein without departing from the spirit and scope as defined by the following claims, and equivalents thereof.

What is claimed is:

1. A condensed-cyclic compound represented by Formula 1:

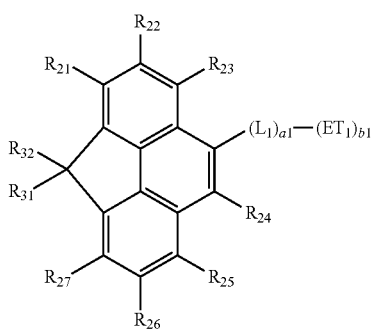

Formula 1

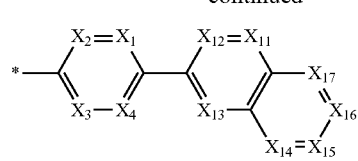

Formula 2-1

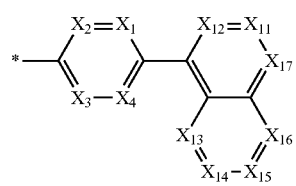

Formula 2-2

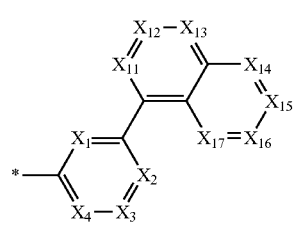

Formula 2-3

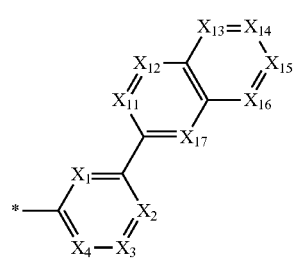

Formula 2-4 wherein, in Formulae 1 and 2-1 to 2-4, $L_1$ is selected from a substituted or unsubstituted phenylene group and a substituted or unsubstituted naphthylene group, a1 is selected from 0, 1, 2, and 3, and when a1 is 2 or more, two or more $L_1(s)$ are identical to or different from each other, $ET_1$ is an electron-transporting moiety and is selected from groups represented by Formulae 2-1 to 2-4, $X_1$ is N or $C(R_1)$, $X_2$ is N or $C(R_2)$, $X_3$ is N or $C(R_3)$, $X_4$ is N or $C(R_4)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{16}$ is N or $C(R_{16})$, and $X_{17}$ is N or $C(R_{17})$, at least one of $X_1$ to $X_4$ and $X_{11}$ to $X_{17}$ is N, b1 is selected from 1, 2, and 3, $R_1$ to $R_4$, $R_{11}$ to $R_{17}$, and $R_{21}$ to $R_{27}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted biphenyl group, a substituted or unsubstituted terphenyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_4$)($Q_5$), and —N($Q_6$)($Q_7$), $R_{31}$ and $R_{32}$ are each independently selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted biphenyl group, a substituted or unsubstituted terphenyl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, at least one of the substituents of the substituted phenylene group, substituted naphthylene group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted biphenyl group, substituted terphenyl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —B($Q_{14}$)($Q_{15}$), and —N($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a biphenyl group, a terphenyl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a biphenyl group, a terphenyl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —B($Q_{24}$)($Q_{25}$), and —N($Q_{26}$)($Q_{27}$); and —Si($Q_{31}$)($Q_{32}$)($Q_{33}$), —B($Q_{34}$)($Q_{35}$), and —N($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and \* indicates a binding site to a neighboring atom.

2. The condensed-cyclic compound of claim 1, wherein $L_1$ is selected from:

a phenylene group and a naphthylene group; and a phenylene group and a naphthylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

3. The condensed-cyclic compound of claim 1, wherein a1 is 0 or 1.

4. The condensed-cyclic compound of claim 1, wherein at least two of $X_1$ to $X_4$ and $X_{11}$ to $X_{17}$ are N.

5. The condensed-cyclic compound of claim 1, wherein at least one of $X_1$ to $X_4$ is N, and at least one of $X_{11}$ to $X_{17}$ is N.

6. The condensed-cyclic compound of claim 1, wherein one of $X_1$ to $X_4$ is N, and one of $X_{11}$ to $X_{17}$ is N.

7. The condensed-cyclic compound of claim 1, wherein $ET_1$ is selected from groups represented by Formulae 7-1 to 7-84:

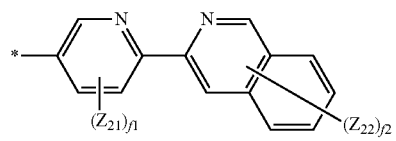

Formula 7-1

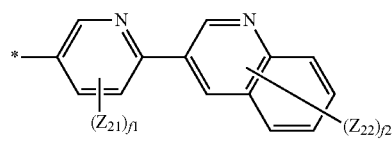

Formula 7-2

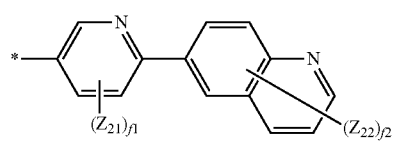

Formula 7-3

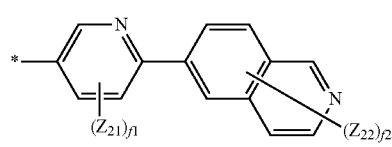

Formula 7-4

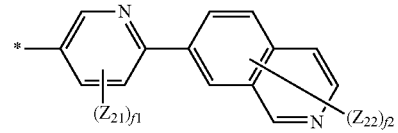

Formula 7-5

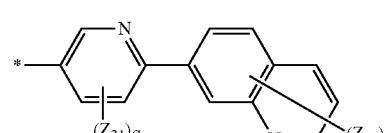

Formula 7-6

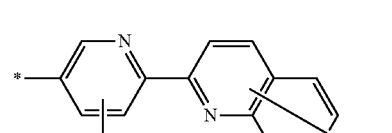

Formula 7-7

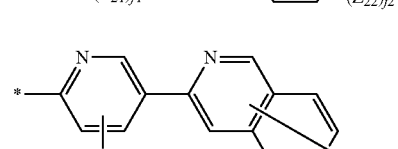

Formula 7-8

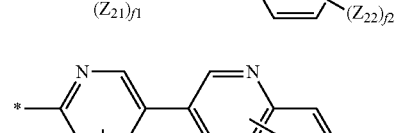

Formula 7-9

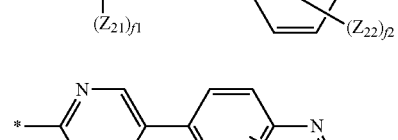

Formula 7-10

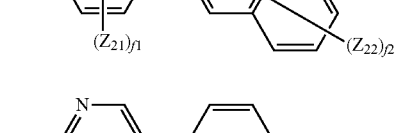

Formula 7-11

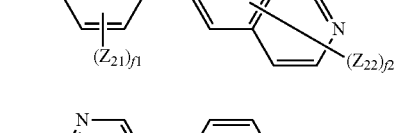

Formula 7-12

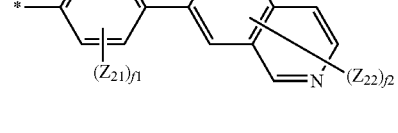

Formula 7-13

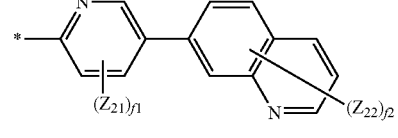

Formula 7-14

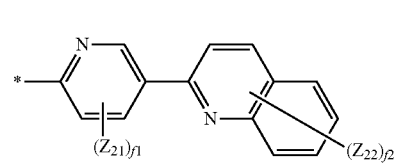

-continued
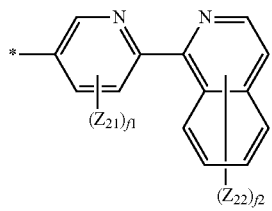
Formula 7-15
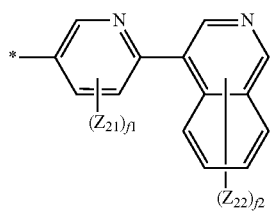
Formula 7-16
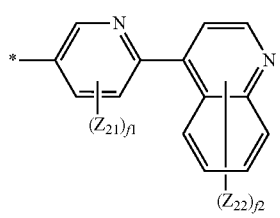
Formula 7-17
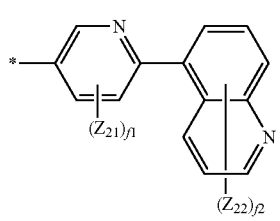
Formula 7-18
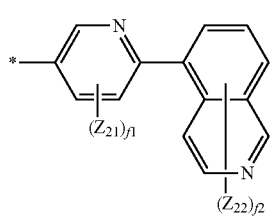
Formula 7-19
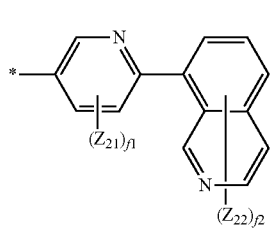
Formula 7-20
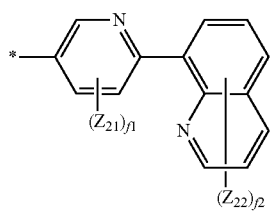
Formula 7-21
-continued
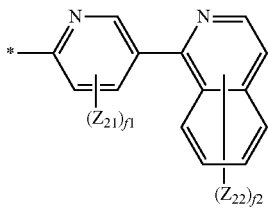
Formula 7-22
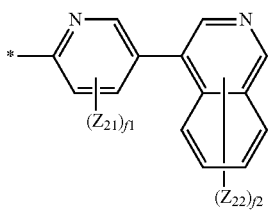
Formula 7-23
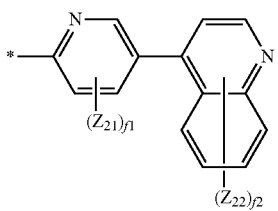
Formula 7-24
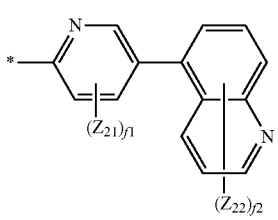
Formula 7-25
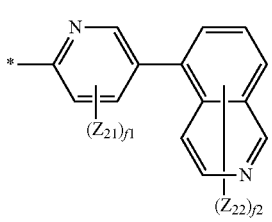
Formula 7-26
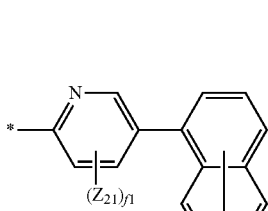
Formula 7-27
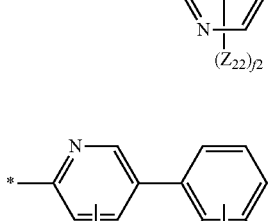
Formula 7-28

Formula 7-29
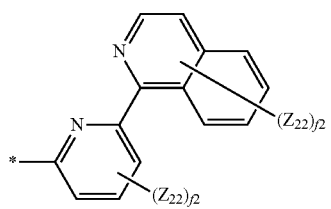
Formula 7-30
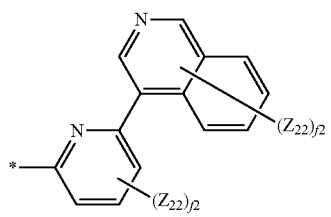
Formula 7-31
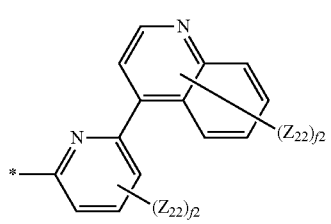
Formula 7-32
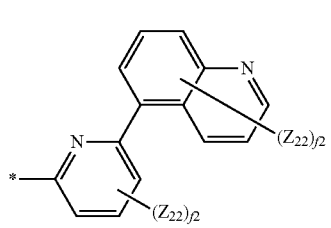
Formula 7-33
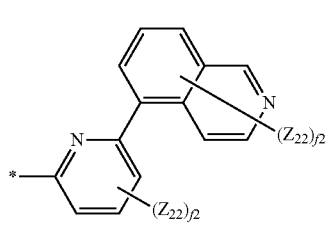
Formula 7-34
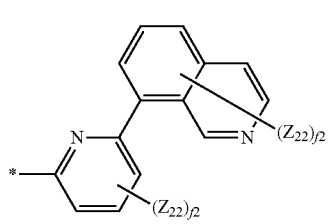
Formula 7-35
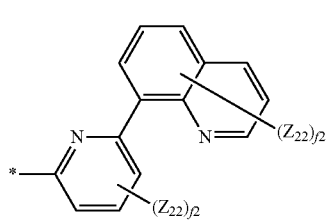
Formula 7-36
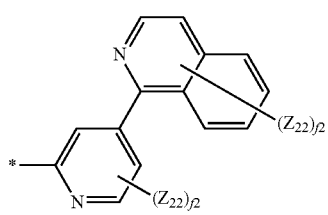
Formula 7-37
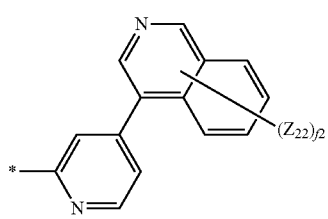
Formula 7-38
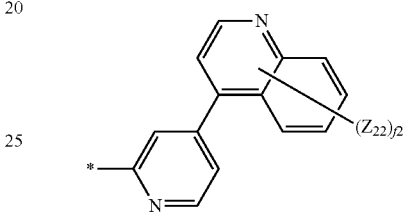
Formula 7-39
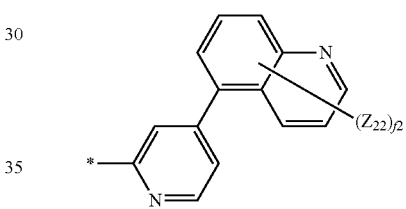
Formula 7-40
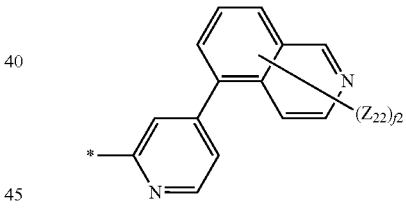
Formula 7-41
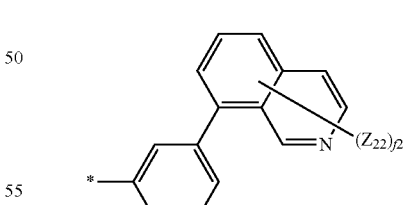
Formula 7-42
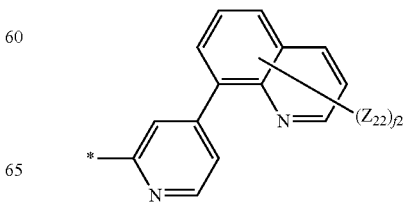

Formula 7-43
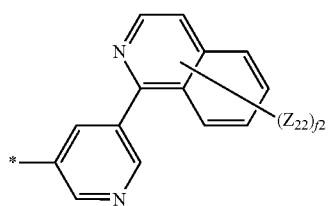
Formula 7-44
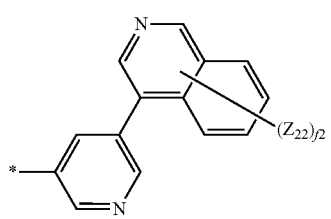
Formula 7-45
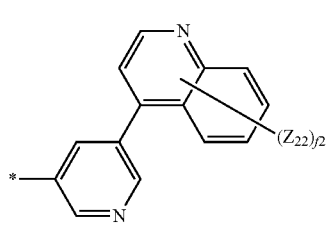
Formula 7-46
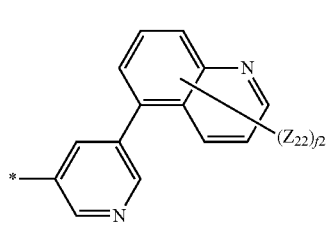
Formula 7-47
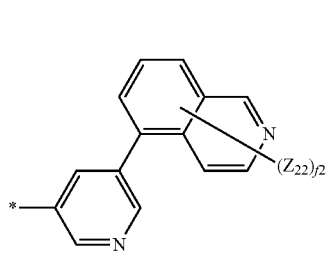
Formula 7-48
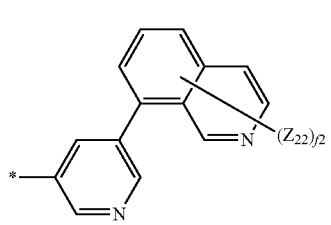
Formula 7-49
Formula 7-50
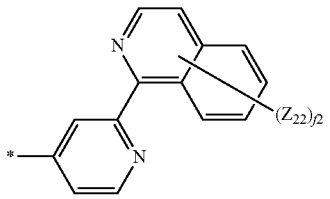
Formula 7-51
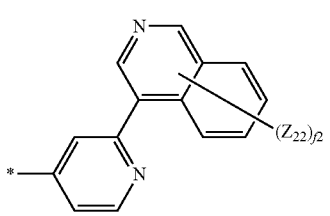
Formula 7-52
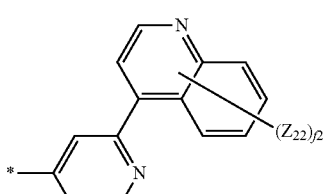
Formula 7-53
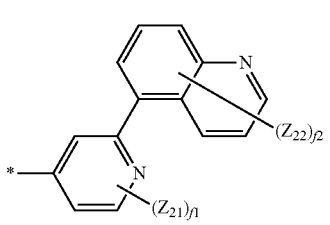
Formula 7-54
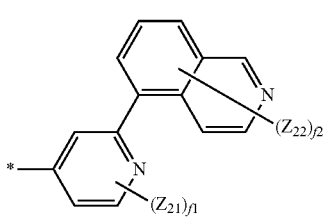
Formula 7-55
Formula 7-56
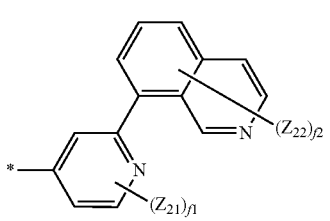

-continued
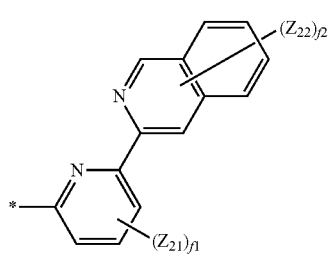
Formula 7-57
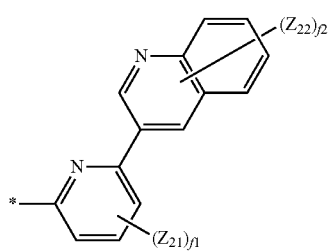
Formula 7-58
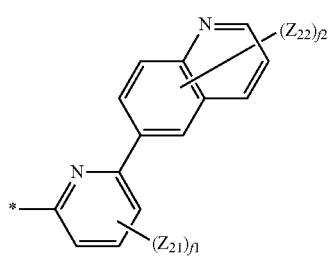
Formula 7-59
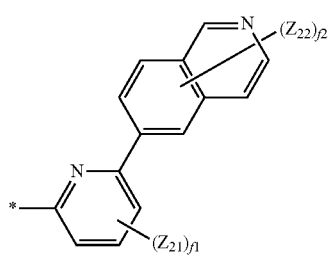
Formula 7-60
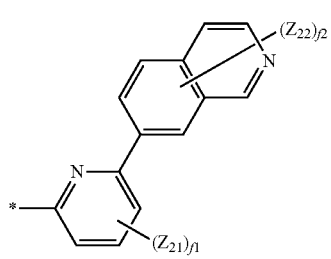
Formula 7-61
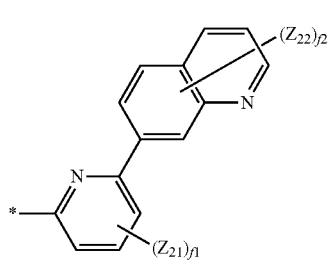
Formula 7-62
-continued
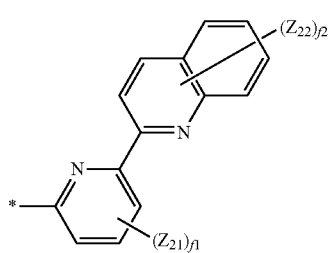
Formula 7-63
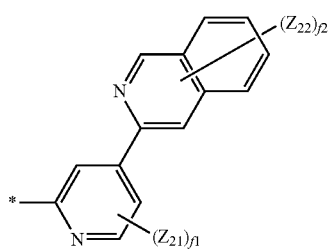
Formula 7-64
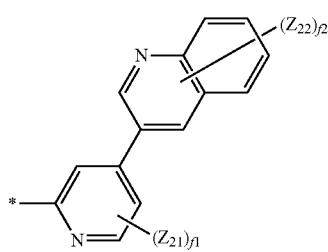
Formula 7-65
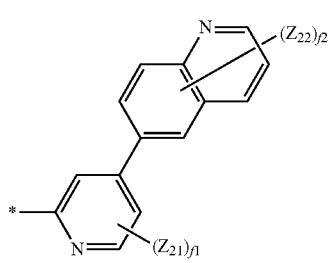
Formula 7-66
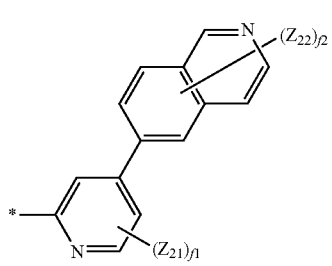
Formula 7-67
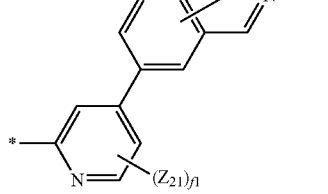
Formula 7-68

-continued
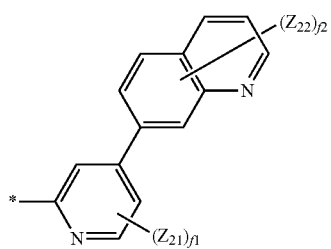
Formula 7-69
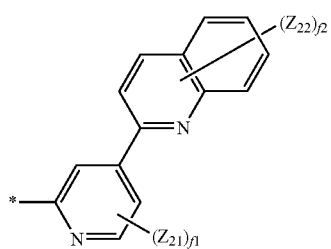
Formula 7-70
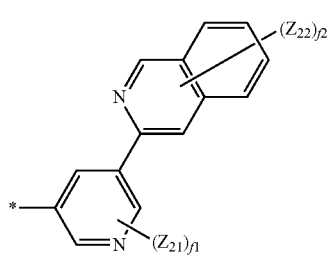
Formula 7-71
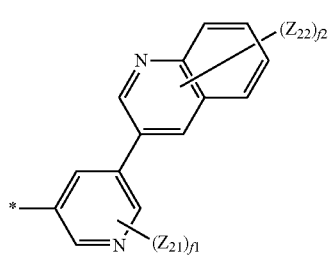
Formula 7-72
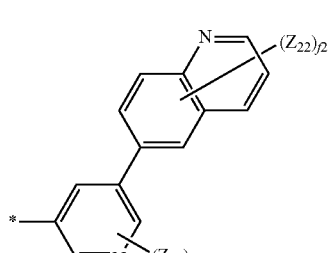
Formula 7-73
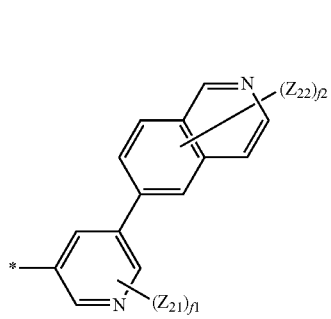
Formula 7-74
-continued
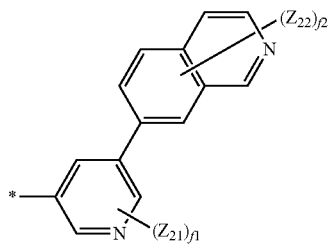
Formula 7-75
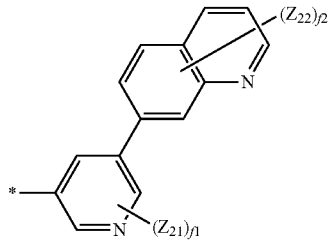
Formula 7-76
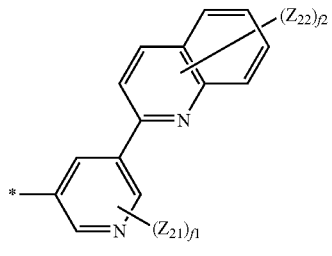
Formula 7-77
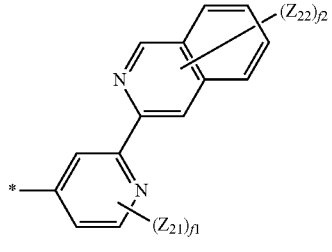
Formula 7-78
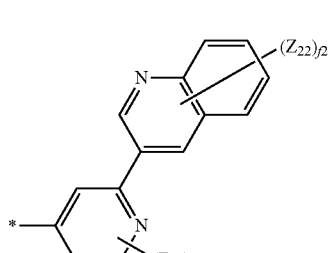
Formula 7-79
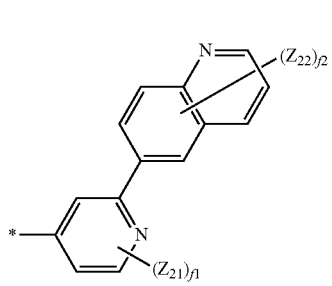
Formula 7-80

-continued

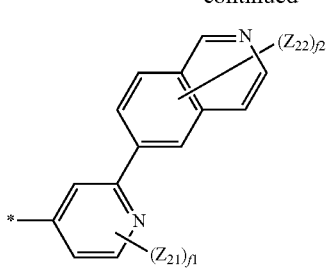
Formula 7-81

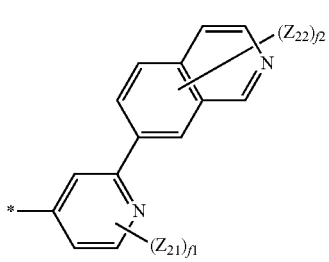
Formula 7-82

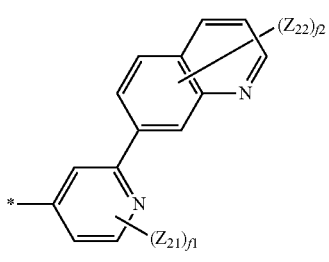
Formula 7-83

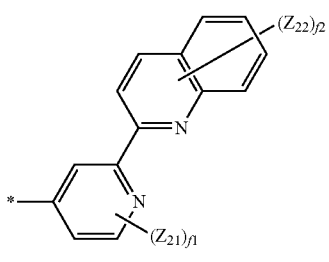
Formula 7-84 wherein, in Formulae 7-1 to 7-84, $Z_{21}$ and $Z_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, and a naphthyl group, f1 is an integer selected from 1, 2, and 3, f2 is an integer selected from 1, 2, 3, 4, 5, and 6, and

* indicates a binding site to a neighboring atom.

8. The condensed-cyclic compound of claim 7, wherein $Z_{21}$ and $Z_{22}$ in Formulae 7-1 to 7-84 are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group.

9. The condensed-cyclic compound of claim 1, wherein:

$R_1$ to $R_4$ and $R_{11}$ to $R_{17}$ are each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a phenyl group, a naphthyl group, a pyridinyl group, a pyrimidinyl group, a triazinyl group, a biphenyl group, and a terphenyl group;

a phenyl group, a naphthyl group, a pyridinyl group, a pyrimidinyl group, a triazinyl group, a biphenyl group, and a terphenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and —Si($Q_{31}$)($Q_{32}$)($Q_{33}$); and —Si($Q_1$)($Q_2$)($Q_3$), and $R_{21}$ to $R_{27}$ are each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a phenyl group, a naphthyl group, a biphenyl group, and a terphenyl group;

a phenyl group, a naphthyl group, a biphenyl group, and a terphenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a biphenyl group, a terphenyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

10. The condensed-cyclic compound of claim 1, wherein $R_{31}$ and $R_{32}$ are each independently selected from:

a $C_1$-$C_{20}$ alkyl group and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a carbazolyl group, a dibenzofuranyl group, a dibenzothiophenyl group, a biphenyl group, and a terphenyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a carbazolyl group, a dibenzofuranyl group, a dibenzothiophenyl group, a biphenyl group, and a terphenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a carbazolyl group, a dibenzofuranyl group, a dibenzothiophenyl group, a biphenyl group, a terphenyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

11. The condensed-cyclic compound of claim 1, wherein $R_{31}$ and $R_{32}$ are each independently selected from:

a methyl group, an ethyl group, a propyl group, a butyl group, a pentyl group, a methoxy group, an ethoxy group, a propoxy group, a butoxy group, and a pentoxy group;

a phenyl group, a naphthyl group, a biphenyl group, and a terphenyl group;

a phenyl group, a naphthyl group, a biphenyl group, and a terphenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a biphenyl group, a terphenyl group, and —Si($Q_{31}$)($Q_{32}$)($Q_{33}$); and —Si($Q_1$)($O_2$)($Q_3$), wherein $Q_1$ to $Q_3$ and $Q_{31}$ to $O_{33}$ are each independently selected from a $C_1$-$C_{10}$ alkyl group, a $C_1$-$C_{10}$ alkoxy group, a phenyl group, and a naphthyl group.

12. The condensed-cyclic compound of claim 1, wherein:

$R_1$ to $R_4$ and $R_{11}$ to $R_{17}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —Si($Q_1$)($Q_2$)($Q_3$), and groups represented by Formulae 5-1 to 5-14, $R_{21}$ to $R_{27}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —Si($Q_1$)($Q_2$)($Q_3$), and groups represented by Formulae 5-1 to 5-5 and Formula 5-14, and $R_{31}$ and $R_{32}$ are each independently selected from a $C_1$-$C_{10}$ alkyl group, a $C_1$-$C_{10}$ alkoxy group, and groups represented by Formulae 5-1 to 5-5 and Formula 5-14, wherein $Q_1$ to $Q_3$ are each independently selected from a $C_1$-$C_{10}$ alkyl group, a $C_1$-$C_{10}$ alkoxy group, a phenyl group, and a naphthyl group:

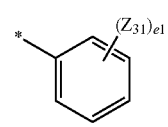

Formula 5-1

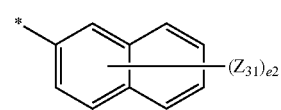

Formula 5-2

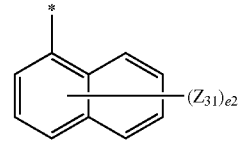

Formula 5-3

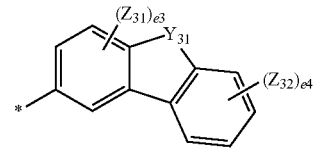

Formula 5-4

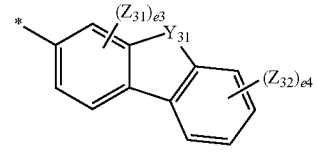

Formula 5-5

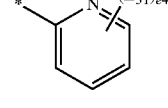

Formula 5-6

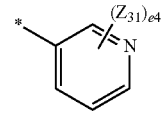

Formula 5-7

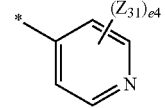

Formula 5-8

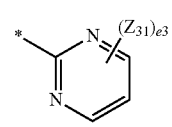

Formula 5-9

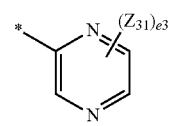

Formula 5-10

-continued

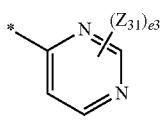
Formula 5-11

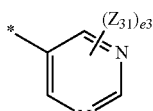
Formula 5-12

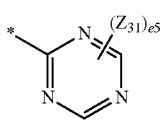
Formula 5-13

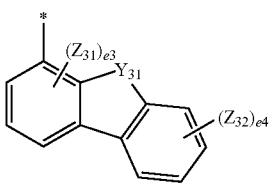
Formula 5-14 wherein, in Formulae 5-1 to 5-14,
$Y_{31}$ is O, S, $C(Z_{33})(Z_{34})$, $N(Z_{35})$ or $Si(Z_{36})(Z_{37})$,
$Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a biphenyl group, and a terphenyl group,
e1 is an integer selected from 1, 2, 3, 4, and 5,
e2 is an integer selected from 1, 2, 3, 4, 5, 6, and 7,
e3 is an integer selected from 1, 2, and 3,
e4 is an integer selected from 1, 2, 3, and 4,
e5 is 1 or 2,
* indicates a binding site to a neighboring atom.
13. The condensed-cyclic compound of claim 1, wherein:
$R_1$ to $R_4$ and $R_{11}$ to $R_{17}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —$Si(Q_1)(Q_2)(Q_3)$, and groups represented by Formulae 6-1 to 6-29,
$R_{21}$ to $R_{27}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —$Si(Q_1)(Q_2)(Q_3)$, and groups represented by Formulae 6-1 to 6-15 and Formulae 6-19 to 6-29, and $R_{31}$ and $R_{32}$ are each independently selected from a $C_1$-$C_{20}$ alkyl group, a $C_1$-$C_{20}$ alkoxy group, and groups represented by Formulae 6-1 to 6-15 and Formulae 6-19 to 6-29,
wherein $Q_1$ to $Q_3$ are each independently selected from a $C_1$-$C_{10}$ alkyl group, a $C_1$-$C_{10}$ alkoxy group, a phenyl group, and a naphthyl group:

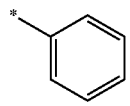
Formula 6-1

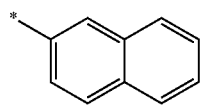
Formula 6-2

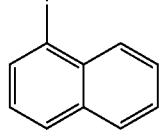
Formula 6-3

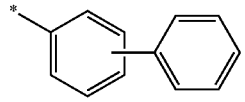
Formula 6-4

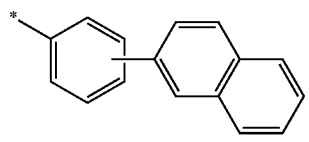
Formula 6-5

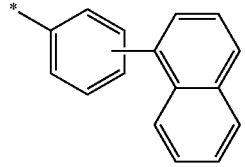
Formula 6-6

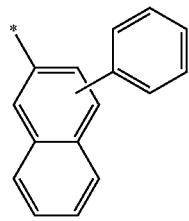
Formula 6-7

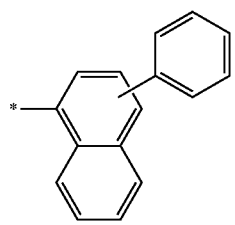
Formula 6-8

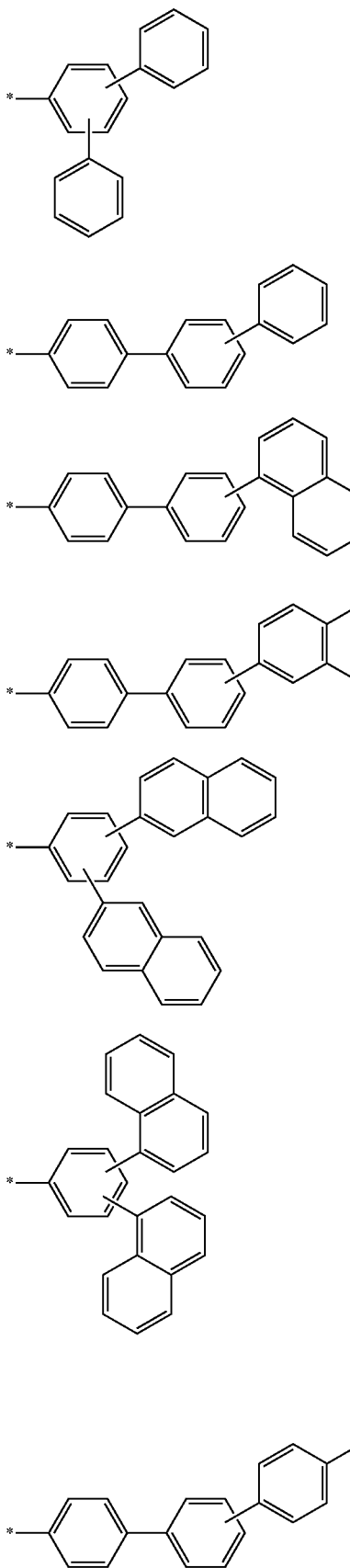

127
-continued

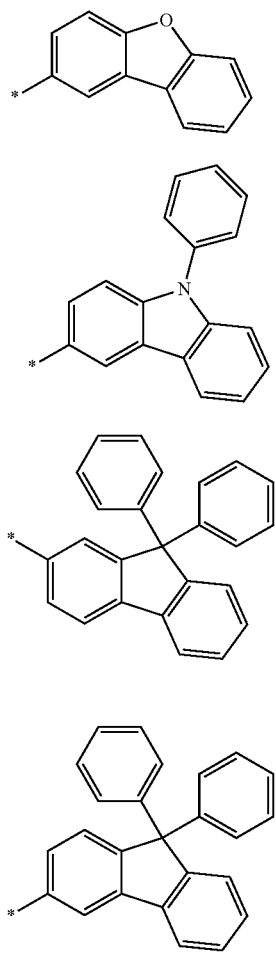

Formula 6-26

Formula 6-27

Formula 6-28

Formula 6-29 wherein * in Formulae 6-1 to 6-29 indicates a binding site to a neighboring atom.

14. The condensed-cyclic compound of claim 13, wherein:
$R_1$ to $R_4$, $R_{11}$ to $R_{17}$, and $R_{21}$ to $R_{27}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group,
$R_{31}$ and $R_{32}$ are each independently selected from a $C_1$-$C_{20}$ alkyl group, a $C_1$-$C_{20}$ alkoxy group, and groups represented by Formulae 6-1 to 6-15, and
$Q_1$ to $Q_3$ are each independently selected from a $C_1$-$C_{10}$ alkyl group, a $C_1$-$C_{10}$ alkoxy group, a phenyl group, and a naphthyl group.

15. The condensed-cyclic compound of claim 1, wherein the condensed-cyclic compound is represented by Formula 1-1:

128

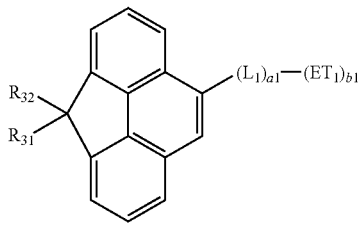

Formula 1-1 wherein $L_1$, a1, $ET_1$, b1, $R_{31}$, and $R_{32}$ in Formula 1-1 are as defined in claim 1.

16. The condensed-cyclic compound of claim 1, wherein the condensed-cyclic compound is represented by Formula 1(A) or 1(B):

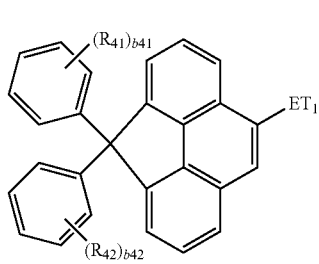

Formula 1(A)

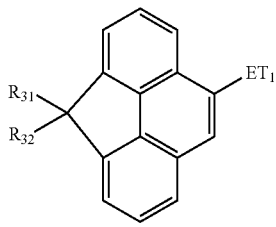

Formula 1(B)

wherein, in Formulae 1(A) and 1(B), $ET_1$ is as defined in claim 1, $R_{41}$ and $R_{42}$ are the same as defined with respect to $R_1$ in claim 1, b41 and b42 are each independently an integer selected from 1, 2, 3, 4, and 5, and $R_{31}$ and $R_{32}$ are each independently selected from a $C_1$-$C_{20}$ alkyl group and a $C_1$-$C_{20}$ alkoxy group.

17. The condensed-cyclic compound of claim 1, wherein the condensed-cyclic compound is represented by one of Compounds 1 to 7 below:

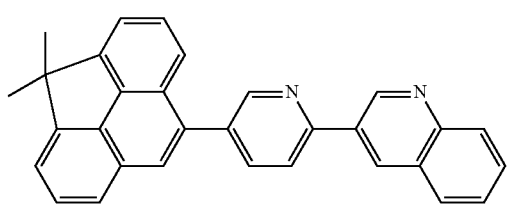

1

-continued

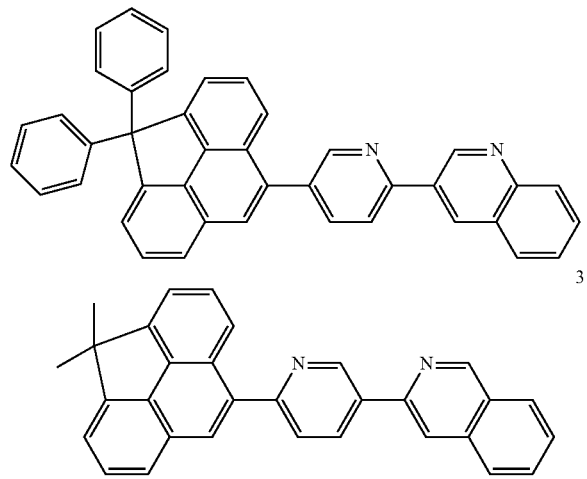

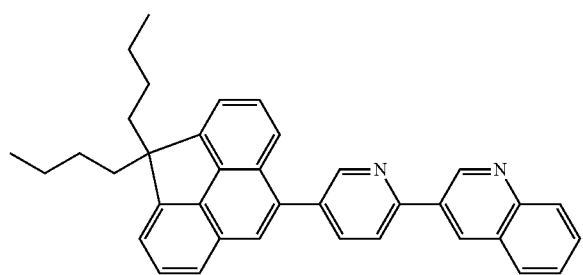

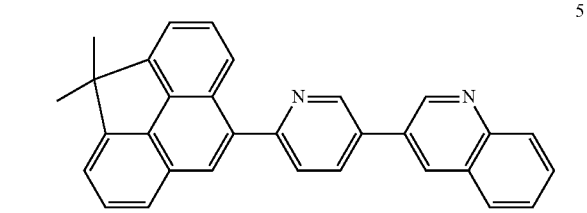

-continued

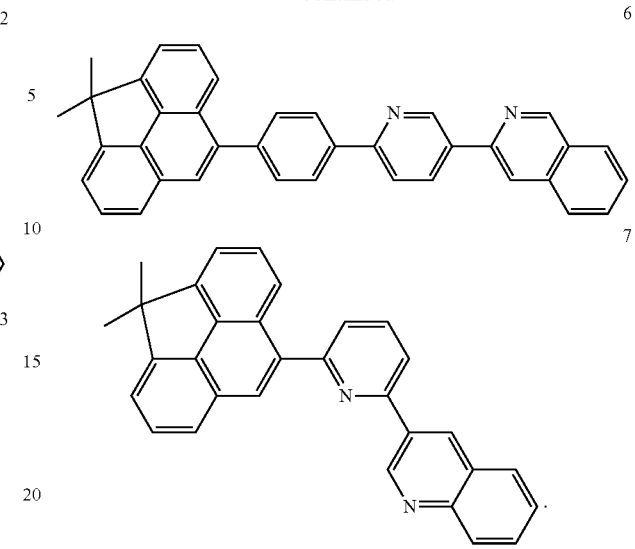

18. An organic light-emitting device comprising a first electrode, a second electrode facing the first electrode, and an organic layer between the first electrode and the second electrode, the organic layer comprising an emission layer, wherein the organic layer comprises at least one of the condensed-cyclic compounds of claim 1.

19. The organic light-emitting device of claim 18, wherein:
the first electrode is an anode,
the second electrode is a cathode,
the organic layer comprises a hole transport region and an electron transport region,
the hole transport region is between the first electrode and the emission layer and comprises at least one selected from a hole injection layer, a hole transport layer, a buffer layer, and an electron blocking layer, and
the electron transport region is between the emission layer and the second electrode and comprises at least one selected from a hole blocking layer, an electron transport layer, and an electron injection layer.

20. The organic light-emitting device of claim 19, wherein the condensed-cyclic compound is present in the electron transport region.

* * * * *